United States Patent
de Lencastre et al.

(10) Patent No.: US 6,251,647 B1
(45) Date of Patent: *Jun. 26, 2001

(54) AUXILIARY GENES AND PROTEINS OF METHICILLIN RESISTANT BACTERIA AND ANTAGONISTS THEREOF

(75) Inventors: Herminia de Lencastre; Alexander Tomasz, both of New York, NY (US)

(73) Assignee: The Rockefeller University, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 08/984,618

(22) Filed: Dec. 3, 1997

Related U.S. Application Data

(62) Continuation-in-part of application No. 08/961,595, filed on Oct. 31, 1997, now abandoned, and a continuation-in-part of application No. 08/403,918, filed as application No. PCT/US94/13952 on Dec. 6, 1994, now Pat. No. 6,063,613, which is a continuation-in-part of application No. 08/163,053, filed on Dec. 6, 1993, now abandoned.

(51) Int. Cl.$^7$ .............................. C12N 9/10; C12N 15/00
(52) U.S. Cl. ...................... 435/193; 435/252.1; 435/471; 435/320.1; 435/252.33; 536/23.1
(58) Field of Search .............................. 435/252.1, 320.1, 435/193, 252.33; 431/471; 536/23.1

(56) References Cited

U.S. PATENT DOCUMENTS 5,712,108 * 1/1998 Peery et al. ............................ 435/15

FOREIGN PATENT DOCUMENTS 0 786 519 A2 * 7/1997 (EP).

OTHER PUBLICATIONS

Beck et al. (1985) J. Bacteriol. 165:373–8.
Berger–Bachi et al. (1992) Anitmicrob. Agents Chemother. 36:1367–73.
Berger–Bachi et al. (1990) In: Mol. Biol. Staphylococci, Novick,R.P.M. ed., pp. 509–520, VCH Publishers, Inc., New York.
Berger–Bachi et al. (1989) Mol. Gen. Genet. 219:263–9.
Billington et al. (1995) Microbiol. 141:945–57.
Daniel et al. (1993) J. Gen. Microbiol. 139:361–70.
De Jonge et al. (1991) J. Bacteriol. 173:1105–10.
De Jonge et al. (1992) J. Biol. Chem. 269:11255–9.
De Jonge et al. (1992) J. Biol. Chem. 267:11248–54.
De Jonge et al. (1993) J. Bacteriol. 175:2779–82.
De Jonge et al. (1993) Anitmicrob. Agents Chemother. 37:342–6.
De Lencastre et al. (1991) Anitmicrob. Agents Chemother. 35:632–9.
De Lencastre et al. (1994) Anitmicrob. Agents Chemother. 38:2590–8.
De Lencastre et al. (1994) J. Anitmicrob. Chemother. 33:7–24.
Eveland et al. (1997) Biochem. 36:6223–9.
Gustafson et al. (1993) In: Abst. 93rd General Meet. Am. Soc. Microbiol., Abst. A–97, p. 18.
Gustafson et al. (1994) J. Bacteriol. 176:1460–7.
Hartman et al. (1984) J. Bacteriol. 158:513–6.
Hartman et al. (1986) Anitmicrob. Agents Chemother. 29:85–92.
Joyard et al. (1987) In: Biochem. Plants, Stumpf ed., Academic Press, New York, pp. 215–74.
Kawazu et al. (1995) J. Bacteriol. 177:5547–53.
Kornblum et al. (1986) Eur. J. Clin. Microbiol. 5:714–8.
Maidhof et al. (1991) J. Bacteriol. 173:3507–13.
Matthews et al. (1990) Anitmicrob. Agents Chemother. 34:1777–9.
Matthews et al. (1990) In: Mol. Biol. Staphylococci, Novick et al. Eds., VCH Publishers, New York, pp. 69–83.
Michaud et al. (1990) Eur. J. Biochem. 194:853–61.
Murakami et al. (1989) J. Bacteriol. 171:874–9.
Novick (1974) Mol. Gen. Genetics 135:131–47.
Novick, R., Plasmids, pp. 103–23.
Ornelas–Soares et al. (1994) J. Biol. Chem. 269:27246–50.
Ornelas–Soares et al. (1993) J. Biol. Chem. 268:26268–72.
Pattee (1981) J. Bacteriol. 145:479–88.
Price et al. (1997) J. Bacteriol. 179:4959–61.
Pucci et al. (1997) J. Bacteriol. 179:5632–5.
Reynolds et al. (1989) FEMS Microbiol. Lett. 33:251–4.
Stewart et al. (1981) Curr. Microbiol. 5:227–30.
Tomasz (1990) In: Mol. Biol. Staphylococci, Novick et al. eds., VHC Publishers, New York, pp. 565–583.
Tomasz et al. (1986) Anitmicrob. Agents Chemother.35:124–9.
Utsui et al. (1985) Anitmicrob. Agents Chemother. 28:397–403.
Van Heijenoort et al. (1994) In: Bact. Cell Wall, Ghuysen et al. eds., Elsevier Sci. B. V., Amsterdam, pp. 39–54.
Daniel et al. (1996) J. Bacteriol. 178:2343–50.
Fleischmann et al. (1995) Science 269:496–512.
Good et al. (1972) J. Bacter. 111:220–30.
Henriques et al. (1992) Biochimie 74:735–48.
Ikeda et al. (1990) Nuc. Acid. Res. 18:4014.
Liao et al. (1995) Antimicrob. Agent. Chemother. 39:1871–4.

(List continued on next page.)

*Primary Examiner*—Ponnathapu Achutamurthy
*Assistant Examiner*—Bradley S. Mayhew
(74) *Attorney, Agent, or Firm*—Klauber & Jackson

(57) ABSTRACT

The present invention is directed to the identification of mutant strains of methicillin resistant bacteria, in particular methicillin resistant *Staphylococcus aureus*, to identify the characteristics of such bacteria and develop drugs that can reverse, inhibit, or reduce bacterial resistance to beta lactam antibiotics, e.g., methicillin. The invention particularly relates to identification of a novel mutant strain of methicillin resistant *S. aureus* that manifests a unique phenotype. Accordingly, the invention provides for methods of treatment and corresponding pharmaceutical compositions for treating bacterial, particularly staphylococcal, infections.

13 Claims, 26 Drawing Sheets

U.S. PATENT DOCUMENTS

Michaud et al. (1990) Biochem. J. Lett. 269:277–8.
Mikuni et al. (1994) Proc. Natl. Acad. Sci. 91:5798–802.
Miyao et al. (1992) Gene 118:147–8.
Oshida et al. (1992)J. Bacteriol. 174:4952–9.
Parquet et al. (1989) Nuc. Acid. Res. 17:5379.
Tao et al. (1989) Can. J. Microiol. 35:1051–4.
Vaganay et al. (1996) Microb. Drug Resist. 2:51–4.
Varon et al. (1996) Mol. Microbiol. 20:339–50.
Ornelas–Soares et al. Journal of Biological Chemistry, Nov. 4, 1994, vol. 269, No. 44, pp. 27246–27250.*

De Lencastre et al. Antimicrobial Agents and Chemotherapy, Nov. 1, 1994,vol. 38, No. 11, pp. 2590–2598.*

Ludovice AM, et al. Molecular cloning and DNA sequencing of the *Staphylococcus aureus* UDP–N–acetylmuramyl tripeptide synthetase (murE) gene, essential for the optimal expression of methicillin resistance. Microb Drug Resist., Jun. 1998, vol. 4, pp. 85–90.*

* cited by examiner

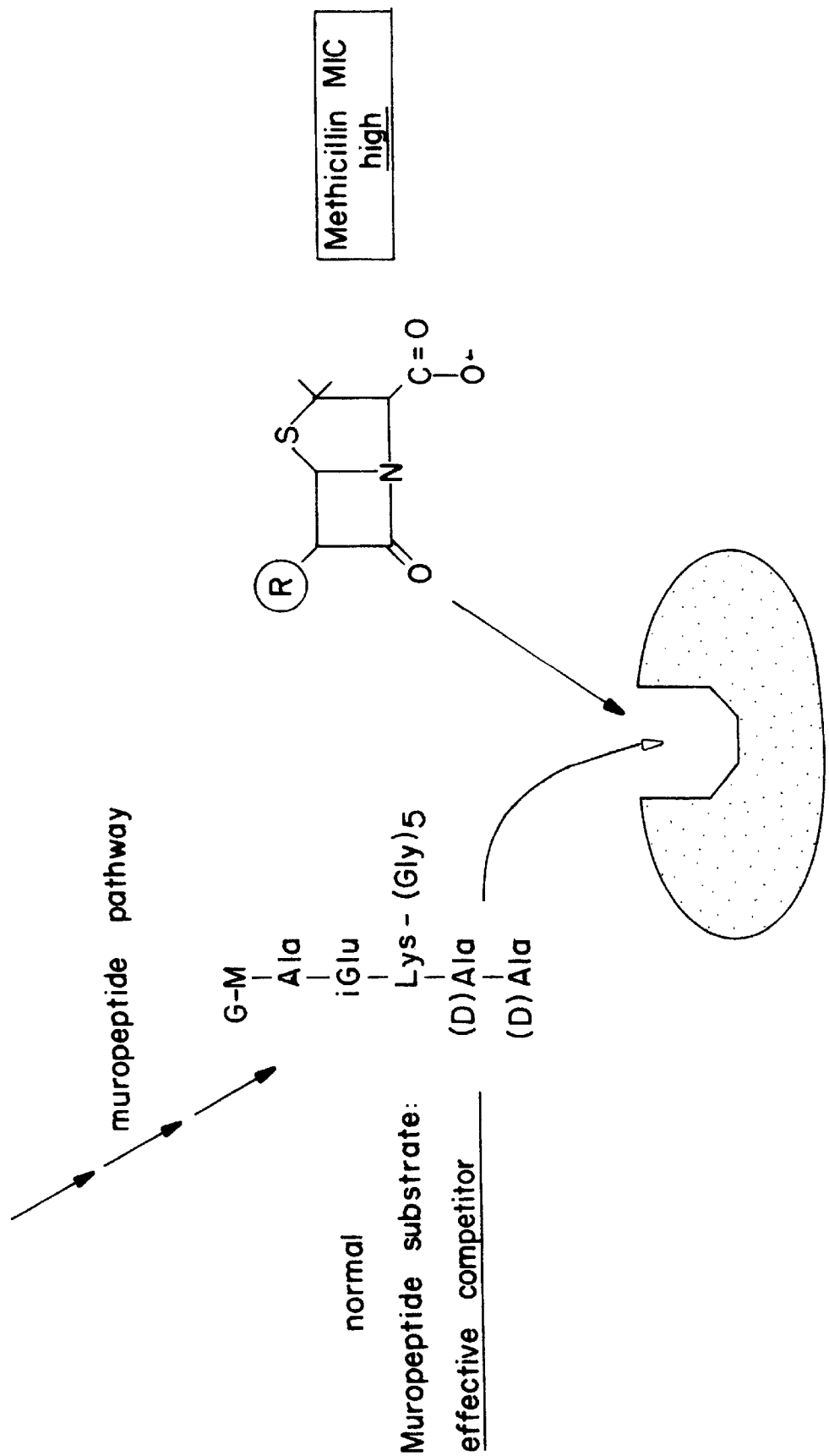

DNA inserts in recombinant phage or plasmid clones

λDII/R235/E13
13 kb EcoRI fragment DNA
of RUSA235 mutant

DNA inserts in recombinant phage or plasmid clones pAML1
pGEM-3Z+5.5kb SalI fragment
(LJ - left junction)

DNA inserts in recombinant phage or plasmid clones pAML3
pGEM-3Z+7.5kb SalI fragment
(RJ - right junction)

FIG. 13A

```
         HpaI                                                                54
5'  GTT AAC TTT ACA TCG ACA AAA TAA TAT AAT ATC CAT GCA ATT AAA ACG ACT AAA
                                                                            108
    GAC ATC ATG AAG GCA AAG CGT GTT GGG TGC ACT TTG ATA AGT AGA TTC ATA AAA
                                                                            162
    ACC ATA CCT ACC AAT AGG CCT AAC AAC CAT GAA AAA TAA ACA TAG CCC ATT TGT
                                                                            216
    TTG CCA CGT TTA TCT TCT TCA ACA CTG GAT AAC ATA ATG ACC CAA ATA GGA CTA
                                                                            270
    ACT GCA ATA CCG ANC ATC ATA GCA CTA AAT ATG ATT ACA AAA GGT GAT GCT GGG
                                                                            324
    AAA CCA AAT AAC TAA AAA TAA ACT TGT TAA TGC TAA AAT AAA TCC AGC GTT AAA
                                                                            378
    ACG ATT TTT GTG CCG AAT TTT TTC AGT AAA AAT CCT ATA ACA AAG TTT GTA GAT
                                                                            432
    GCA TCA GCA ATA AAA TGT ATT GAA AAT GCT AGA GAC GTT ATT GCT ACA GCA ATG
                                                                            486
    GAT GTA ACT GTT GGC AAG AAA TTA ATA TAG CTT AGG ATA TAC ATG CCT CTC GCA
                                                                            540
    AAT TCC ATT AAA AAT AAG ATA ATA AGC ATT AAA ATG AAA TTT TTA TGA TTA GCG
          *   K   V   F   F   R   A   Y   L   P   V   K   G   Y   I   E   Q  594
    TAA TTA TTT AAC GAA GAA TCT GCA TAA AGG AAC CTT CCA TAA ATC TCT TG
      P   Q   S   S   H   G   I   L   D   L   D   R   C   I   T   Q   T     648
    TGG TTG TGA TGA ATG ACC GAT AAA TCA AGT AAG TCT CGA CAT ATG TCT GTC
      A   Y   K   I   D   Q   E   M   T   S   I   M   N   T   L   Q   E     702
    AGC ATA CTT AAT TTT ATC TTG TTC CAT TGT ACT AAT CAT GTT AGT TAA TTG CTC
      N   G   N   T   L   S   A   V   I   K   I   A   E   E   P   T   D   A  756
    ATT ACC GTT AGT TAA ACT TGC TAC AAT TTT TAT TGC TTC TTC TGG AGT ATC AGC
      I   K   G   F   G   K   E   E   F   Y   F   A   N   E   L   E   Q   G  810
    GAT TTT ACC AAA ACC TTT TTC TTC AAA GTA AAA GGC ATT TTC AAG CTC TTG ACC
      P   A   P   N   X   F   I   M   P   I   C   R   A   F   G   E   T   I  864
    AGG TGC AGG ATT TAN GAA AAT CAT TGG AAT ACA ACG GGC GAA ACC TTC AGT TAT
      T   I   G   P   K   T   I   M   L   Q   S   S   A   M   W   E   N     918
    TGT GAT ACC ACC AGG TTT CGT AAT CAT AAG TTG ACT TGA TGC CAT CCA TTC ATT
      M   H   K   T   Y   G   L   I   L   Y   M   R   T   L   K   F   K   A  972
    CAT GTG TTT GGT ATA CCT AGA ATC AAA TAC ATC TCG TAA TTT AAA CTT AGC
      T   L   S   R   K   L   E   K   S   K   G   C   I   M   V   V   Q   A  1026
    TGT TAA AGA ACG CTT TAG CTC TTT GCT CTT ACC ACA AAT CAT AAC TAC TTG TGC
      N   A   S   K   A   L   I   D   T   I   M   T   D   F   G   K   S   V  1080
    ATT TGC ACT TTT CGC TAA TAT ATC AGT AAT CAT CGT GTC AAA ACC TTT AGA TAC
      G   F   A   G   A   S   M   L   I   T   Q   K   D   P   D   L   N   N  1134
    ACC AAA TGC ACC AGC TGA CAT TAA AAT AGT TTG CTT ATC TGG ATC TAA GTT GTT
      D   I   L   W   Q   K   Q   N   I   P   T   E   F   K   N   D   I   P  1188
    GTC TAT TAA CCA CTG CTT TGA TTA ATA GGC GTT CAA ATT TGT TAT CAA TAG G
      I   G   T   V   K   V   T   S   P   D   I   G   V   D   I   F   D   Q  1242
    AAT ACC TGT CAC TTT AAC TGT TGA AGG ATC AAT ACC TAC GTC TAT GAA GTC TTG
      K   T   E   K   T   A   V   Y   Y   R   T   S   Y   P   T   I   W   N  1296
    TTT CGT TTC TTT TGT TGC CAC ATA ATA TCT TGT TGA ATA CGG CGT AAT CCA GTT
      K   H   L   R   Y   D   T   M   V   T   A   V   P   I   N   I   N   F  1350
    TTT ATG TAA GCG ATA GTC TGT CAT CAC TGT AGC AAC TGG AAT ATT AAT GTT AAA
      Q   E   T   L   V   S   M   V   P   T   P   F   T   L   L   I   L   D  1404
    TTG CTC AGT TAG TAC CGA CAT AAC TGG TGT AGG AAA CGT TAA TAA TAT TAA ATC
      P   K   E   K   I   L   L   N   I   L   K   N   L   G   Y   Y   K   Y  1458
```

FIG. 13B

```
TGG CTT TTC TTT TAT CAA TAA ATT AAT TAA CTT ATT AAG TCC ATA GTA TTT GTA
 F   C   K   D   L   K   D   P   R   S   Y   Y   F   G   K   Y   M   N    1512
AAA ACA TTT GTC TAG TTT ATC TGG GCG GCT GTA ATA AAA CCC TTT GTA CAT ATT
 R   F   Y   K   F   S   N   I   Y   W   K   K   C   I   S   T   L   I    1566
TCT AAA ATA TTT AAA GCT ATT GAT ATA CCA TTT TTT ACA AAT AGA AGT CAA AAT
 P   H   A   E   M   F   L   D   H   E   I   V   S   L   H   D   L   N    1620
TGG ATG AGC TTC CAT AAA TAA ATC GTG CTC AAT GAC GCT TAA ATG GTC TAG ATT
 M   D   N   L   Q   N   V   I   S   Q   T   V   Q   M   H   G   N   G    1674
CAT ATC ATT AAG TTG ATT AAC GAT ACT CTG TGT AAC TTG CAT ATG ACC GTT ACC
 F   S   G   T   I   I   L   I   K   K   N   Q   T   V   M   ypfP         1728
GAA TGA GCC AGT AAT AAT CAA TAT CTT TTT ATT TTG AGT AAC CAT TAA TAG CCA
 rbs                                                       -10             1782
CCC TCC GTT AGT TTG AAA ATT TTA TTT AAG TGT AAC TTA TTT TAC GGC ATT ATA
              -35                                                          1836
AAA GAA ATA AAG ACG CAA AGT CGT TAC ATT TAT AGC AAT TTT AAT CTA TAG ATG
                                                                           1890
AAT TGA TAC AAA ATA AAA CGT TAT TTT ATA AAG CAA TTT ATT GTT CTA TGT TTT
                                                                           1944
ATT TGT ATA TTT AAA ATT ATC CAG TAT ACA ATT ATA GCA TAT TTT TGG AAA CAA
                                                                           1998
TTA TGA TAT TAT ACC ATG TTA CAA GAT GGT TTT AAT AAT TTA AGA TGA GCC ATA
                                                                           2052
ATT GTA AAA CTA ATT CAT AAT ACC GTA TGT TTT ATT TTT AAT AGT AGA AAT TAG
                                                  -35                      2106
AAA ATG CTG ATT AGT AGG ATA TAA CAG TGA AAT TAT AAA TTT ATT AAC ATC AAC
       -10                                        rbs                      2160
AAA ACG TGT ATA ATA AAC ATA TTG TAG AAA AAG GAG CGG TTC AGT TTG GAT GCA
                                                     murE     M   Q        2214
AGT ACG TTG TTT AAA GAA AGT AAA AGT AAA GCG TGT ATT GGG TTC TTT AGA ACA
 V   R   C   L   K   K   V   K   V   K   R   V   L   G   S   L   E   Q    2268
ACA AAT AGA TGA TAT CAC TAC TGA TTC ACG TAC AGC GAG AGA AGG TAG CAT TTT
 --- --- --- --- --- --- --- --- --- --- --- --- --- --- --- --- ---
 Q   I   D   D   I   T   T   D   S   R   T   A   R   E   G   S   I   F    2322
TGT CGC TTC AGT TGG ATA TAC TGT AGA CAG TCA TAA GTT CTG TCA AAA TGT AGC
 V   A   S   V   G   Y   T   V   D   S   H   K   F   C   Q   N   V   A    2376
TGA TCA AGG GTG TAA GTT GGT AGT GGT CAA TAA AGA ACA ATC ATT ACC AGC TAA
 D   Q   G   C   K   L   V   V   V   N   K   E   Q   S   L   P   A   N    2430
CGT AAC ACA AGT GGT TGT GCC GGA CAC ATT AAG AGT AGC TAG TAT TCT AGC ACA
 V   T   Q   V   V   V   P   D   T   L   R   V   A   S   I   L   A   H    2484
CAC ATT ATA TGA TTA TCC GAG TCA TCA GTT AGG ACA TTT GGG TGT AAC GGG TAC
 T   L   Y   D   Y   P   S   H   Q   L   G   H   L   G   V   T   G   T    2538
AAA TGG TAA AAC TTC TAT TGC GAC GAT GAT TCA TTT AAT TCA AAG AAA GTT AGG
 N   G   K   T   S   I   A   T   M   I   H   L   I   Q   R   K   L   G    2592
AAA AAA TAG TGC ATA TTT AGG AAC TAA TGG TTT CCA AAT TAA TGA AAC AAA GAC
 K   N   S   A   Y   L   G   T   N   G   F   Q   I   N   E   T   K   T
```

FIG. 13C

```
                                                                          2646
AAA AGG TGC AAA TAC GAC ACC AGA AAC AGT TTC TTT AAC TAA GAA AAT TAA AGA
 K   G   A   N   T   T   P   E   T   V   S   L   T   K   K   I   K   E
                                                                          2700
AGC AGT TGA TGC AGG CGC TGA ATC TAT GAC ATT AGA AGT ATC AAG CCA TGG CTT
 A   V   D   A   G   A   E   S   M   T   L   E   V   S   H   G   L
                                                                          2754
AGT ATT AGG ACG ACT GCG AGG CGT TGA ATT TGA CGT TGC AAT ATT TTC AAA TTT

2808
AAC ACA AGA CCA TTT AGA TTT TCA TGG CAC AAT GGA AGC ATA CGG ACA CGC GAA
 T   Q   D   H   L   D   F   H   G   T   M   E   A   Y   G   H   A   K
                                                                          2862
GTC TTT ATT GTT TAG TCA ATT AGG TGA AGA TTT GTC GAA AGA AAA GTA TGT CGT
 S   L   L   F   S   Q   L   G   E   D   L   S   K   E   K   Y   V   V
                                                                          2916
GTT AAA CAA TGA CGA TTC ATT TTC TGA GTA TTT AAG AAC AGT GAC GCC TTA TGA
 L   N   N   D   D   S   F   S   E   Y   L   R   T   V   T   P   Y   E
                                                                          2970
AGT ATT TAG TTA TGG AAT TGA TGA GGA AGC CCA ATT TAT GGC TAA AAA TAT TCA
 V   F   S   Y   G   I   D   E   E   A   Q   F   M   A   K   N   I   Q
                                                                          3024
AGA ATC TTT ACA AGG TGT CAG CTT TGA TTT TGT AAC GCC TTT TGG AAC TTA CCC
 E   S   L   Q   G   V   S   F   D   F   V   T   P   F   G   T   Y   P
                                                                          3078
AGT AAA ATC GCC TTA TGT TGG TAA GTT TAA TAT TTC TAA TAT TAT GGC GGC AAT
 V   K   S   P   Y   V   G   K   F   N   I   S   N   I   M   A   A   M
                                                                          3132
GAT TGC GGT GTG GAG TAA AGG TAN NTC TTT AGA AAC GAT TAT TAA AGC TGT TGA
 I   A   V   W   S   K   G   X   S   L   E   T   I   I   K   A   V   E
                                                                          3186
AAA TTT AGA ACC TGT TGA AGG GCG ATT AGA AGT TTT AGA TCC TTC GTT ACC TAT
 N   L   E   P   V   E   G   R   L   E   V   L   D   P   S   L   P   I
                                                                          3240
TGA TTT AAT TAT CGA TTA TGC ACA TAC AGC TGA TGG TAT GAA CAA ATT AAT CGA
 D   L   I   I   D   Y   A   H   T   A   D   G   M   N   K   L   I   D
                                                                          3294
TGC AGT ACA GCC TTT TGT AAA GCA AAA GTT GAT ATT TTT AGT TGG TAT GGC AGG
 A   V   Q   P   F   V   K   Q   K   L   I   F   L   V   G   M   A   G
                                                                          3348
CGA ACG TGA TTT AAC TAA AAC GCC TGA AAT GGG GCG AGT TGC CTG TCG TGC AGA
 E   R   D   L   T   K   T   P   E   M   G   R   V   A   C   R   A   D
                                                                          3402
TTA TGT CAT TTT CAC ACC GGA TAA TCC GGC AAA TGA TGA CCC GAA AAT GTT AAC
 Y   V   I   F   T   P   D   N   P   A   N   D   D   P   K   M   L   T
                                                                          3456
GGC AGA ATT AGC CAA AGG TGC AAC ACA TCA AAA CTA TAT TGA ATT TGA TGA TCG
 A   E   L   A   K   G   A   T   H   Q   N   Y   I   E   F   D   D   R
                                                                          3510
TGC AGA AGG GAT AAA ACA TGC AAT TGA CAT AGC TGA GCC TGG GGA TAC TGT CGT
 A   E   G   I   K   H   A   I   D   I   A   E   P   G   D   T   V   V
                                                                          3564
TTT AGC ATC AAA AGG AAG AGA ACC ATA TCA AAT CAT GCC AGG GCA TAT AAA GGT
 L   A   S   K   G   R   E   P   Y   Q   I   M   P   G   H   I   K   V
```

FIG. 13D

```
                                                                      3618
GCC ACA TCG AGA TGA TTT AAT TGG CCT TGA AGC AGC TTA CAA AAA GTT CGG TGG
 P   H   R   D   D   L   I   G   L   E   A   A   Y   K   K   F   G   G
           Tn551                                                      3672
TGG CCC TGT TGA TTA ATA AAA GAT TTA TTG ATG AAG GTA AAA CTA TTG ATG TTT
 G   P   D   *
                                                                      3726
ATT TAT TCG AAG CAT TAA ATA ACC AGA TAA TCA TTG CTA TAC CAG ATT GGT TTT
                                          -35                         3780
GGT CAT ATC AGA TGG CAA TGA CAT TAG ATG AAG AAA CTT GTT TTG AAG CAA TAC
         -10                                                          3834
TCA TGC AAT TGT TTG TTT TTA AAG AAG AGG AAG AGG CAG AAT CGA TTG CAT CAC
                                                                      3888
AAC TAA CAG ATT GGA TAG AAA CAT ATA AAA AGG AGA AAG ACT AAT GAA CTT AAA
                                               RF3       M   N   L   K
        XbaI                                                          3942
GCA AGA AGT TGA GTC TAG AAA GAC TTT TGC GAT TAT TTC ACA TCC GAT GCA GG
 Q   E   V   E   S   R   K   T   F   A   I   I   S   H   P   D   A   G
                                                                      3996
GAA AAC AAC GTT AAC TGA AAA ACT ATT GTA CTT CAG TGG TGC TAT TCG TGA AGC
 K   T   T   L   T   E   K   L   L   Y   F   S   G   A   I   R   E   A
                                                                      4050
GGG TAC AGT TAA AGG GAA GAA ACT GGT AAA TTT GCG ACA AGT GAC TTG GAT GAA
 G   T   V   K   G   K   K   L   V   N   L   R   Q   V   T   W   M   K
                                                                      4104
AGT TGA ACA AGA ACG TGG TAT TTC TGT AAC TAG TTC AGT AAT GCA ATT TGA TTA
                                                                      4158
CGA TGA TTA TGA AAT CAA TAT CTT AGA TAC CCC AGG ACA TGA AGA CTT TTC NGA
 D   D   Y   E   I   N   I   L   D   T   P   G   H   E   D   F   S   E
                                                                      4212
AGA TAC NTA TAG AAC ATT AAT GGC AGT TGA CAG TGC TGT CAT GGT CAT AGA CTG
 D   T   Y   R   T   L   M   A   V   D   S   A   V   M   V   I   D   C
                                                                      4266
TGC AAA AGG TGT TGA ACC NCC AAC NTT GAA ATT ATT TAA AGT TTG TAA AAT GCG
 A   K   G   V   E   P   P   T   L   K   L   F   K   V   C   K   M   R
                                                                      4320
TGG TAT TCC AAT CTT TAC ATT CAT TAA TAA ATT AGA CCG AGT AGG TAA AGA ACC
 G   I   P   I   F   T   F   I   N   K   L   D   R   V   G   K   E   P
                                                                      4374
ATT TGA ATT ATT AGA TGA AAT CGA AGA GAC ATT AAA TAT TGA AAC ATA CCC TAT
 F   E   L   L   D   E   I   E   E   T   L   N   I   E   T   Y   P   M
                                                                      4428
GAA TTG GCC AAT TGG TAT GGG ACA AAG TTT CTT TGG CAT CAT TGA TAG AAA GTC
 N   W   P   I   G   M   G   Q   S   F   F   G   I   I   D   R   K   S
                                                                      4482
TAA AAC AAT TGA ACC ATT TAG AGA TGA AGA AAA TAT ATT ACA TTT GAA TGA TGA
 K   T   I   E   P   F   R   D   E   E   N   I   L   H   L   N   D   D
                                                                      4536
TTT TGA GTT GGA AGA AGA TCA TGC AAT TAC AAA TGA TAG TGA TTT TGA ACA AGC
 F   E   L   E   E   D   H   A   I   T   N   D   S   D   F   E   Q   A
```

FIG. 13E

```
                                                              4590
GAT TGA AGA ATT AAT GTT GGT TGA AGA AGC GGG TGA AGC CTT TGA TAA TGA CGC
 I   E   E   L   M   L   V   E   E   A   G   E   A   F   D   N   D   A
                                                              4644
GCT GTT GAG TGG AGA CTT AAC ACC TGT ATT TTT CGG TTC AGC TTT AGC TAA CTT
 L   L   S   G   D   L   T   P   V   F   F   G   S   A   L   A   N   F
                                                              4698
TGG TGT ACA AAA TTT CTT AAA TGC ATA TGT TGA TTT TGC GCC CAT GCC AAA TGC
 G   V   Q   N   F   L   N   A   Y   V   D   F   A   P   M   P   N   A
                                                              4752
GAG ACA AAC AAA AGA AAA CGT TGA AGT AAG CCC GTT TGA TGA TTC ATT TTC AGG
 R   Q   T   K   E   N   V   E   V   S   P   F   D   D   S   F   S   G
                                                              4806
ATT TAT CTT TAA AAT TCA AGC CAA CAT GGA CCC TAA ACA CCG TGA TAG AAT GCC
 F   I   F   K   I   Q   A   N   M   D   P   K   H   R   D   R   I   A
                                                              4860
CTT TAT GCG TGT CGT TAG TGG TGC ATT TGA ACG TGT ATG GAT GTT ACT TTG CAA
 F   M   R   V   V   S   G   A   F   E   R   V   W   M   L   L   C   N
                                                              4914
CGT ACT AAT AAA AAG CAA AAG ATC ACA CGT TCA ACG TCA TTT ATG GCA GAC GAT
 V   L   I   K   S   K   R   S   H   V   Q   R   H   L   W   Q   T   I
                                                              4968
AAA GAA ACT GGT GAA TCA TGC TGT AGC AGG CGA TAT CAT TGG ACT ATA TGA TAC
 K   K   L   V   N   H   A   V   A   G   D   I   I   G   L   Y   D   T
                                                              5022
TGG TAA TTA TCA AAT TGG AGA TAC TTT AGT TGG TGG AAA ACA AAC CTA CAG TTT
 G   N   Y   Q   I   G   D   T   L   V   G   G   K   Q   T   Y   S   F
                                                              5076
CCA AGA TTT ACC ACA ATT TAC GCC AGA AAT TTT TAT GAA AGT TTC TGC TAA AAA
 Q   D   L   P   Q   F   T   P   E   I   F   M   K   V   S   A   K   N
                                                              5130
CGT CAT GAA ACA GAA GCA TTT CCA TAA AGG TAT TGA ACA ATT AGT ACA AGA AGG
 V   M   K   Q   K   H   F   H   K   G   I   E   Q   L   V   Q   E   G
                                                              5184
TGC GAT TCA ATA CTA TAA AAC ATT ACA CAC AAA CCA AAT TAT TTT AGG TGC TGT
 A   I   Q   Y   Y   K   T   L   H   T   N   Q   I   I   L   G   A   V
                                                              5238
TGG TCA GTT ACA ATT TGA AGT TTT CGA ACA TAG AAT GAA AAA CGA ATA TAA TGT
 G   Q   L   Q   F   E   V   F   E   H   R   M   K   N   E   Y   N   V
                                                              5292
TGA TGT TGT TAT GGA GCC AGT AGG CCG TAA AAT TGC ACG TTG GGA CAT TGA AAA
 D   V   V   M   E   P   V   G   R   K   I   A   R   W   D   I   E   N
                                                              5346
TGA AGA CCA AAT TAC AGA TAA GAT GAA CAC ATC AAG ATC GAT TTT AGT GAA AGA
 E   D   Q   I   T   D   K   M   N   T   S   R   S   I   L   V   K   D
                                                              5400
TAG ATA TGA CGA TTT AGT ATT CTT ATT TGA AAA TGA ATT TGC AAC AAG ATG GTT
 R   Y   D   D   L   V   F   L   F   E   N   E   F   A   T   R   W   F
                                                              5454
TGA AGA GAA ATT CCC TGA AAT TAA ATT GTA TAG TTT ACT TTA ACA GCT CAA TTG
 E   E   K   F   P   E   I   K   L   Y   S   L   L   *
                                                              5508
TAT AAT CGA ATT TGT TAC ATT AAA AAT AAT TGT TTC GTT GAA GAA AAA TAA ATT
```

FIG. 13F

```
GTA TAT TTT AAA AGA AAA AGG TAT ACT ATG ATG TAT CAA ATG AAT AAC CTA TGG    5562
CAT TTT GTC AGA GGG GAG TAA CTT AAG AAT CAT GAC CGT ATA AAT GAT TCG ACA    5616
CTT TAT CGT CAT TAC GAA GAT ATC TTC CGG TAA AGT GGG CAA TTA AAT TGC TTA    5670
GTG AGA CCT TTG CTA TTT ATT TAG CAT AGG TCT TTT TGT TTG TAC TTA ACT TAT    5724
TTA TTT AAA GGA GTT GTA CAT GTT AAT GGA TCC 3'                             5757
                                    BamHI
```

AUXILIARY GENES AND PROTEINS OF METHICILLIN RESISTANT BACTERIA AND ANTAGONISTS THEREOF

CROSS-REFERENCE TO RELATED APPLICATION

This application is a continuation-in-part of Ser. No. 08/961,595, filed Oct. 31, 1997, abandoned, and a continuation-in-part of Ser. No. 08/403,918, filed Mar. 15, 1995, now U.S. Pat. No. 6,063,613, which is a National Filing under 35 U.S.C. §371 of PCT/US94/13952, filed Dec. 6, 1994, which is a continuation-in-part of Ser. No. 08/163,053, filed Dec. 6, 1993, now abandoned. Applicants claim the benefits of these Applications under 35 U.S.C. §§120 and 371.

GOVERNMENT RIGHTS CLAUSE

The research leading to the instant Application was supported by National Institutes of Health Grant No. RO1 AI16794. The Government may have certain rights in the invention.

FIELD OF THE INVENTION

The present invention relates to the identification of auxiliary genes that encode proteins involved in antibiotic resistance in bacteria, and to compounds that can antagonize the activity of such proteins, thereby resensitizing resistant bacteria to antibiotics.

BACKGROUND OF THE INVENTION

Clinical-Epidemiological Background

Methicillin resistant strains of *Staphylococcus aureus* (MRSA) have become first ranking nosocomial pathogens worldwide. These bacteria are responsible for over 40% of all hospital-born staphylococcal infections in large teaching hospitals in the US. Most recently they have become prevalent in smaller hospitals (20% incidence in hospitals with 200 to 500 beds), as well as in nursing homes (Wenzel et al., 1992, Am. J. Med. 91(Supp 3B):221–7). An unusual and most unfortunate property of MRSA strains is their ability to pick up additional resistance factors which suppress the susceptibility of these strains to other, chemotherapeutically useful antibiotics. Such multiresistant strains of bacteria are now prevalent all over the world and the most "advanced" forms of these pathogens carry resistance mechanisms to all but one (vancomycin) of the usable antibacterial agents (Blumberg et al., 1991, J. Inf. Disease (63:1279–85).

A most ominous and recent development is the appearance of a vancomycin resistance mechanism in another nosocomial pathogen—*Enterococcus faecium*—which is known for its ability to transfer from one cell to another plasmid-born resistance factors, such as vancomycin resistance. The arrival of vancomycin resistance to MRSA is only a matter of time. Once this happens, an invasive bacterial pathogen without any antibacterial agent to control it will result. This event would constitute nothing short of a potential public health disaster of immense proportion (Leclercg et al., 1988, New Eng. J. Med. 319:157–61).

The preceding explains the intense interest in the public health and pharmacological community in any new method that promises a usable intervention against MRSA. A more complete explanation of the basis for antibiotic resistance follows.

Molecular Basis of Antibiotic Resistance

The central genetic element of methicillin resistance is the so called mecA gene. This gene is found on a piece of DNA of unknown, non-staphylococcal origin that the ancestral MRSA cell(s) must have acquired from a foreign source. The mecA gene encodes for a penicillin binding protein (PBP) called PBP2A (Murakami and Tomasz, 1989, J. Bacteriol. 171:874–79), which has very low affinity for the entire family of beta lactam antibiotics. In the current view, PBP2A is a kind of "surrogate" cell wall synthesizing enzyme that can take over the vital task of cell wall synthesis in staphylococci when the normal complement of PBPs (the normal catalysts of wall synthesis) can no longer function because thy have become fully inactivated by beta lactam antibiotic in the environment. The critical nature of the mecA gene and its gene product PBP2A for the antibiotic resistant phenotype was best demonstrated by transposon inactivation experiments in which the transposon Tn551 was maneuvered into the mecA gene. The result was a dramatic drop in resistance level from the minimum inhibitory concentration (MIC) value of 1600 $\mu$g/ml in the parental bacterium to the low value of about 4 $\mu$g/ml in the transposon mutant (Matthews and Tomasz, 1990, Antimicrobial Agents and Chemotherapy 34:1777–9).

This observation is consistent with the foregoing theory. The mutant bacteria with their interrupted mecA gene could no longer synthesize PBP2A; thus the surrogate enzyme needed for the survival in the antibiotic-rich environment was no longer available to catalyze wall synthesis. Consequently, the methicillin susceptibility of the Tn551 mutant dropped to a level approaching the susceptibility of staphylococci without the mecA gene. Methicillin MIC for such bacteria is usually in the vicinity of 1–2 $\mu$g/ml.

Auxiliary genes

Additional genetic work resulted in several surprising observations. First it was found that the level of antibiotic resistance could also be dramatically lowered in transposon mutants in which the Tn551 did not interrupt the mecA gene or interfere with the expression of this gene (i.e., the production of PBP2A). Clearly, these mutants were low in resistance for some reason other than an interruption of the functioning of the mecA gene. In fact, it turned out that the great majority of Tn551 insertional mutants with reduced methicillin resistance all continued to produce normal amounts of PBP2A in spite of the fact that their resistance level could be reduced by very large factors, such as dropping from the methicillin MIC of 1600 $\mu$g/ml to a low of 3 $\mu$g/ml.

The first such mutant was isolated in 1983 by Swiss scientists at a time when the nature of methicillin resistance was hardly understood at all (Berger-Bächi, 1983, J. Bacteriol. 154:479–87). Subsequent work in several laboratories have increased the number of these genetic determinants, the common feature of which was that they had an intact mecA gene and yet they had reduced resistance levels to the beta lactam family of antibiotics. The provisional name "auxiliary genes" was proposed for this class of unusual genetic elements to imply that they appeared to perform some essential "helper" function(s) in the expression of high level beta lactam resistance (Tomasz, 1990, In *Molecular Biology of the Staphylococci*, Novick and Skurray, Eds., VHC Publishers: New York, pp. 565–583).

A second surprising observation concerned the number of auxiliary genes that have been identified. By 1993, the number of genetically distinct auxiliary mutants described in the literature had risen to four.

A third set of observations provided clues as to the biochemical nature of auxiliary functions. It was shown by a newly developed high resolution chromatography technique that many of the auxiliary mutants produced abnormal peptidoglycan in their cell walls. Studies combining High Performance Liquid Chromatography (HPLC) and mass spectrometry allowed the identification of the chemical changes that occurred in the mutants (De Jonge et al., 1991, J. Bacteriol. 173:1105–10; De Jonge et al., 1992, J. Biol. Chem. 267:11248–54; De Jonge et al., 1992, J. Biol. Chem 267:11255–9; and De Jonge et al., 1993, J. Bacteriol. 175:2779–82). The cell wall peptidoglycan of auxiliary mutants was composed of muropeptides (cell wall building blocks) either with incomplete cross-linking peptides or containing a free glutamic acid residue instead of the usual isoglutamine. Still other mutants showed different cell wall muropeptide fingerprints in which the exact nature of changes remains to be elucidated. These findings suggest that the auxiliary genes are genes involved with the biosynthesis of cell wall precursor muropeptides.

While all the numerous auxiliary mutants share the common feature of carrying an intact mecA, each one of the auxiliary genes are unique by the criteria of (i) physical location on the chromosome as determined by restriction mapping; (ii) in the several cases in which DNA sequences of the genes were determined (as in the cases of the auxiliary genes known as femA, femB and femC) (Berger-Bächi et al., 1992, Antimicrobial Agents and Chemotherapy 36:1367–73; Gustafson et al., 1993, In *Abstracts of the 93rd General Meeting of the American Society for Microbiology*, Abstract A-97, p. 18; and De Lencastre et al., 1993, "Molecular Aspects of Methicillin resistance in *Staphylococcus aureus*", J. Antimicrob. Chemother. 33:), the genes were shown to have unique DNA sequences; and (iii) in the cases in which the mutants had altered cell wall composition, the HPLC patterns provided additional gene-specific fingerprints characteristic of the particular mutant.

Various references are cited in the Description of the Drawings and the Examples by number. A complete citation for each of such references is found at the end of the specification, after the Examples, and before the claims.

The citation of any reference herein is not an admission that such reference is available as prior art to the instant invention.

SUMMARY OF THE INVENTION

The present invention is broadly directed to the identification of auxiliary genes encoding proteins associated with antibiotic resistance in bacteria, in particular Gram positive bacteria, to characterizing the phenotype of bacteria having mutated auxiliary genes, and to identifying compounds that can mimic the phenotype of bacteria in which the activity of the auxiliary gene is disrupted.

In a preferred aspect, the invention is directed to a mutant antibiotic-resistant *Staphylococcus aureus* strain characterized by increased sensitivity to an antibiotic to which a parent of the mutant strain is resistant, and location of the mutation in a SmaI-A, B, C, D, E, F or I fragment of the chromosome of *S. aureus*. Generally, the antibiotic is a beta lactam antibiotic, in particular, methicillin. In a preferred aspect, the mutation is caused by insertion of transposon Tn551.

The present invention particularly relates to mutations in a SmaI-B fragment of the *S. aureus* chromosome.

In a preferred aspect, the mutation occurs in an auxiliary gene and yields a bacterial phenotype with greatly increased sensitivity to methicillin, e.g., a reduction of from 1600 to 25–50 μg/ml sensitivity. In a specific embodiment, the mutation is to a gene having a high degree of similarity to the murE gene of *Bacillus subtilis Haemophylus influenzae* and *E. coli*.

In a specific embodiment, the mutant antibiotic-resistant *S. aureus* is strain RUSA235.

The invention is further directed to a DNA molecule comprising a nucleic acid sequence which encodes a protein associated with antibiotic resistance in a *S. aureus* bacterium, which nucleic acid sequence is preferably located in the SmaI-B fragment of the chromosome of the *S. aureus* bacterium. In preferred embodiments of the invention, the gene is mutated in mutant strain RUSA235. In a specific embodiment, the gene has a sequence as depicted in FIGS. 13A–F.

The invention is also directed to a recombinant vector comprising the DNA molecule described above, operatively associated with an expression control sequence, and to a bacterial cell comprising the recombinant vector.

In another aspect, the invention is directed to a method for identifying a compound useful for sensitizing bacteria to an antibiotic to which the bacterium is resistant, comprising identifying a compound that antagonizes the activity of a protein associated with antibiotic resistance in a *S. aureus* bacterium, which protein is preferably encoded by a nucleic acid sequence located in the SmaI-B fragment of the chromosome of the *S. aureus* bacterium. Preferably, the protein is highly similar to the murE gene product.

In one aspect of the invention, the composition and structure of the bacterial cell wall can be analyzed by high performance liquid chromatography and mass spectrometry to determine the association of the protein with muropeptide precursor synthesis. In a specific embodiment, the invention relates to identification of a compound the administration of which results in lack of unsubstituted pentapeptide in the bacterial cell wall, incorporation of alanylglutamate- and alanylisoglutamine-containing muropeptides, and accumulation of large amounts of the UDP-linked muramyul dipeptide in the cytoplasmic wall precursor pool of the mutant bacteria.

In a specific embodiment, the invention contemplates reducing beta lactam antibiotic resistance in bacteria by administration of a competitive inhibitor antagonist of an enzyme or enzymes involved with addition of lysine to the dipeptide alanylisoglutamine and alanylglutamate, such as analogs of isoglutamine, analogs of glutamic acid, analogs of UDP-N-acetylmuramylalanylglutamate, and analogs of lysine.

In yet another aspect, the invention relates to a method for treating a subject suspected of having a bacterial infection comprising administering to the subject an amount of a compound useful for sensitizing the bacteria to an antibiotic to which the bacterium is resistant in conjunction with an amount of the antibiotic sufficient to neutralize the bacteria. In one embodiment, the compound inhibits or antagonizes the activity of a protein associated with muropeptide precursor synthesis, in particular the addition of the third residue in the synthesis of the muropeptide precursor.

Although not intending to be bound by any particular mechanistic theory or hypothesis, the inventors believe that in the presence of a beta lactam antibiotic the drug molecules and molecules of the cell wall building blocks (muropeptides) compete for the active site of PBP2A, i.e., the surrogate enzyme that, under these conditions, is solely responsible for cell wall biosynthesis. Intact, functioning auxiliary genes allow the production of all the normal cell wall precursor muropeptides, which are highly effective in the competition for the enzyme active site. Thus, in such a staphylococcal cell, relatively higher concentration of the antibiotic is needed for the inactivation of PBP2A, driving the antibiotic MIC value up.

In contrast, inactivated auxiliary genes may prevent the formation of structurally normal cell wall precursors in appropriate intracellular concentrations. Such structurally abnormal—or concentration-wise inadequate—cell wall precursors do not have high enough affinity for the active site of PBP2A. Thus, the relative effectiveness of the drug molecules increases, driving the MIC value down. However, the identification of strains mutated in auxiliary genes which do not appear to be directly associated with muropeptides precursor synthesis suggests that there are interacting cellular pathways involved in antibiotic resistance.

It is a particular advantage of the invention that the compounds of the invention make possible the use of the known battery of antibiotics, rather than requiring development of new antibiotics, for the treatment of bacterial infections.

The primary object of the invention is to identify compounds that reverse antibiotic resistance in bacteria. These compounds can be used in conjunction with the antibiotics to treat bacterial infections not otherwise amenable to chemotherapy.

Thus, it is an object of the present invention to identify auxiliary genes encoding proteins directly or indirectly associated with antibiotic resistance in bacteria.

It is also an object of the invention to identify such auxiliary genes that encode proteins involved with cell wall precursor synthesis.

Yet another object of the invention is to isolate, sequence and characterize such genes, in order to evaluate the functional activity of the protein encoded by the gene.

It is yet a further object to prepare such proteins in purified form for structural and functional analysis.

Most importantly, it is an object of the invention to screen for and select compounds that reverse antibiotic resistance of bacteria.

These and further objects of the invention will become more clear after consideration of the following FIGURES and DETAILED DESCRIPTION.

BRIEF DESCRIPTION OF THE DRAWINGS

FIGS. 1a and 1b. Proposed model for competition for the active site of penicillin binding protein (PBP) 2A by cell wall precursor muropeptides and antibiotic. Structurally normal precursors are effective competitors driving the methicillin MIC value up. (B). Precursors with abnormal chemical structure, produced in auxiliary mutants, are ineffective competitors with methicillin, resulting in reduced MIC value (and abnormal cell wall composition). The invention is not intended to be limited by this model, which is offered by way of explanation and not limitation.

FIGS. 13A–F. Nucleotide sequence of the 5.757 bp XbaI/HpaI fragment (SEQ. ID NO:1). Numbering starts at the XbaI site and ends at the HpaI in the 5752 nt position. The predicted primary structure of the polypeptides encoded by ypfP (ORF1), murE (ORF2) and prfC (ORF3) are given in single-letter code. The putative start codons are indicated after the gene designation, and the stop codons are designed by asterisk. The possible candidates for promotor sequences –35 and –10 regions are shown like the putative ribosome binding sites (rsb) in bold above the nucleotide sequence. The Tn551 insertion site is shown.

FIGS. 14A–B. Alignment of the predicted product of murE of Staphylococcus aureus (sa) with identical proteins of others species (bs) Bacillus subtilis; (hi) Haemophylus influenzae; (ec) Escherichia coli; (pa) Pseudomonas aeruginosa. Four consensus regions are indicated. The alignments were determined by using the PileUp program of the GCG package, and the Prettybox program of the extension EGCG package of sequence analysis software. The black boxes indicate identical residues and highlighting in gray indicate conservative replacements.

FIGS. 15A–B. Alignment of the predict product of RF3 of Staphylococcus aureus (sa) with identical proteins of others species, (bn) Dichelobacter (Bacteroides) nodosus; (hi) Haemophylus influenzae; and (ec) Escherichia coli. The consensus region of GTP-binding domain is indicated. The alignments were determined as in the legend of FIGS. 14A–B.

FIGS. 16A–B. Alignment of the predict product of YpfP of Staphylococcus aureus (sa) with the identical protein of (bs) B. subtilis, the MurG proteins of the (bs) B. subtilis, (ef) Enterococcus faecalis and the MGDG synthetase of (cs) Cucumis sativus. The alignments were determined as in the legend of FIGS. 14A–B.

DETAILED DESCRIPTION OF THE INVENTION

Figure 1B:
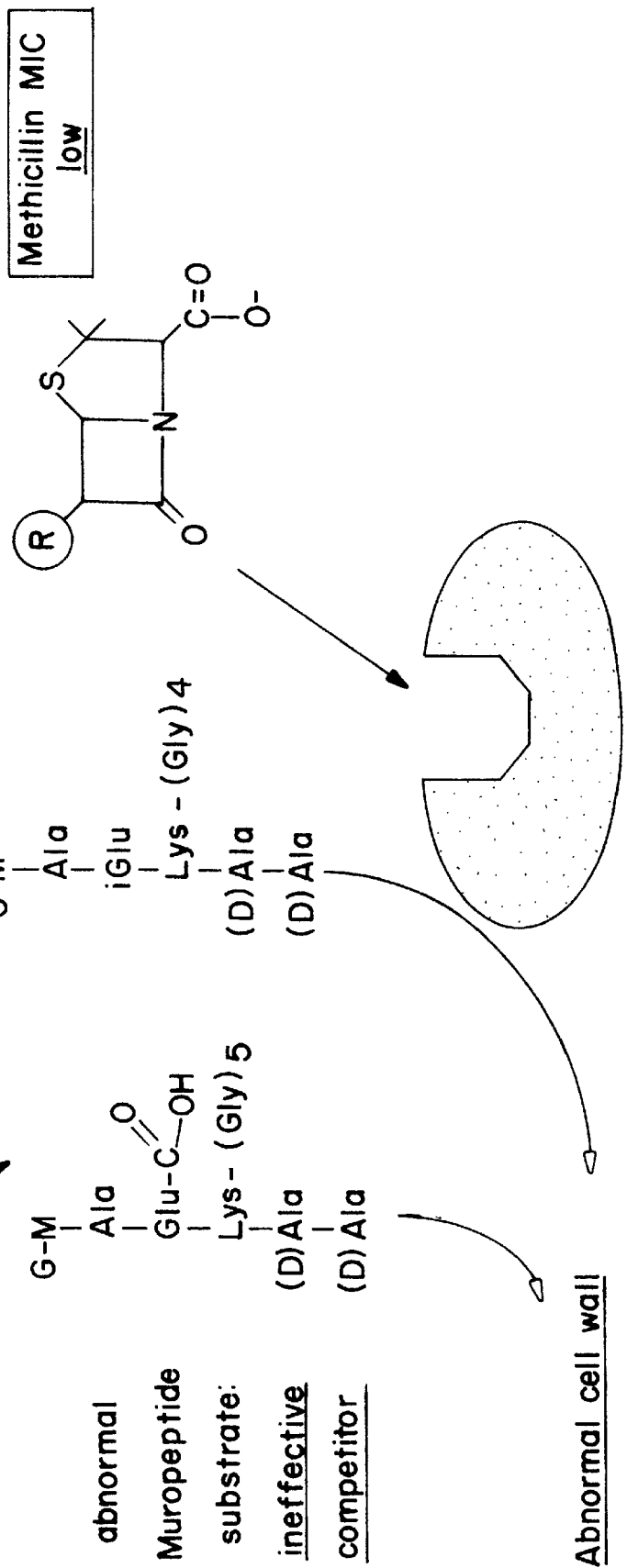

In accordance with the present invention there may be employed conventional molecular biology, microbiology, and recombinant DNA techniques within the skill of the art. Such techniques are explained fully in the literature. See, e.g., Sambrook, Fritsch and Maniatis, "Molecular Cloning: A Laboratory Manual," Second Edition (1989) Cold Spring Harbor Laboratory Press, Cold Spring Harbor, N.Y. (herein "Sambrook et al., 1989"); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R.I. Freshney, ed. (1986)]; "Immobilized Cells And Enzymes" [IRL Press, (1986)]; B. Perbal, "A Practical Guide To Molecular Cloning" (1984). Each of these references is specifically incorporated herein by reference.

Therefore, if appearing herein, the following terms shall have the definitions set out below.

A "replicon" is any genetic element (e.g., plasmid, chromosome, virus) that functions as an autonomous unit of DNA replication in vivo, i.e., capable of replication under its own control.

A "vector" is a replicon, such as plasmid, phage or cosmid, to which another DNA segment may be attached so as to bring about the replication of the attached segment.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid.

A "clone" is a population of cells derived from a single cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA—DNA, DNA-RNA and RNA—RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., 1989, supra). The conditions of temperature and ionic strength determine the "stringency" of the hybridization. For preliminary screening for homologous nucleic acids, low stringency hybridization conditions, corresponding to a $T_m$ of 55°, can be used, e.g., 5× SSC, 0.1% SDS, 0.25% milk, and no formamide; or 30% formamide, 5× SSC, 0.5% SDS). Moderate stringency hybridization conditions correspond to a higher $T_m$, e.g., 40% formamide, with 5× or 6× SSC. High stringency hybridization conditions correspond to the highest $T_m$, e.g., 50% formamide, 5× or 6× SSC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–0.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 10 nucleotides; preferably at least about 15 nucleotides; and more preferably the length is at least about 20 nucleotides; and most preferably 30 nucleotides.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then translated into the protein encoded by the coding sequence.

An "antisense nucleic acid" is a single stranded nucleic acid molecule which, on hybridizing with complementary bases in an RNA or DNA molecule, inhibits the latter's role. If the RNA is a messenger RNA transcript, the antisense nucleic acid is a countertranscript or mRNA-interfering complementary nucleic acid. As presently used, "antisense" broadly includes RNA—RNA interactions, RNA-DNA interactions, ribozymes and RNase-H mediated arrest. Antisense nucleic acid molecules can be encoded by a recombinant gene for expression in a microorganism, or alternatively they can be prepared synthetically.

A composition comprising "A" (where "A" is a single protein, DNA molecule, vector, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least 90% by weight of the A+B species in the composition, most preferably at least 99% by weight. It is also preferred that a composition, which is substantially free of contamination, contains only a single molecular weight species having the activity or characteristic of the species of interest.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions.

In its primary specific aspect, the present invention relates to two new *S. aureus* mutants, in which the methicillin MIC value of the paternal MRSA strain COL (MIC 1600 μg/ml) is reduced to between 200 μg/ml and 1.5 μg/ml. Surprisingly, some of these mutations are located on the chromosomal fragments SmaI-B generated by the restriction nuclease SmaI. Other mutations have been found on SmaI-C, D, E, and F, and novel mutations on SmaI-A and I. No auxiliary genes have ever been located to SmaI-B, C, D, E, and F fragments. The mutants are distinct by physical mapping using restriction endonucleases, such as but not limited to PstI, EcoRI, EcoRV, and HindIII. The mutants are valuable; for example, one (RUSA235) causes abnormal cell wall composition.

The invention more generally relates to mutants with mutations to auxiliary genes found in loci in addition to the SmaI-B fragment locus, such as on SmaI-A, C, D, E, F, and I chromosomal fragments.

The invention relates generally to auxiliary genes and proteins found in loci in addition to the *S. aureus* Sma-B locus. For example, a number of distinct genetic loci involved with the optimal expression of methicillin resistance, including at least fifty-eight distinct loci, found on chromosomal fragments, such as SmaI-B, C, D, E, F and I fragments.

In particular, the invention relates to identification of a gene with a high degree of sequence similarity to a murE gene, e.g., *B. subtilis* murE gene.

Identification of Genetic Determinants of Methicillin Resistance

In order to identify the genetic determinants that contribute to the antibiotic, e.g., methicillin, resistance phenotype, mutations can be generated in the isogeneic background of a highly resistant strain. For example, staphylococcal strain COL, a homogeneously and highly methicillin resistant clinical isolated (MIC for methicillin: 1600 mg/L), which is susceptible to erythromycin, can be used as the common parent for all the mutants. In a preferred aspect of the invention, transposon mutagenesis can be used to generate mutants. Alternatively, any random mutagenesis technique known in the art, such as but not limited to chemical mutagenesis, e.g., treatment with alkylating agents, base analogs bisulfate, hydroxylamine, intercalating agents, and the like; radiation; hyperthermia; etc., can be used to develop mutants to identify such genetic determinants.

In a specific preferred embodiment, which is the best mode contemplated by the inventors for identifying auxiliary genes in MRSA, a plasmid carrying transposon Tn551 and a thermosensitive replicator (pRN3208) (Novick, 1974, Mol. Gen. Genetics 135:131–47) can be introduced into COL (Kornblum et al., 1986, Eur. J. Clin. Microbiol. 5:714–8). The plasmid has several heavy metal resistance genes (Cd; Hg; As), the β-lactamase gene and the genetic determinant of erythromycin resistance, the latter being part of the Tn551 transposon. Upon shifting the temperature of the growth medium from 30° C. to 43° C., replication of the plasmid ceases (because of the thermosensitivity of plasmid replication); β-lactamase production and resistance of bacteria to heavy metals is lost along with the plasmid, but a small fraction of the population ($10^{-5}$) retains resistance to erythromycin. This erythromycin resistant group represents Tn551 insertional mutants, i.e., cells in which the Tn551 transposon is rescued by "hopping" from the plasmid into a variety of sites on the staphylococcal chromosome. Insertion of Tn551 is expected to occur more or less randomly, resulting in the inactivation of chromosomal function(s) at the insertion sites, and these inactivated functions may then be identified by appropriate secondary screens (Pattee, 1981, J. Bacteriol., 145:479–88).

In particular, Tn551 mutants of strain COL can be tested for colonies with decreased methicillin resistance. Independent mutant isolates are examined for their methicillin resistance phenotypes. Liquid cultures of the mutants are plated at various cell concentrations on agar plates containing serial dilutions of methicillin.

This method, known as population analysis, allows a quantitative description of the antibiotic resistance phenotypes of bacterial cultures in terms of population analysis profiles (PAPs) (de Lencastre et al., 1991, Antimicrobial Agents and Chemotherapy, 35:632–9).

Tn551 insertions can produce profound and unique effects in the expression of methicillin resistance. For example, when the Tn551 is within the mecA gene, the MIC drops from 1600 to 3 mg/L. Cultures of the mutants may demonstrate reduced levels of resistance in the majority of the cells, but the cultures also can become heterogeneous; they may contain subpopulations of cells with dramatically higher resistance levels and with frequencies characteristic of the particular mutant. Conversion of the homogeneous resistance of the parental strain COL to a variety of heterogeneous phenotypes is striking since most clinical isolates are known to have similar heterogeneous PAPs (Tomasz et al., Antimicrobial. Agents and Chemotherapy, 35:124–9).

Transposon mutagenesis can cause chromosomal rearrangements, which may make the interpretation of the Tn551 induced phenotypes difficult. In order to exclude the possibility that a chromosomal rearrangement, and not insertion of Tn551 into a gene, is responsible for observed PAP changes, the mutants can be back-crossed into the original parent strain COL, either by genetic transformation (using DNA prepared from the resistant mutants) or by transduction with phage 80α. After selection for erythromycin resistance (10 mg/L), the transformants can be analyzed for their methicillin resistance. In these crosses the Tn551 inactivated (nonfunctional) gene is expected to replace, by homologous recombination, the corresponding functional gene(s) of COL, recreating the phenotypes of the DNA donor mutant bacteria. Transformants/transductants that have co-transferred with the Tn551 marker the reduced methicillin resistance represent mutants rather than Tn551-induced chromosomal rearrangements.

This technique can yield mutant phenotypes that represent inactivation of a set distinct genetic elements essential for the expression of high level, homogeneous resistance to methicillin.

Chromosomal Location of Methicillin Resistance Auxiliary Genes

The staphylococcal chromosome can be cut into approximately 16 fragments by using the infrequently cutting restriction endonuclease SmaI, and the physical arrangement of these DNA fragments along a circular structure has been established (Pattee et al., In *Molecular Biology of the Staphylococci*, 1990, Novick and Skurray, Eds., VCH Publishers; New York, pp. 41–58). Chromosomal DNA from independent Tn551 mutants and from the parent strain COL can be treated with SmaI, and the fragments separated by pulsed field gel electrophoresis. After visualization of the fragment pattern, the DNA fragments can be transferred to nitrocellulose membranes and hybridized with a radiolabeled probe of Tn551. DNA fragments containing the Tn551 light up in the autoradiogram and reveal the location of genetic determinants that are needed for the optimal expression of methicillin resistance.

In a specific embodiment, the auxiliary gene of interest is located in fragment B. No auxiliary gene has previously been identified in fragment B. In a more specific embodiment, the auxiliary gene of interest is the gene mutated in mutant strain RUSA235.

Chromosomal location can be further resolved after digestion with other restriction enzymes, such as EcoRI, PstI, EcoRV, and HindIII followed by probing with Tn551. For example, the restriction nuclease HindIII cuts the Tn551 transposon at two asymmetrical sites and thereby generates three bands on hybridization.

Mutations to auxiliary genes can be distinguished from mutations to the mecA gene itself. For example, the SmaI fragments and subfragments can be probed to determined if mutation, in particular, Tn551 insertion, has occurred within mecA, as previously characterized (Murakami and Tomasz, 1989, J. Bacteriol., 171:874–79; Matthews and Tomasz, 1990, Antimicrobial Agents and Chemotherapy, 34:1777–9).

Thus, according to the present invention, mutants can be identified for which the reduction of resistance level is due to the inactivation of "auxiliary genes" (Tomasz, 1990, In *Molecular Biology of Staphylococci*, Novick and Skurray, Eds., VCH Publishes; New York, pp. 565–83), genes that "help" to optimize the resistance phenotype for the bacteria.

The auxiliary genes may be present on the normal bacterial, e.g., staphylococcal, chromosome. Alternatively, auxiliary genes may belong to the package of foreign DNA. In staphylococci, non-staphylococcal DNA may comprise up to 60 kB (Stewart and Rosenblum, 1981, Current Microbiol. 5:227–30; Beck et al., 1985, J. Bacteriol. 165:373–78; Matthews et al., 1990, In *Molecular Biology of the Staphylococci*, Novick and Skurray, Eds., VCH Publishers; New York, pp. 69–83).

Consistency of phenotypes and the stability of insertion sites in genetic crosses can demonstrate conclusively that the reduction of methicillin resistance levels and the distortion of the mode of expression of resistance in the auxiliary mutants is due to single Tn551 insertions at unique chromosomal sites within genes that are present on the normal staphylococcal chromosome.

Isolation, Cloning, Expression and Characterization of Auxiliary Genes

Any Gram positive bacterial cell potentially can serve as the nucleic acid source for the molecular cloning of an auxiliary gene. The nucleic acid sequences can be isolated from Streptococcus, Bacillus, Mycobacterium, Staphylococcus, Enterococcus, and other Gram positive bacterial sources, etc. In a specific embodiment, the auxiliary gene is found in staphylococci. The DNA may be obtained by standard procedures known in the art from cloned DNA (e.g., a DNA "library"), by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II). Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Various strategies known in the art can be employed for cloning auxiliary genes identified according to the invention, and the invention is not limited to any particular cloning strategy. In a preferred embodiment, the following basic strategy may be employed: (A) The Tn551 inactivated genes can be cloned in *E. coli*; (B) the cloned Tn551-carrying pieces of the chromosome can be used to find the active alleles in the parent bacterium, e.g., COL, chromosome; (C) the active alleles can be cloned into a shuttle-vector and assayed for the ability to complement, i.e., correct, the phenotype of the appropriate transposon mutant; and (D) the cloned gene or genes can be sequenced. In a further aspect of the invention, this strategy can be implemented as follows:

(A) Cloning the insertionally inactivated (Tn551) form of auxiliary genes.
  1. Digest the chromosomal DNA with different restriction enzymes, preferably selecting enzymes that cut once (or twice) inside Tn551, but that can be used for cloning in the plasmid to be used in the cloning, e.g., the pUC19 plasmid, or BLUESCRIPT. For example, the restriction endonuclease KpnI cuts Tn551 once and can be used with both vectors. The fragments are preferably separated by running in conventional electrophoresis. 2. Probe the fragments with the internal XbaI-HpaI fragment from Tn551 cloned into the plasmid pGEM-1 (plasmid pRT1, see Matthews and Tomasz, 1990, Antimicrob. Agents Chemother. 34:1777–79) to find positive fragments—there will be two if an enzyme that cuts Tn551 once is used. 3. Elute the appropriate fragment or fragments identified with the probe from the gel. 4. Ligate the fragment into an E. coli vector (e.g., pUC19) and transform using an appropriate strain of E. coli as the recipient. 5. Select transformed bacteria in plates containing X-gal and IPTG; colonies containing recombinant plasmids will be white under these conditions. 6. Select the white colonies containing the required chromosomal fragment by colony hybridization using a Tn551 probe, such as the XbaI-HpaI fragment. 7. Identify positive clones identified by probe hybridization and prepare plasmid DNA. 8. Check for the proper size insert in the plasmids. 9. Construct a physical map of the plasmid.

(B) Cloning of the active allele.
  1. Prepare a probe from the plasmid carrying part of the Tn551 inactivated gene, i.e., vector+staphylococcus DNA insert+one end of Tn551. 2. Cut the chromosome of the parent strain, e.g., COL, with one of the enzymes used in cloning the fragment, which originates a Tn551-hybridizing fragment of approximately 10 kb. Probe with the plasmid fragment probe and find the positive band (corresponding to the active auxiliary gene. 3. Elute the band containing the chromosomal fragment identified with the probe, and ligate the eluted DNA into a shuttle vector, such as pGC2. 4. Transform E. coli by selecting for the intact plasmid vector marker AmpR. 5. Probe transformants by colony hybridization, e.g., with the plasmid fragment probe. 6. Prepare plasmids and run on a gel. Identify the plasmids which are of larger size than the vector alone; these plasmids should have a size corresponding to the vector+insert. 7. Construct a physical map of the plasmid and compare it with the physical map of the plasmid containing the inactivated gene.

(C) Complementation assay.
  1. The complementation assay involves the introduction of the recombinant plasmid putatively containing the inserted active allele of the auxiliary gene into the original aux mutant. The introduction of the recombinant vector can be attempted by electroporation (Luchansky et al., 1988, Mol. Microbio. 2:637–646), protoplast transformation (Chang and Cohen, 1979, Mol. Gen. Genet. 168:111–115), or prophage transformation (Pattee and Nevelin, 1975, J. Bacteriol. 124:201–211). The selection should be first for a plasmid marker, such as CmR (a plasmid pCG2 marker that is expressed in S. aureus), and then for methicillin resistance. If the complementation has worked fully, the phenotype of the transposon mutant carrying the shuttle vector with the aux gene should be the same as that of the original parent strain.

The step of cutting the chromosome of the parent strain can be simplified as follows: one class of mutants (located on the SmaI-A fragment) lie in the largest EcoRI fragment, of approximately 40 kb. This fragment can be easily resolved by PFGE electrophoresis from the other EcoRI fragments and eluted pure from the gel. The DNA of this 40 kb EcoRI fragment can then be cut with an appropriate restriction endonuclease as described in step B. 2. The same simplification method can be applied to clone auxiliary genes that lie in the SmaI fragment I, and that lie in the largest HindIII fragment.

Generally, once the DNA fragments are generated, identification of the specific DNA fragment containing the desired auxiliary gene may be accomplished in a number of ways. For example, if an amount of a portion of an auxiliary gene or a fragment thereof is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). Those DNA fragments with substantial homology to the probe will hybridize. The present invention provides specific examples of DNA fragments that can be used as hybridization probes for auxiliary genes, i.e., Tn551 mutants.

It is also possible to identify the appropriate fragment by restriction enzyme digestion(s) and comparison of fragment sizes with those expected according to a known restriction map if such is available. Further selection can be carried out on the basis of the properties of the gene.

As described above, the presence of the gene may be detected by assays based on the physical, chemical, or immunological properties of its expressed product. For example DNA clones that produce a protein that, e.g., has similar or identical electrophoretic migration, isoelectric focusing behavior, proteolytic digestion maps, proteolytic activity, antigenic properties, or functional properties, especially cell wall synthetic activity, known for a particular auxiliary protein. In particular, DNA suspected of containing the auxiliary gene of interest can be introduced into a mutant bacterial strain, e.g., RUSA235 to reconstitute normal phenotypic methicillin resistance, cell wall synthesis, and the like.

Alternatives to isolating the auxiliary genomic DNA include, but are not limited to, chemically synthesizing the gene sequence itself from a known sequence. For example, DNA cloning of an auxiliary gene can be isolated from Gram positive bacteria by PCR. Other methods are possible and within the scope of the invention.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. For example, the auxiliary coding sequence can be inserted in an E. coli cloning vector. Other examples of vectors include, but are not limited to, bacteriophages such as lambda derivatives, or plasmids such as pBR322 derivatives or pUC plasmid derivatives, e.g., pGEX vectors, pmal-c, pFLAG, etc.

The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shot gun" approach. Enrichment for the desired gene, for example, by size fractionation, can be done before insertion into the cloning vector.

Alternatives to isolating the auxiliary genomic DNA include, but are not limited to, chemically synthesizing the gene sequence itself from a know sequence. For example, DNA cloning of an auxiliary gene can be isolated from Gram positive bacteria by PCR. Other methods are possible and within the scope of the invention.

In specific embodiments, transformation of host cells with recombinant DNA molecules that incorporate the isolated auxiliary gene or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

The present invention also relates to vectors containing genes encoding analogs and derivatives of auxiliary proteins that have the same functional activity as an auxiliary proteins. The production and use of derivatives and analogs related to an auxiliary protein are within the scope of the present invention. In a specific embodiment, the derivative or analog is functionally active, i.e., capable of exhibiting one or more functional activities associated with a full-length, wild-type auxiliary protein.

In particular, derivatives can be made by altering encoding nucleic acid sequences by substitutions, additions or deletions that provide for functionally equivalent molecules. Due to the degeneracy of nucleotide coding sequences, other DNA sequences which encode substantially the same amino acid sequence as an auxiliary gene may be used in the practice of the present invention. These include but are not limited to nucleotide sequences comprising all or portions of auxiliary genes that are altered by the substitution of different codons that encode the same amino acid residue within the sequence, thus producing a silent change. Likewise, the derivatives of the invention include, but are not limited to, those containing, as a primary amino acid sequence, all or part of the amino acid sequence of an auxiliary protein including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

The genes encoding auxiliary protein derivatives and analogs of the invention can be produced by various methods known in the art. The manipulations which result in their production can occur at the gene or protein level. For example, a cloned auxiliary gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of an auxiliary protein, care should be taken to ensure that the modified gene remains within the same translational reading frame as the auxiliary gene, uninterrupted by translational stop signals, in the gene region where the desired activity is encoded.

Additionally, the auxiliary gene nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479–488; Oliphant et al., 1986, Gene 44:177; Hutchinson et al., 1986, Proc. Natl. Acad. Sci. U.S.A. 83:710), use of TAB® linkers (Pharmacia), etc. PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61–70).

Once the gene is cloned, its sequence can be determined using any of the sequencing techniques known in the art.

Moreover, if desired, the gene can be expressed recombinantly, using the well known techniques for recombinant gene expression, in order to obtain a large sample of purified protein for structural and functional studies.

The gene coding for an auxiliary protein, or a functionally active fragment or other derivative thereof, can be inserted into an appropriate expression vector, i.e., a vector which contains the necessary elements for the transcription and translation of the inserted protein-coding sequence. An expression vector also preferably includes a replication origin. The necessary transcriptional and translational signals can also be supplied by the native auxiliary gene and/or its flanking regions. A variety of host-vector systems may be utilized to express the protein-coding sequence. Preferably, however, a bacterial expression system is used to provide for high level expression of the protein with a higher probability of the native conformation. Potential host-vector systems include but are not limited to bacteria transformed with bacteriophage, DNA, plasmid DNA, or cosmid DNA.

The expression elements of vectors vary in their strengths and specificities. Depending on the host-vector system utilized, any one of a number of suitable transcription and translation elements may be used.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination).

Expression of nucleic acid sequence encoding an auxiliary protein or peptide fragment may be regulated by a second nucleic acid sequence so that the exported protein or peptide is expressed in a host transformed with the recombinant DNA molecule. For example, expression of an auxiliary protein may be controlled by any promoter/enhancer element known in the art, but these regulatory elements must be functional in the host selected for expression. For expression in bacteria, bacterial promoters are required ("Useful proteins from recombinant bacteria" in Scientific American, 1980, 242:74–94).

Expression vectors containing auxiliary gene inserts can be identified by four general approaches: (a) PCR amplification of the desired plasmid DNA or specific mRNA, (b) nucleic acid hybridization, (c) presence or absence of "marker" gene functions, and (d) expression of inserted sequences. In the first approach, the nucleic acids can be amplified by PCR with incorporation of radionucleotides or stained with ethidium bromide to provide for detection of the amplified product. In the second approach, the presence of a foreign gene inserted in an expression vector can be detected by nucleic acid hybridization using probes comprising sequences that are homologous to an inserted gene. In the third approach, the recombinant vector/host system can be identified and selected based upon the presence or absence of certain "marker" gene functions (e.g., β-galactosidase activity, PhoA activity, thymidine kinase activity, resistance to antibiotics, transformation phenotype, occlusion body formation in baculovirus, etc.) caused by the insertion of foreign genes in the vector. If the auxiliary gene is inserted within the marker gene sequence of the vector, recombinants containing the insert can be identified by the absence of the marker gene function. In the fourth approach, recombinant expression vectors can be identified by assaying for the activity of the gene product expressed by the recombinant. Such assays can be based, for example, on the physical or functional properties of the auxiliary gene product in suitable assay systems, e.g., cell wall synthesis.

Once a suitable host system and growth conditions are established, recombinant expression vectors can be propagated and prepared in quantity.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered auxiliary protein may be controlled. Furthermore, different host cells have characteristic and specific mechanisms for the translational and post-translational processing and modification (e.g., cleavage of signal sequence) of proteins. Appropriate cell lines or host systems can be chosen to ensure the desired modification and processing of the foreign protein expressed. Different vector/host expression systems may affect processing reactions, such as proteolytic cleavages, to a different extent.

Biochemical Activity of Auxiliary Proteins

Generally, the invention provides for identification of a functional property of a protein produced by an auxiliary gene by comparing the homology of the deduced amino acid or nucleotide sequence to the amino acid sequence of a known protein, or the nucleotide sequence of the gene encoding the protein.

An important aspect of the invention is ability to characterize the biochemical activity of the protein encoded by the auxiliary gene, particularly the auxiliary genes of mutant RUSA235, by biochemical and phenotypic analysis. Information about the biochemical activity of the protein provides direction for identifying antagonists, as described below.

Transposon inactivation experiments indicate that the functioning of the mecA gene and auxiliary genes are both essential for the expression of high level methicillin resistance. Although not intending to be limited by any particular theory, a conceivable model would be as follows. As the β-lactam antibiotic level begins to increase in the environment of the bacteria, the antibiotic molecules penetrate the cell surface and inactivate (by covalent bond formation) the normal complement of the four staphylococcal PBPs which have relatively high affinities for the drug molecules. In vitro experiments indicate that within the methicillin concentration range of 5 to 10 mg/L, all four "normal" PBPs become fully acylated. One may assume that under these conditions, perhaps upon the generation of a cellular signal, the low affinity PBP2A takes over the task of cell wall synthesis. It was shown that in the highly resistant strain COL (methicillin MIC=1600 mg/L), addition of 5–10 mg/L methicillin to the medium resulted in a striking change in the composition of peptidoglycan (de Jonge and Tomasz, 1993, Antimicrobial Agents and Chemotherapy, 37:342–6). In drug free medium, this bacterium produces a cell wall composed of a diverse family of over 35 muropeptide components, the majority (60%) of which are trimers or higher oligomers of muropeptides. When grown in the methicillin containing medium, this complex wall structure is replaced by a simple one in which the peptidoglycan is made up of essentially two components; the pentaglycyl monomer and its dimer, with only a very small amount of trimers and traces of higher oligomers. Bacteria continue to produce this simple peptidoglycan throughout a vast range of antibiotic concentrations in the medium for 5 mg/L (<0.1% of the MIC) up to 750 mg/L (½×the MIC). The observations suggest that at the critical concentration of about 5 mg/L methicillin, a new cell wall synthetic machinery, presumably PBP2A, takes over. In this model, PBP2A is assumed to be a peculiar transpeptidase which can only link two monomers together, but is incapable of generating the highly crosslinked oligomers which are the characteristic products of the normal wall synthetic machinery (de Jonge and Tomasz, 1993 supra). It may be that blocks in the synthesis of "normal" muropeptides (i.e., inactivation of auxiliary genes) can cause such striking reductions in the effectiveness of this resistance mechanism (i.e., decrease in the MIC from 1600 to 3 mg methicillin per liter) in spite of the presence of large amounts of PBP2A because effective functioning of PBP2A also requires an abundant supply of structurally correct cell wall building blocks. The correct building blocks may successfully compete with the methicillin molecules for the active site of PBP2A. Muropeptides of "incorrect" structure (e.g., less than five glycine units in the crosslinking peptides, or lack of amidation of the glutamic residues) compete less effectively with the antibiotic molecule, which translates to a decrease in the methicillin MIC value (see FIGS. 1A and B).

The role of auxiliary proteins in cell wall synthesis can be indirectly evaluated by analyzing the composition of the cell wall.

Figure 2:
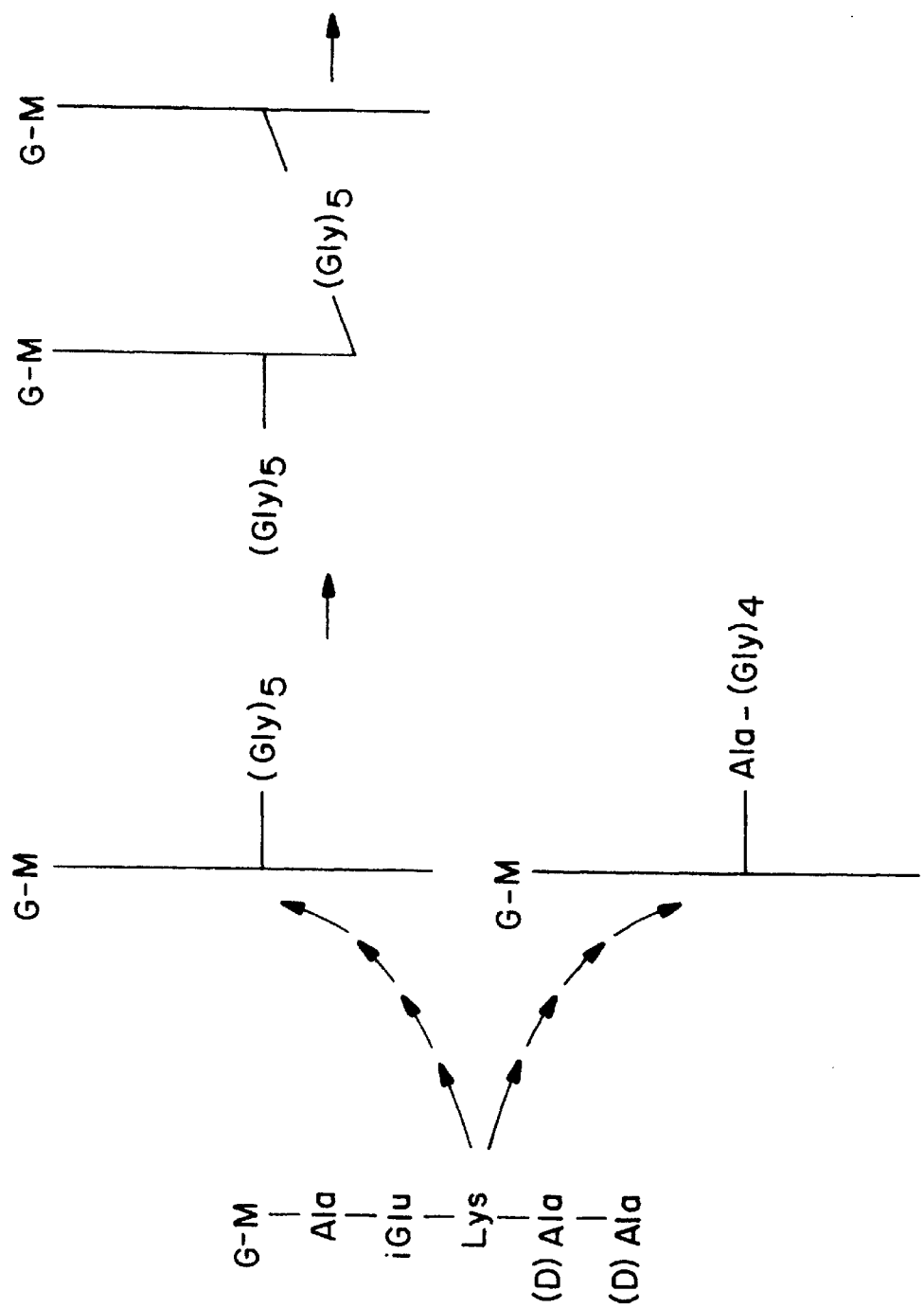
FIG. 2. Suggested pathway for the addition of crosslinking peptides to the pentapeptide precursors. Symbols: G—N-acetylglucosamine; M—N-acetylmuramic acid; Ala, iGlu, Lys—alanine, isoglutamine and lysis, respectively. The synthetic pathway is interrupted at various steps in the auxiliary mutants.

Cell wall peptidoglycan can be prepared from parental strains and from mutants. The muropeptide building blocks of the peptidoglycan (liberated by enzymatic digestion) can be separated by reverse phase high performance liquid chromatography (HPLC) (de Jonge et al., 1992, J. Biol. Chem. 267: 11248–54). Inactivation of the mecA gene causes no detectable change in muropeptide composition. Inactivation of auxiliary genes may cause major and unique composition changes in the peptidoglycans, which can be identified by differences in HPLC elution profiles of muropeptides isolated from enzymatic cell wall peptidoglycan hydrolysates of a parental strain and of mutants (See e.g., de Jonge et al., J. Bacteriol. 173:1105–10; de Jonge et al., 1992, J. Biol. Chem. 269:11255–9; Maidhof et al., 1991, J. Bacteriol. 173:3507–13; de Jonge et al., 1993, J. Bacteriol. 175:2779–82). These unique wall composition changes may be reproduced with precision. The results can indicate, e.g., that auxiliary genes control the biosynthesis of the oligopeptide substituent on the epsilon amino group of the lysine residue in the muropeptide stem in staphylococci (FIG. 2).

In a specific embodiment, infra, mutation to a staphylococcal auxiliary gene results in a partial block in the cytoplasmic peptidoglycan precursor synthesis of the pentapeptide at the addition of the third (lysine) residue. This block is reflected in the appearance of two new monomeric muropeptides in the cell wall of the mutant strain, and the presence of large amounts of a component in the precursor pool with retention time characteristic of a dipeptide. This component that builds up in the precursor pool is not present in parental cells.

In parental strains COL and M100, the most abundant monomer is the disaccharide pentapeptide substituted with a pentaglycyl unit on the epsilon amino group of the lysine residue, and this monomer is also the major building block of dimers, trimers and higher oligomers of the peptidoglycan.

Various muropeptide alterations may be observed. For example, synthetic blocks can occur at a step past addition of a fourth glycine; at a step past the addition of a first glycine; in the synthesis of minor muropeptides; in the synthesis of peptidoglycans; or in the amidation of the x-carboxyl group of the stem peptide glutamic acid residues (see de Lencastre et al., 1994 "Molecular Aspects of Methicillin Resistance in *Staphylococcus aureus*", J. Antimicrob. Chemother. 33; de Jonge et al., 1992, J. Biol. Chem. 267:11255–9; Ornelas-Soares et al., 1993, J. Biol. Chem. 268:26268–72).

Auxiliary Gene and Protein Antagonists

Although bacterial mutation can be used to identify genes associated with antibiotic resistance, random mutagenesis to knock out auxiliary genes is not a therapeutically attractive treatment regimen for bacterial, in particular, staphylococcal, infection. Thus, the present invention contemplates inactivation of auxiliary genes and proteins, in particular the mutant gene of the strain RUSA235, and protein encoded thereby, using compounds that antagonize the activity of the protein, or with antisense nucleic acids to inhibit expression of the protein.

In one embodiment, antisense nucleic acids that are complementary to the auxiliary gene mRNA can be administered to a subject suffering from a bacterial infection. Such nucleic acids can be DNA or RNA, preferably DNA, and more preferably DNA containing non-phosphate bonds, and thus is resistant to nuclease degradation in vivo.

As noted above, according to one non-binding theory of the invention, the suppression of antibiotic resistance by inactivation of these genes must be caused by the block in the production of the corresponding gene products that are essential for the phenotypic expression of resistance. Specific antagonists of these gene products can be screened for use as chemical agents capable of re-sensitizing the bacteria to beta lactam antibiotics.

One way for searching for such compounds would involve incorporating candidates into test systems containing appropriate concentrations of the beta lactam antibiotics and the test organisms, e.g., the highly methicillin resistant strain of *S. aureus*, strain COL. Effective compounds would be expected to reduce methicillin resistance at sub-inhibitory levels.

In another embodiment, screening for active compounds is based on observing similar or identical phenotypic changes in the antibiotic resistant bacteria, e.g., cell wall composition, accumulation of muramyl peptides, and the like, in the bacteria in the presence of a candidate inhibitor.

In a specific embodiment, the invention provides inhibitors of the step of addition of lysine to the muramyldipeptides alanylglutamate and alanalyisoglutamine. Such inhibitors may be selected from the group consisting of but not limited to analogs of isoglutamine, analogs of glutamic acid, analogs of UDP-N-acetylmuramylalanylglutamate, analogs of UDP-N-acetylmuramylalanylisoglutamine, and analogs of lysine. Such analogs are characterized by having the same topological structure, and therefore the same recognition features, as the natural precursors, but are modified to be non-reactive, thus competitively inhibiting the auxiliary gene product and thereby reducing methicillin resistance.

Any screening technique known in the art can be used to screen for suitable auxiliary protein antagonists. For example, bacterial phage or synthetic random libraries, e.g., preferably encoded synthetic libraries (Needels et al., 1993, "Generation and screening of an oligonucleotide encoded synthetic peptide library," Proc. Natl. Acad. Sci. USA 90:10700–4; Lam et al., International Patent Publication No. WO 92/00091, published Jan. 9, 1992) can be used.

The screening can be performed with bacteria, or alternatively, using purified protein, e.g., produced recombinantly, as described above.

Knowledge of the primary sequence of the protein, and the similarity of that sequence with proteins of known function, can provide an initial clue as the inhibitors or antagonists of the protein. Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of inhibitors and antagonists.

In a specific embodiment, a preliminary screen was performed in which several "early" cell wall inhibitors were shown to mimic the effect of auxiliary mutations when added to the methicillin containing medium at sub-inhibitory concentrations of D-cycloserine and fosfonomycin.

Treatment of Antibiotic Resistant Bacterial Infections

The present invention provides methods and compositions for the treatment of infections with antibiotic resistant or multiple antibiotic resistant bacteria. In its primary aspect, the invention provides for co-administration of a compound that inhibits or antagonizes an auxiliary protein involved in cell wall synthesis in conjunction with an antibiotic or antibiotics to which the bacterium is normally resistant.

Accordingly, the invention provides pharmaceutical compositions comprising a compound that antagonizes an auxiliary protein in an amount effective to antagonize the activity of an auxiliary protein, and a pharmaceutically acceptable carrier. In another embodiment, the pharmaceutical composition further comprises an antibiotic in an amount effective to treat a bacterial infection.

Preferably, the antibiotic is any member of the beta lactam family of antibiotics. In a specific aspect, the antibiotic is methicillin.

A particularly attractive feature of this strategy is that it does not involve the search for new antibiotic agents but rather it proposes to find agents that bring the target bacterium back to within the inhibitory range of well characterized antibiotics such as beta lactams.

This strategy is also applicable for the selection of agents that could resensitize bacteria to other types of antibiotics also. In addition, agents capable of sensitization to methicillin may very well be active in a similar manner in beta lactam resistant strains of other bacterial species such as *Enterococcus faecium* and *E. faecalis*, penicillin resistant pneumococci ($pen^R$ pneumococci), and coagulase-negative staphylococci.

According to the present invention, the therapeutic compositions and methods of the invention can be used to protect an animal subject from infection of a Gram positive bacteria. Thus, a therapeutic composition or method of the invention can be used in birds, such as chickens, turkeys, and pets; and in mammals, preferably humans, as well as other mammalian species, including but not limited to domesticated animals (canine and feline), farm animals (bovine, ovine, equine, caprine, porcine, and the like), rodents, and undomesticated animals.

The present invention will be better understood from a review of the following illustrative description.

EXAMPLE 1

Reassessment of the Number of Auxiliary Genes Essential for the Expression of High Level Methicillin Resistance in *Staphylococcus aureus*

A new transposon library constructed in the background of the highly and homogeneously methicillin resistant *Staphylococcus aureus* (MRSA) strain COL yielded 70 independent insertional mutants with reduced levels of antibiotic resistance. Southern hybridization with a Tn551 probe localized the inserts in 7 out of the 16 SmaI chromosomal fragments (fragments A, B, C, D, E, F, and I). Further restriction analysis with HindIII, EcoRV, EcoRI and PstI demonstrated that 58 of the 70 Tn551 mutants represented novel, as yet undescribed insertion sites. In all of the auxiliary mutants, expression of methicillin resistance became heterogeneous and the minimal inhibitory concentration (MIC) of the majority of cells was reduced to 1.5 $\mu$g up to 200 $\mu$g/ml from the homogeneous methicillin MIC of 1600 $\mu$g/ml in the parental cell. The findings indicate that a surprisingly large number of staphylococcal genes, in addition to mecA, are needed for the optimal expression of antibiotic resistance.

Materials and Methods

Strains and growth conditions.

The *S. aureus* reference strains used are listed in Table 1 and were grown as described before (18). Transposon mutants and their backcrosses were also grown as previously described (18).

Selection of Tn551 mutants.

The transposition experiment and selection of mutants was carried out by a modification of a previously described method (19). The parent strain COL harboring the thermosensitive plasmid pRN3208 carrying Tn551 with the erythromycin resistance determinant (referred to as COL [pRN3208]) was grown overnight at 30° C., and then diluted and plated at different cell concentrations on TSA (tryptic soy agar; Difco) containing 20 $\mu$g of erythromycin per ml. Plates were incubated at 30° C. and 43° C. for 48 hours. The approximate frequency of transposition (number of colonies at 43° C./number of colonies at 30° C.) was 2.1×10$^{-5}$. The erythromycin resistant colonies were checked for cadmium resistance (0.25 mM CdNO$_3$). The colonies that were cadmium resistant (indicating the integration of the whole plasmid) were grown on TSA at 43° C. for 16 hours to eliminate the plasmid, and tested again for cadmium resistance. Only colonies that were erythromycin resistant-cadmium sensitive were kept for further study. Each selected colony was grown on TSA containing 10 $\mu$g ml$^{-1}$ erythromycin and used to screen for decreased methicillin resistance.

Screening of mutants with decreased methicillin resistance.

The erythromycin resistant (ery$^R$) colonies were tested sequentially by three screens.

In the first screen, all ery$^R$ colonies were streaked on plates with erythromycin (10 $\mu$g ml$^{-1}$) and different concentrations of methicillin (0; 25; 50 and 400 $\mu$g ml$^{-1}$); three controls were used in the same plates—RUSA10, RUSA12F and COL (pRN3208). We identified as putative mutants all colonies that failed to grow in any of the media with methicillin, using COL (pRN3208) as the positive control.

In the second screen, the colonies identified in the previous screen as affected in resistance were grown overnight in 5 ml tryptic soy broth (TSB) with 10 $\mu$g ml$^{-1}$ erythromycin, and then tested on TSA plates containing a 1 mg methicillin disc. The controls referred to above were tested under the same conditions. After 24 hours of incubation at 37° C., the halos of inhibition were measured. The strains that gave inhibition halos larger that the ones of COL (pRN3208) were studied by a third screen.

In the third screen the colonies were analyzed by population analysis profiles (PAPs). We kept for further study the colonies that showed a PAP profile different from the one of COL (pRN3208): all the 70 selected mutants selected in this manner had MICs (minimal inhibitory concentration) lower than the one of the parent strain and all but two mutants also showed heterogeneous methicillin resistance phenotypes.

Population analysis profiles were performed as described (8) on plates containing methicillin (0, 1.5, 3, 6, 12.5, 25, 50, 100, 200, 400, and 800 $\mu$g/ml). Mutants were assigned to different expression classes according to a previous classification (Tomasz et al., 1991, Antimicrob. Agents Chemother. 35:124–129), with the addition of an intermediate class, class 2–3. The critical parameter for the assignment of a PAP to a particular class was the MIC for the majority of the cells, as follows: class 1, 1.5 to 3 $\mu$ml$^{-1}$; class 2, 6 to 12 $\mu$g l$^{-1}$; class 2–3, 25 to 50 $\mu$g ml$^{-1}$; class 3, 100 to 200 $\mu$g ml$^{-1}$; class 4, greater than 400 $\mu$g ml$^{-1}$; RUSA4 type (mecA::Tn155), 3 $\mu$g ml$^{-1}$. Strains of classes 1 to 3 are heterogeneous, whereas strains of class 4 or of the RUSA4 type are homogeneous.

Transduction crosses.

Transduction crosses using the newly isolated mutants as donors and the homogeneously resistant strain COL as recipient, were performed with phage 80 alpha, as described (18). The primary selection was for the transposon marker erythromycin (10 $\mu$g/ml). A total of 50 to 100 ery$^R$ transductants from each transduction were streaked onto TSA plates containing erythromycin (10 $\mu$g ml$^{-1}$) and erythromycin plus methicillin (10 $\mu$g/ml and 400 $\mu$g/ml, respectively) by using positive and negative controls COL (pRN3208) and the particular donor strain used in the cross, respectively. All erythromycin-resistant transductants were found to show reduced levels of methicillin resistance as well. From each cross, eight transductants were further tested for decreased levels of methicillin resistance by the 1-mg methicillin disc method, and two ro three transductants were also tested by PAP analysis for their antibiotic resistance phenotypes. The location of the insert was tested by comparing the HindIII hybridization patterns of transductants and their donors.

Conventional and pulsed-field gel electrophoresis.

Preparation of chromosomal DNA for conventional and pulsed-field gel electrophoresis (PFGE) was performed as previously published (10). Restriction digestions with SmaI, EcoRI, EcoRV, PstI and HindIII nucleases were carried out according to the manufacturer's recommendations. Conventional gel electrophoresis in 1% agarose in was carried out in 1× TAE buffer (21), for 16 h at 30–38 volts.

For pulsed-field gel electrophoresis, the gels were prepared with 1.1% agarose (SeaKem LE, FMC Bioproducts) in 0.5× TBE buffer as previously described (10). The gels were run in an LKB 2015 Pulsaphor System (Pharmacia) or in a Chef-DR II apparatus (Bio-Rad). The running conditions for the SmaI restriction digests were as previously described (10). Chromosomal fragments higher than 15 kb (which are difficult to separate by conventional gel electrophoresis) were run in a Chef-DR II apparatus (Bio-Rad, USA) for 23 h at 14° C. in the same buffer. The running conditions were as follows: the voltage was set at 200 V, ramped with initial forward time 0.5 sec, final forward time 1.5 sec.

DNA transfer.

For blotting of normal gels to nitrocellulose membranes (Schleicher & Schuell BA85, USA) a vacuum blotting apparatus was used (Vaccu-blot, Pharmacia/LKB) according to the manufacturer's instructions. For the blotting of pulsed-field gel electrophoresis gels we followed a previously described method (10).

Preparation of DNA probes and hybridization.

The whole plasmid pRT1 (that contains an internal fragment of the transposon Tn551) was used as probe. pRT1 contains a 4 kb HpaI-XbaI fragment from the transposon Tn551 cloned in the SmaI site of the plasmid pGEM. 1 (Promega). Standard methodology was followed for $^{32}P$ labeling of the probes by nick translation, prehybridization and hybridization (20). The hybridization was carried out at 42° C. in 50% formaldehyde. Nick translated plasmid DNA was denatured and added to hybridizations without separation of unincorporated nucleotides. When the membranes were rehybridized, the previous probe was removed by boiling in 0.1% SDS for 10 min. To ascertain the location of insertions the femA-femB region plasmids pGC42 and pBBB31 containing the 2.2 EcoRV and a 10.5 kb PstI fragment, respectively, were used (2).

Physical characterization of the mutants with EcoRI, PstI, EcoRV, and HindIII by probing with the Tn551 probe.

The enzymes EcoRI, PstI, and EcoRV have no restriction sites in Tn551, whereas the enzyme HindIII has two recognition sites (21), both of which are included in the probe used. The sizes of the DNA fragment generated after restriction enzyme digestion with EcoRI, PstI, and EcoRV and hybridization with the Tn551 probe represent the sum of the chromosomal fragment size, in which the transposon is integrated with the size of Tn551 (5.2 kb). In Tables 2 to 5, the molecular sizes of the fragments are given after subtraction of 5.2 kb. Hybridization of the DNAs restricted with HindIII generates three bands: one corresponds to the internal Tn551-HindIII fragment, and there are two others (one includes the 1.0-kb HindIII-Tn551 right junction and the other includes the 3.0-kb HindIII-Tn551 left junction). As with the other enzymes, the results presented in Tables 2 to 5 indicate the size of the fragments in which insertions were located (i.e., the sum of the three hybridization bands minus 5.2 kb). HindIII was found to be the most useful enzyme for ascertaining the identity of two different insertions and was used to identify the number of different insertion sites in the new transposon library.

Results

Isolation of the Tn551 mutants with reduced methicillin resistance.

By transposition of Tn551 into the chromosome of the homogeneously resistant strain COL, 1012 erythromycin resistant colonies were obtained. Seventy out of these 1012 colonies showed, by population analysis profiles, a decrease in methicillin resistance compared with the parent strains COL or COL (pRN3208). Moreover, in all but two of the mutants, the Tn551 insertion changed the phenotypic expression of resistance from homogeneous to heterogeneous. Among the 70 mutants a wide range of methicillin MICs were found, from strains with an MIC as low as 1.5 $\mu$g ml$^{-1}$ to strains with an MIC as high as 200 $\mu$g ml$^{-1}$ (see data in Tables 2 through 6). The locations of the Tn551 inserts relative to those of the already characterized femA, femB, femC, and femD genes were determined by physical mapping in order to identify how many of the mutants had novel insertion sites, possibly in new genes.

Physical location of the Tn551 inserts in the staphylococcal chromosome.

Figure 3A:
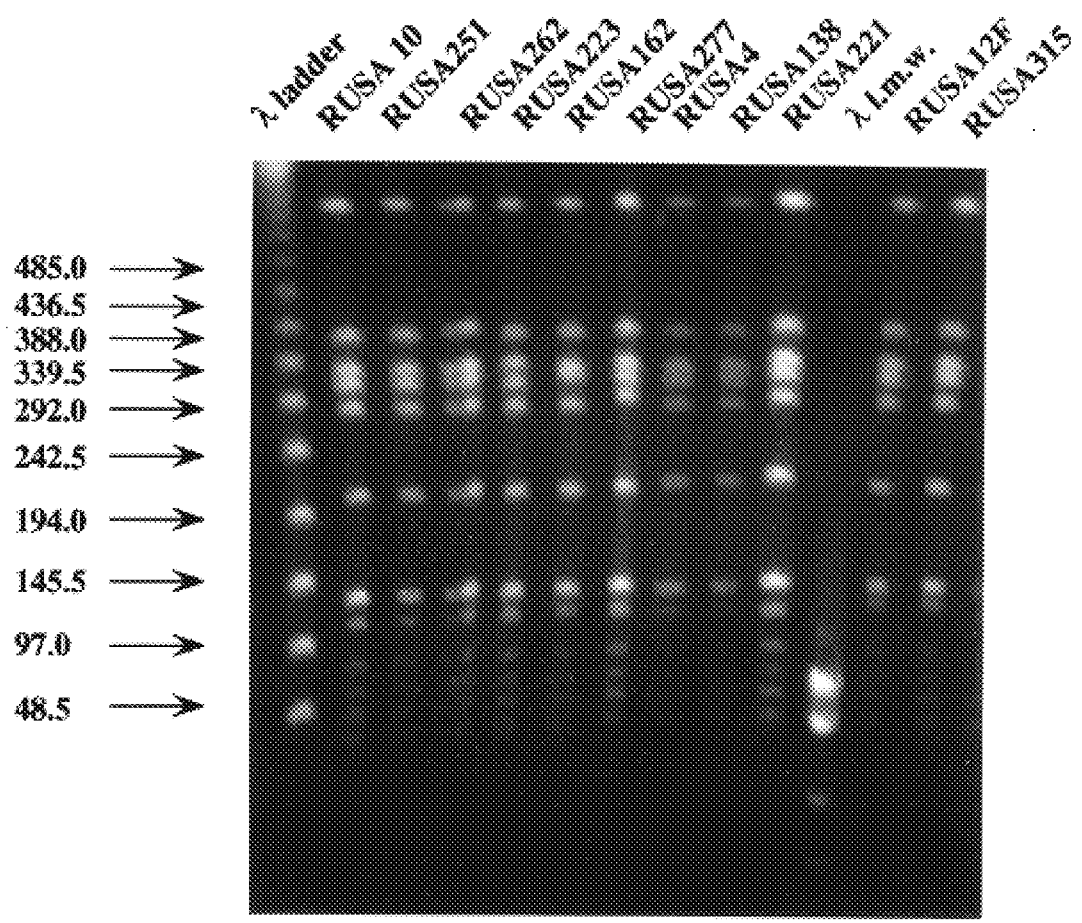
FIGS. 3A and 3B. Localization of Tn551 inserts in chromosomal SmaI fragments by Southern hybridization. Chromosomal DNA prepared from a selected group of Tn551 mutants was treated with SmaI endonuclease and the fragments were separated by pulsed-field gel electrophoresis (FIG. 3A). After transfer of the DNA, membranes were hybridized by a radiolabeled Tn551 DNA probe, as described in the Methods (FIG. 3B).
Figure 3B:
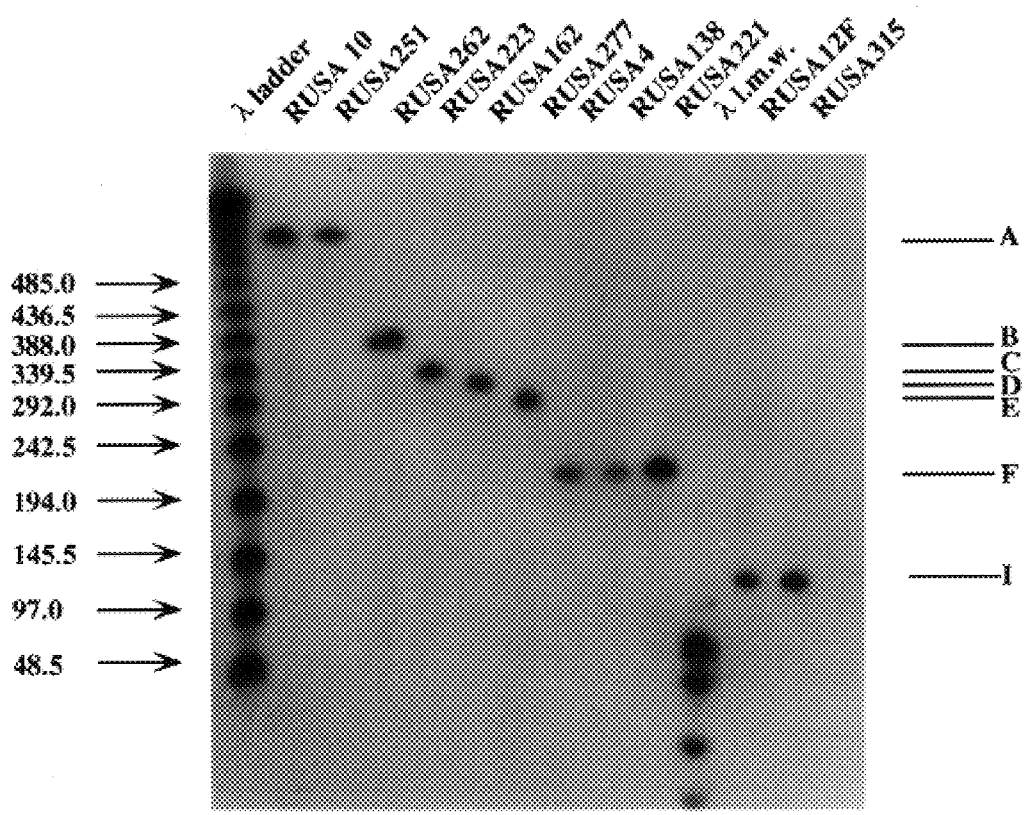

The Tn551 inserts of the 70 independently selected mutants were mapped in the staphylococcal chromosome. The DNA of each mutant was restricted with the SmaI restriction endonuclease and then separated by pulsed-field gel electrophoresis. After photography under the UV, the DNA fragments were transferred to a membrane and hybridized with the Tn551 labeled probe. Tn551 insertions were located in seven out of the 16 fragments obtained by restriction of the S. aureus chromosome with SmaI. The distribution of the 70 mutants among the fragments was the following: SmaI-A, 48; SmaI-B, 4; SmaI-C, 1; SmaI-D, 1; SmaI-E, 2; SmaI-F, 3; and SmaI-I, 11. In FIGS. 3A and 3B the location of representative mutations in the seven SmaI fragments is shown.

Physical characterization of the Tn551 mutants located on the various SmaI chromosomal fragments.

The DNAs of the mutants were digested with the appropriate restriction endonuclease, separated by conventional gel electrophoresis (or PFGE for fragments >15 kb) and hybridized with a Tn551 specific probe (pRT1). In some cases, after removing the Tn551 probe, the same DNAs were hybridized with a femA probe (pBBB31) or with a femA-femB probe (pBBB13).

Mutants in fragment SmaI-A.

The previously studied Tn551 mutants in the femA, femB, and femC genes map in the SmaI fragment A (4). In order to compare the new mutants with the previously characterized ones, DNAs of the 48 new mutants that map in fragment SmaI-A (see Table 1) were restricted with EcoRI, an enzyme that has no restriction sites in Tn551.

TABLE 1

Reference strains used in the study

| Strain | Relevant genotype | Relevant phenotype | PAP expression class | MIC ($\mu$g ml$^{-1}$) | Origin or reference |
|---|---|---|---|---|---|
| Parental | | | | | |
| COL | | Homogeneous Mc$^r$ | 4 | 1,600 | RU collection |
| COL(pRN3208) | COL with pRN3208 [Rep(Ts)] | Mc$^r$ Em$^r$ Cd$^r$ | 4 | 800 | 15 |
| M100 | Laboratory step mutant of strain 27s | Homogeneous | | 25 | 9, 25 |
| Tn551 mutants of COL | | | | | |

TABLE 1-continued

Reference strains used in the study

| Strain | Relevant genotype | Relevant phenotype | PAP expression class | MIC ($\mu g\ ml^{-1}$) | Origin or reference |
|---|---|---|---|---|---|
| Mapped in SmaI-A | | | | | |
| BB403 | COL Ω2003 (femA::Tn551) | Em$^r$ heterogeneous Mc$^r$ | 2–3 | 25$^a$ | 1, 2 |
| RUSAIII-8 | COL Ω560 (femA::Tn551) | Em$^r$ heterogeneous Mc$^r$ | 2 | 12 | 2, 9, 15 |
| RUSA10 | COL Ω552 (femB::Tn551) | Em$^r$ heterogeneous Mc$^r$ | 1 | 3 | K. Murakami; 9 |
| RUSAIII-3 | COL Ω553 (femB::Tn551) | Em$^r$ heterogeneous Mc$^r$ | 1 | 3 | J. Kornblum; 9 |
| RUSA1H1 | COL Ω554 (femB::Tn551) | Em$^r$ heterogeneous Mc$^r$ | 1 | 3 | J. Kornblum; 9 |
| RUSA20F | COL Ω555 (femB::Tn551) | Em$^r$ heterogeneous Mc$^r$ | 1 | 3 | J. Kornblum; 9 |
| RUSAIII-2 | COL Ω556 (femB::Tn551) | Em$^r$ heterogeneous Mc$^r$ | 1 | 3 | 2, 9, 15 |
| RUSAII-1 | COL Ω557 (femB::Tn551) | Em$^r$ heterogeneous Mc$^r$ | 1 | 3 | 2, 9, 15 |
| RUSA208$^b$ | COL Ω561 (femC::Tn551) | Em$^r$ heterogeneous Mc$^r$ | 1 | 3 | 18 |
| RUSA330 (1H)$^c$ | COL Ω2005 (femC::Tn551) | Em$^r$ heterogeneous Mc$^r$ | 1 | 3 | 4, 15 |
| RUSA101 | COL Ω559 (femE::Tn551) | Em$^r$ heterogeneous Mc$^r$ | 2–3 | 12–25 | 9 |
| Mapped in SmaI-F, RUSA4 | COL Ω551 (mecA::Tn551) | Em$^r$ reduced Mc$^r$ | RUSA4 type | 3 | 9, 16, 17 |
| Mapped in SmaI-I, RUSA12F | COL Ω558 (femD::Tn551) | Em$^r$ heterogeneous Mc$^r$ | 2 | 12 | 4, 15 |

$^a$The MIC for COL derivatives with the mutation Ω2003 is greater than the one for the original mutant in the BB270 background (1).
$^b$Ten other mutants (Ω562 to Ω571) have the same restriction pattern as strain RUSA208 (Ω561) (18).
$^c$This strain was obtained by transduction of the insert from mutant 1H (Ω2005) (15) into strain COL from the RU collection.

We found that the 48 new mutants could be divided in two groups according to their restriction with EcoRI. The 48 mutants were further studied by restriction analysis with PstI, EcoRV, and HindIII, enzymes used to characterize the original femA, femB and femC mutants (2, 4, 11).

The first group includes 11 mutants (Table 2) mapping in the largest EcoRI fragment of approximately 40 kb (EcoRI-a), where the femA and femB genes are also located (2).

probe, which also allowed the assignment of the insertions to the EcoRV fragments, as indicated in Table 2. After removing the Tn551 probe, the gels were hybridized with another probe (pBBB13) carrying a 10.5 kb PstI fragment covering the entire femA-femB region, including their flanking regions (2). In the six mutants in which the insertions were located in PstI-beta, the hybridization with the pBBB13 probe generated six bands of 4.3, 4.0, 2.5, 2.2, 1.6, and 1.2 kb (FIG. 4), as was expected from previously

TABLE 2

New Tn551 mutants with mutations mapping in EcoRI fragment a

| Strain | Ω no. | Size of restriction fragment (kb) | | | PAP expression class | MIC ($\mu g\ ml^{-1}$) | Backcross |
|---|---|---|---|---|---|---|---|
| | | PstI | EcoRV | HindIII | | | |
| RUSA251 | COL Ω573 | α = 10.5 | 1.2 | 5.4 | 1 | 3 | RUSA251 |
| RUSA148 | COL Ω574 | α = 10.5 | 1.6 | 6.8 | 2–3 | 25 | RUSA148 |
| RUSA270 | COL Ω575 | α = 10.5 | 4.3 | 2.2 | 2–3 | 25 | RUSA270 |
| RUSA291 | COL Ω576 | α = 10.5 | 4.0 | 7.3 | 2–3 | 25 | |
| RUSA217a | | α = 10.5 | 4.3 | —$^a$ | 2–3 | 25 | |
| RUSA101 | COL Ω559 | β = 12.4 | 2.5 | 2.9 | 2–3 | 25 | RUSA101 |
| RUSA321 | COL Ω577 | β = 12.4 | 2.5 | 2.9 | 2–3 | 25 | RUSA321 |
| RUSA252 | COL Ω579 | β = 12.4 | 0.5 | 7.3 | 3 | 100 | RUSA252 |
| RUSA279 | COL Ω580 | β = 12.4 | 2.5 | 2.4 | 3 | 50 | RUSA279 |
| RUSA289 | COL Ω581 | β = 12.4 | 7.8 | 10.1 | 3 | 100 | |
| RUSA301 | COL Ω582 | β = 12.4 | 5.9 | 11.6 | 2–3 | 25 | |

$^a$—only two HindIII fragments were visible after hybridization with the Tn551 probe; the fragment containing the Tn551 right junction is missing.

The 11 mutants whose inserts map in the 40 kb EcoRI-a fragment were further analyzed by PstI, EcoRV, and HindIII restrictions. Five of the Tn551 insertions were found to be located on the 10.5 kb PstI fragment (PstI-alpha) known to contain the femA-femB genes (2), as analyzed by the ability of the bands of 15.7 kb to hybridize to both the Tn551 and probe pBBB31 carrying a 2.2 kb EcoRV (femA) fragment. The other six mutants, in which the Tn551-hybridizing band had a size of 17.6 kb had inserts outside of the femA-femB regions in a 12.4 kb (after subtracting 5.2 kb for the transposon) fragment, termed PstI-beta (Table 2).

Figure 4:
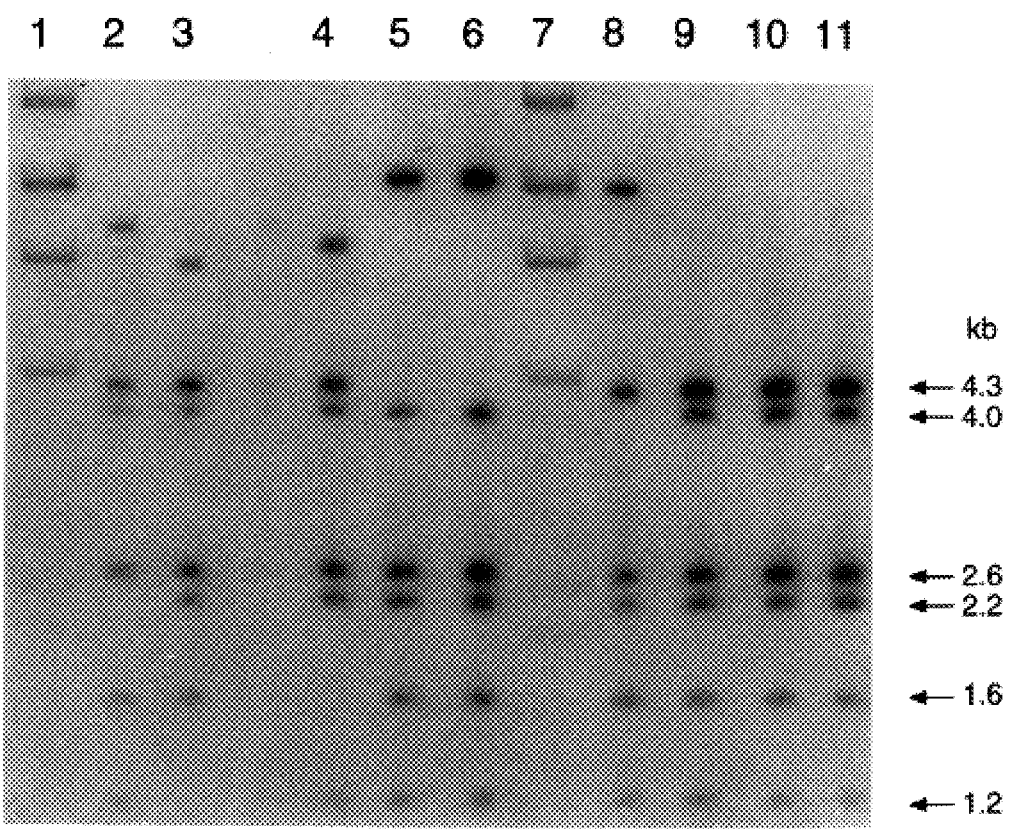
FIG. 4. Southern blots of EcoRV restriction digests of mutants located in EcoRI-a. Mutant DNA was digested with EcoRV and probed with the 10.5 kb PstI fragment from plasmid PBBB13 covering the femA-femB region (2). Lanes: 1 and 7, bacteriophage lambda plus HindIII; 2, strain BB403 (femA::Tn551); 3, strain RUSA251; 4, strain RUSA148; 5, strain RUSA270; 6, strain RUSA217a; 8, strain RUSA291; 9, strain RUSA252; 10, strain RUSA101; 11, strain RUSA279.

These conclusions were confirmed by restriction of the same DNAs with EcoRV and hybridization with the Tn551 published results (4). In the five mutants whose inserts mapped in PstI-alpha, there was a loss of one EcoRV fragment, which was replaced with another one, the molecular size of which corresponded to that of the lost fragment plus the size of Tn551 (5.2 kb). For instance, in mutant RUSA251 the 1.2 kb band was replaced by a 6.4 kb band; in RUSA148 the 1.6 kb band was replaced by a 6.8 kb band; in RUSA291 the 4.0 kb band was replaced by a 9.2 kb band; and in mutants RUSA270 and RUSA217a, the 4.3 kb band was replaced by a 9.5 kb band (FIG. 4).

Next, these five mutants were further characterized by HindIII restriction. The insert in mutant RUSA251 was mapped to the 1.2 kb EcoRV fragment known to contain femB (2). HindIII restriction of this mutant showed that its insertion is located in the same distal part of femB as those for a group of six previously described mutants (RUSAII-1, RUSAIII-2, RUSAIII-3, RUSA10, RUSA1H1, RUSA20F) (Table 1; reviewed in reference 9). On the other hand, mutants RUSA270 and RUSA217a, whose mutation are located in the 4.3 kb EcoRV fragment (Table 2), were shown to be distinct by HindIII restriction (Table 2). Strain RUSA217a contained two, rather than three, HindIII restriction bands, and was not analyzed further. The mutations in the last two of the PstI-alpha mutants were located in 1.6 kb and 4.0 kb EcoRV fragments, respectively, which were clearly different from the fragments in which femA (2.2 kb) or femB (1.2 kb) reside (FIG. 4). Thus, among the five new PstI-alpha mutants, at least three represent mutants with new inserts.

From the six mutants with insertions located in PstI-beta, two (RUSA101 and RUSA321) produced identical restriction fragment length polymorphisms (RFLPs), which differed from the RFLPs of the four other mutants (RUSA252, RUSA279, RUSA289, and RUSA301), each of which was unique to the strain (Table 2). Thus, the six new PstI-beta mutants represent mutants with five new insertion sites.

The second group of mutants in EcoRI includes 37 mutants located in EcoRI fragments of decreasing sizes ranging from 14.3 to 1.2 kb, which includes the fragment size (6.2 kb) of femC (Table 3).

1) None of the new mutants were in the femA locus, where mutations omega 2003 and omega III-8 are located (2).
2) Only one new mutant, RUSA251 (omega 573) maps in the femB locus in the same distal part of femB as a group of six previously described mutants (RUSAII-1; RUSAIII-2; RUSAIII-3; RUSA10; RUSA1H1; RUSA20F) (for a review, see 9) (Table 1).
3) All remaining 10 new mutants that map in the SmaI-A and EcoRI-a fragments are different by HindIII restriction from the previously studied mutants in femA and femB. From these 10 mutants, 3 (omega 574–omega 576) lie in a 10.5 Kb PstI fragment (PstI-alpha) that includes femA and femB. However, they were shown by EcoRV restriction to be distinct from femA and femB (Table 2). The other 7 new mutants (omega 559 and omega 577–omega 582) in EcoRI-a lie in a distinct PstI fragment (PstI-beta). Two of these (RUSA101 and RUSA321) located in PstI-beta are identical by HindIII restriction and they were used to define a new locus referred to as femE (9). These results identify 9 new and distinct insertion sites in EcoRI-a (Table 2).
4) Eleven new mutants (omega 561–omega 571) share a common restriction pattern with EcoRI, PstI, EcoRV, and HindIII that is identical to the pattern of mutant 1H previously isolated (14) and referred to as femC (4).

TABLE 3

New Tn551 mutants with mutations mapping in SmaI-A but not EcoRI-a

| Strain | Ω no. | Size of restriction fragment (kb) | | | | PAP expression class | MIC ($\mu$g ml$^{-1}$) | Backcross |
|---|---|---|---|---|---|---|---|---|
| | | HindIII | EcoRI | EcoRV | PstI | | | |
| RUSA208 | COL Ω511 | 1.7 | 6.2 | 2.2 | 12.4 | 1 | 3 | RUSA208 |
| RUSA178 | COL Ω591 | 1.7 | 7.1 | 2.2 | 12.6 | 2–3 | 12–25 | |
| RUSA247 | COL Ω596 | 1.7 | 6.5 | 2.2 | 12.6 | 2 | 12 | |
| RUSA112 | COL Ω583 | 2.3 | 14 | 8.5 | 11.7 | 2–3 | 12–25 | RUSA112 |
| RUSA114 | COL Ω584 | 2.3 | 14 | 8.5 | 11.7 | 2–3 | 12–25 | RUSA114 |
| RUSA158 | COL Ω585 | 2.3 | 14 | 8.5 | 11.7 | 2 | 12 | RUSA158 |
| RUSA176 | COL Ω586 | 2.3 | 14 | 8.5 | 11.7 | 2 | 12 | RUSA176 |
| RUSA303 | COL Ω590 | 10.8 | 8.3 | 1.3 | 12.6 | 3 | 100 | |
| RUSA219 | COL Ω595 | 6.6 | 6.4 | 2.2 | 11.5 | 2–3 | 12–25 | |
| RUSA254 | | —[a] | 6.1 | 5.5 | 12.2 | 3 | 50 | |
| RUSA296 | COL Ω701 | 12.8 | 4.2 | 5.5 | 12.6 | 2–3 | 25 | |
| RUSA164 | COL Ω707 | 1.0 | 2.4 | ND[b] | 12.2 | 2 | 12 | |
| RUSA305 | COL Ω708 | 1.9 | 1.2 | 4.0 | 13.1 | 3 | 50 | |
| RUSA182 | COL Ω587 | 5.7 | 11 | 2.3 | 5.7 | 2–3 | 12–25 | |
| RUSA237 | COL Ω588 | 3.0 | 11 | 17 | 9.7 | 2 | 12 | |
| RUSA188 | COL Ω589 | 2.8 | 9.0 | 17 | 15.3 | 3 | 100 | RUSA188 |
| RUSA233 | COL Ω592 | 7.0 | 7.1 | 2.9 | 20.6 | 3 | 50 | |
| RUSA260 | COL Ω593 | 1.7 | 7.1 | 2.6 | 6.8 | 2 | 12 | |
| RUSA190 | COL Ω594 | 2.6 | 6.4 | 16 | 14.9 | 3 | 50 | |
| RUSA319 | COL Ω598 | 5.8 | 5.0 | 4.7 | 6.8 | 2–3 | 25 | |
| RUSA152 | COL Ω599 | 6.2 | 4.5 | 2.8 | 7.5 | 3 | 100 | |
| RUSA239 | COL Ω700 | 6.0 | 4.2 | 1.5 | 6.8 | 2–3 | 25 | |
| RUSA130 | COL Ω703 | 5.2 | 3.7 | 1.4 | 7.4 | 2 | 6 | |
| RUSA172 | COL Ω704 | 5.6 | 3.7 | 6.1 | 6.5 | 2–3 | 25 | |
| RUSA317 | COL Ω705 | 5.8 | 3.7 | 2.5 | 7.5 | 2 | 6 | |
| RUSA264 | COL Ω706 | 10.35 | 2.9 | 10.0 | 10.1 | 2–3 | 25 | |
| RUSA256 | | —[c] | 4.0[d] | —[c] | ND | 3 | 50 | |

[a]—only two HindIII fragments were visible after hybridization with the Tn551 probe; the fragment containing the Tn551 right junction is missing.
[b]ND not determined.
[c]—two insertions.
[d]Doublet.

To summarize, the comparison of the 48 new mutants with the previously characterized femA, femB, and femC mutants that also map in SmaI-A allowed us to draw the following conclusions:

These eleven mutants isolated during the present work define the RUSA208 insertional cluster (17). A reexamination of previous data (17) indicates that these mutants and mutant 1H are located in PstI, EcoRI, EcoRV, and HindIII fragments of 12, 6, 2.2 and 1.7 kb, respectively.

5) The remaining 26 new mutants (omega 583–omega 599 and omega 700–omega 708) that map in SmaI-A were also studied with PstI, EcoRV, and HindIII. They could be resolved to 21 new and distinct insertion sites (Table 3).

Mutants in fragments SmaI-B, SmaI-C, SmaI-D and SmaI-E.

Prior to the present work no Tn551 insertions affecting methicillin resistance were assigned to the SmaI fragments B, C, D and E. The DNAs of the four mutants located in SmaI-B, the single mutants mapped in SmaI-C and SmaI-D, and the two mutants assigned to SmaI-E were restricted with EcoRI, EcoRV, and HindIII. Each one of the mutants showed unique restriction patterns, defining 8 different insertion sites (omega 709–omega 716) (Table 4).

RUSA223. Whereas RUSA138 and RUSA311 have PAPS very similar to that of RUSA4 (MIC=3 µg/ml) without subpopulations of more resistant colonies, strain RUSA223 has a typical heterogeneous phenotype (class 3). By restriction analysis it was possible to confirm that the insertion sites in RUSA138 and RUSA311 (omega 717 and omega 718) lie in mecA whereas the insertion in RUSA223 (omega 719) lies outside mecA in a new auxiliary gene (Table 4).

Mutants in fragment SmaI-I.

The insert in a previously isolated mutant, RUSA12F (14), was mapped in the SmaI fragment I and used to define a new locus referred to as femD (4). In the present Example, 11 new mutants were isolated and mapped in SmaI-I (omega 720–omega 730). Six of the new mutants (omega 720–omega 725) have identical restriction patterns with the enzymes EcoRI, EcoRV, PstI, and HindIII. This new cluster (RUSA315) maps in the largest HindIII fragment (HindIII-a) of 34 Kb, where RUSA12F is also located. Within this HindIII-a fragment is yet another, new mutant (RUSA266;

TABLE 4

New Tn551 mutants with mutations mapping in SmaI fragments B, C, D, E, and F

| Restriction enzyme and strain | Ω no. | Size of restriction fragment (kb) | | | | PAP expression class | MIC (µg ml$^{-1}$) | Backcross |
|---|---|---|---|---|---|---|---|---|
| | | HindIII | EcoRI | EcoRV | XbaI | | | |
| SmaI-B | | | | | | | | |
| RUSA281 | COL Ω709 | 5.0 | 9.6 | 1.12 | ND$^a$ | 1 | 3 | RUSA281 |
| RUSA262 | COL Ω710 | 5.2 | 2.1 | 16.6 | ND | 2 | 12 | RUSA261 |
| RUSA235 | COL Ω711 | 7.3 | 10.8 | 2.96 | ND | 3 | 100 | RUSA235 |
| RUSA196 | COL Ω712 | 3.0 | 10.8 | 2.96 | ND | 2–3 | 12–25 | |
| SmaI-C, RUSA223 | COL Ω713 | 5.7 | 18 | 5.1 | ND | 3 | 100 | |
| SmaI-D, RUSA162 | COL Ω714 | 2.0 | 3.4 | 4.1 | ND | 2–3 | 12–25 | |
| SmaI-E | | | | | | | | |
| RUSA206 | COL Ω715 | 3.8 | 7.1 | 1.0 | ND | 3 | 200 | |
| RUSA277 | COL Ω716 | 5.8 | 19.2 | 1.8 | ND | 2–3 | 12–25 | |
| SmaI-F | | | | | | | | |
| RUSA138 | COL Ω717 | 4.8 | ND | 18 | 4.6 | RUSA4 type | 3 | RUSA138 |
| RUSA311 | | —$^b$ | ND | 18 | 7.2 | RUSA4 type | 0.75 | |
| RUSA221 | COL Ω719 | 2.8 | ND | 7.1 | 8.4 | 3 | 100 | |

$^a$ND not determined.
$^b$—Only two HindIII fragments were visible after hybridization with the Tn551 probe; the fragment containing the Tn551 right junction is missing.

Mutants in fragment SmaI-F.

One mutant, RUSA4 (16), was shown to have lost the ability to produce PBP2A, indicating the insertion of Tn551 in the mecA gene. The precise location of the insertion in the mecA gene was established (15). The mutation in RUSA4 lies in the SmaI-F fragment (9).

In the new Tn551, library we isolated 3 new mutants that insert in the SmaI-F fragment: RUSA138, RUSA311 and omega 726) which may be distinguished from the RUSA315 cluster by HindIII and PstI restriction. As the sequence of RUSA12F is not available it is not known if these 7 new insertion sites and RUSA12F are in the same gene. The other four new mutants (omega 727–omega 730) have unique HindIII patterns, identifying 4 different insertion sites (Table 5).

TABLE 5

Tn551 mutants with mutations mapping in the SmaI-I fragment

| Strain | Ω no. | Size of restriction fragment (kb) | | | | PAP expression class | MIC (µg ml$^{-1}$) | Backcross |
|---|---|---|---|---|---|---|---|---|
| | | HindIII | EcoRI | EcoRV | PstI | | | |
| RUSA12F | COL Ω558 | 34 | 10.3 | 7.5 | 5.8 | | | RUSA12F |
| RUSA315 | COL Ω720 | 34 | 10.3 | 7.5 | 5.8 | 2 | 6 | RUSA315 |
| RUSA243 | COL Ω721 | 34 | 10.3 | 7.5 | 5.8 | 2 | 6 | RUSA243 |
| RUSA184A | COL Ω722 | 34 | 10.3 | 7.5 | 5.8 | 2 | 12 | |
| RUSA299 | COL Ω723 | 34 | 10.3 | 7.5 | 5.8 | 2 | 12 | |

TABLE 5-continued

Tn551 mutants with mutations mapping in the SmaI-I fragment

| Strain | Ω no. | Size of restriction fragment (kb) | | | | PAP expression class | MIC ($\mu$g ml$^{-1}$) | Backcross |
| --- | --- | --- | --- | --- | --- | --- | --- | --- |
| | | HindIII | EcoRI | EcoRV | PstI | | | |
| RUSA313 | COL Ω724 | 34 | 10.3 | 7.5 | 5.8 | 2 | 12 | |
| RUSA18F | COL Ω725 | 34 | 10.3 | 7.5 | 5.8 | 2 | 12 | RUSA18F |
| RUSA266 | COL Ω726 | 34 | 10.3 | 7.5 | 1.8 | 2 | 6 | RUSA266 |
| RUSA168 | | —[a] | 9.8 | 0.8 | 10.8 | 2–3 | 12–25 | |
| RUSA150 | COL Ω728 | 5.6 | 9.8 | 0.8 | 10.8 | 3 | 50 | |
| RUSA122 | COL Ω729 | 1.9 | 9.8 | 1.4 | 10.8 | 3 | 50 | |
| RUSA192 | COL Ω730 | 1.25 | 4.2 | 6.5 | 12.8 | 3 | 50 | |

[a]—only two HindIII fragments were visible after hybridization with the Tn551 probe; the fragment containing the Tn551 right junction is missing.

In summary, of the 70 new mutants with decreased methicillin resistance, the number of novel insertion sites is 58, of which only two are mecA. The 41 novel insertion sites outside mecA were distributed as follows: 27 in SmaI-A, 4 in SmaI-B, 1 i SmaI-C, 1 in SmaI-D, 2 in SmaI-E, 1 in SmaI-F, and 5 in SmaI-I. Only 12 of the insertions seem identical to previously described Tn551 sites: the single new femB mutant RUSA251 and the eleven mutants that appear to belong to the femC group.

Transduction crosses an analysis of transductants.

A number of the auxiliary mutations isolated were transduced back into the parental strain COL. All backcrosses analyzed both by PAP analysis and by HindIII restriction analysis, as described in Materials and Methods, are listed in Tales 2 to 5. In all of these 21 crosses, 100% cotransduction of the ery$^R$ marker with reduced methicillin resistance was obtained. There was no evidence of reversion to resistance or transposition.

Effects of the Tn551 mutation on bacterial physiology.

Figure 5:
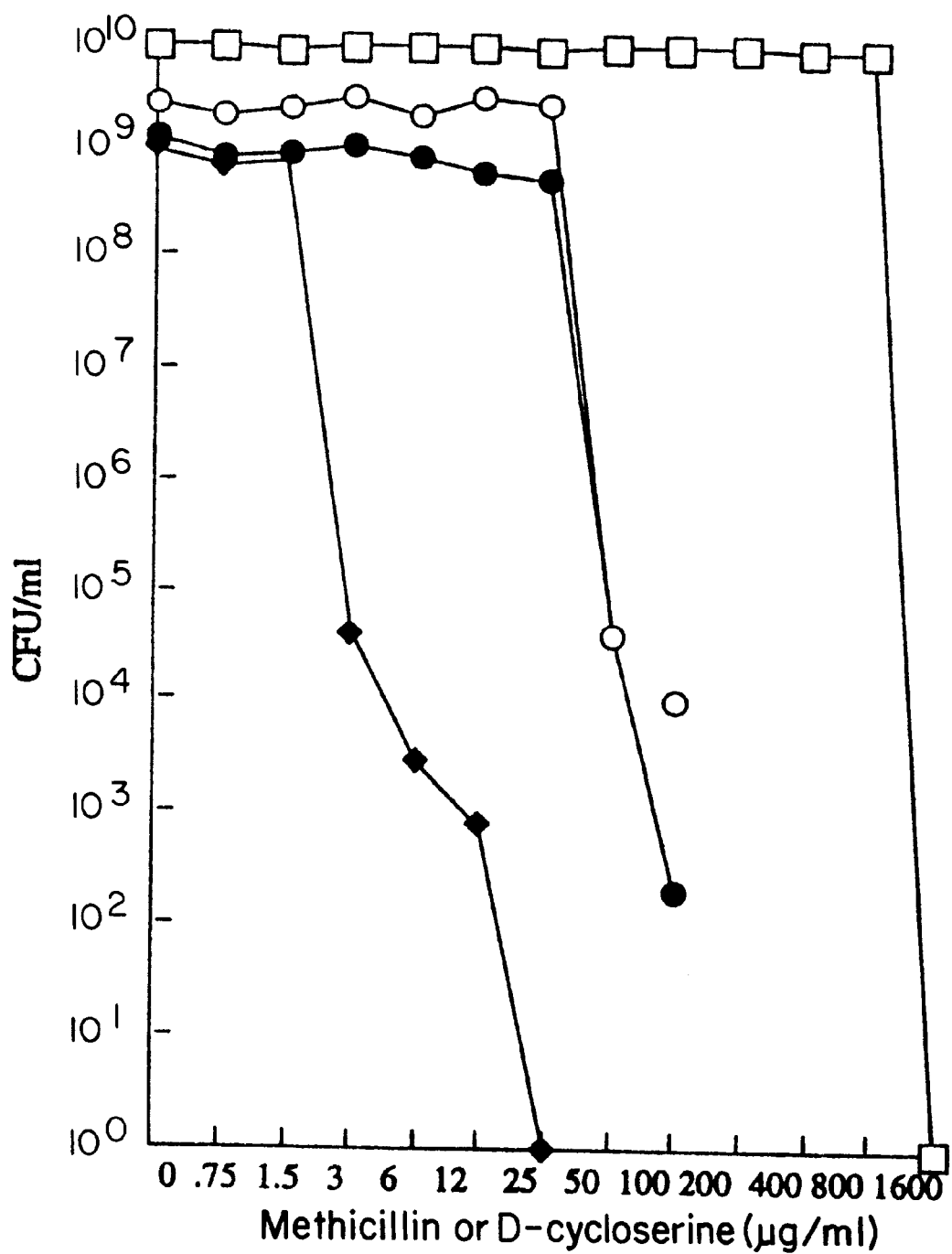
FIG. 5. Effect of a Tn551 mutation on the phenotypic expression of methicillin resistance and resistance to D-cycloserine. The antibiotic resistance phenotypes of the parental MRSA strain COL (□) and its Tn551 mutant RUSA10 (♦) were determined by population analysis, as described in the Methods for Example 1, infra. The same method was also used to compare the effect of RUSA10 mutation on the expression of resistance against another antibiotic, D-cycloserine, in strain COL (○) and the mutant RUSA10 (●).

Several of the auxiliary mutants that were analyzed showed reduced growth rates, as compared to the parental bacterium. This was also true when the Tn551 mutation was crossed out of the MRSA genetic background into a laboratory-derived methicillin resistant step mutant, strain M100 (Tonin and Tomasz, 1986, Antimicrob. Agents Chemother. 35:124–129). As to the effect of the Tn551 insertion on the phenotypic expression of antibiotic resistance traits other than resistance against beta lactams, this was tested with mutant RUSA10 using susceptibilities to D-cycloserine, tetracycline, ofloxacin, and gentamycin. In contrast to the massive reduction in methicillin resistance level and the appearance of heterogeneous phenotype, the RUSA10 mutation did not change the antibiotic susceptibilities (MIC values) of the parental strain COL to tetracycline (200 $\mu$g/ml), ofloxacin (1.5 $\mu$g/ml), gentamycin (0.75 $\mu$g/ml), or D-cycloserine (50 $\mu$g/ml) and the expression of resistance to these antibiotics remained homogeneous (FIG. 5).

Discussion

The new transposon library described here has produced evidence for a surprisingly large number of chromosomal sites that can profoundly influence the level of methicillin resistance. Only two of the new Tn551 inserts were in the mecA gene. The rest of the insertion sites distributed widely in 7 out of the 16 chromosomal SmaI fragments. The largest number of mutations—48—was in fragment A and the rest in fragments B (4), C (1), D (1), E (2), and I (12). Thus, it appears that the overwhelming majority of the new Tn551 mutants are in auxiliary (22) or FEM (3) genes, i.e., genetic determinants needed for the phenotypic expression of optimal (high) levels of methicillin resistance. Previous work has described 12 Tn551 MRSA mutants with reduced resistance. The first one of these, omega 2003, has led to the identification of the femA gene by Berger-Bächi (1,2). A second mutant, III/8 (14), was also mapped in femA (2). Six additional mutants were mapped in the distal part of a second locus femB (2,9) and, more recently, a mutant was also identified in the ORF of femB (13). Mutants 1H and 12F (14) have led to the identification of genes femC and femD, respectively (4). A single Tn551 mutant, RUSA4 (16), was located inside the mecA gene (15) in the SmaI chromosome fragment F (9).

In contrast to these 12 previously described insertional mutants (defining the fem genes A, B, C and D) which were located either on SmaI fragment A or I, the large crop of new insertion sites described in this Example were scattered over seven of the sixteen SmaI fragments, fragments A, B, C, D, E, F and I. The finer physical mapping by the restriction nucleases EcoRI, PstI, EcoRV, and HindIII allows one to identify 58 distinct, as yet undescribed Tn551 insertion sites, each one of which results in reduction of methicillin resistance. Only two sites, mapped in the mecA gene, resulted in a homogeneous reduction of resistance. The rest of the Tn551 mutants exhibited heterogeneous phenotypes in which the resistance level of the majority of cells was reduced (from the extremely high MIC of the parental cells—1600 $\mu$g/ml) to a range of MICs from 1.5 up to 200 $\mu$g/ml.

Each of these heterogeneous phenotypes were stable and characteristic of the particular mutant and in genetic backcrosses these unique phenotypes were reproduced with remarkable fidelity.

It is not clear how many new genetic determinants are defined by the new inserts. Nevertheless, the large physical distance between the four insertion sites located in the SmaI fragment B, the single insertion sites in fragments C and D, and the two distant sites on fragments E and F are likely to represent at least nine new genetic determinants. This number does not include the several new genes defined by the new Tn551 mutants located on SmaI fragments A and I.

The genes implicated in the transposon mutagenesis may be involved with the structure of staphylococcal cell wall since previous studies have shown that the femA and B mutants had abnormal peptidoglycan crossbridge structures (5,6,7) and a femC mutant was shown to be blocked in the amidation of the alpha-carboxyl group of the D-glutamic acid residues in the muropeptide subunits (17). A model for the mechanism of how abnormalities of muropeptide structure may lead to reduction in beta lactam antibiotic resistance level has been proposed recently (9).

The consistent appearance of heterogeneity among virtually all auxiliary mutants described so far is not well understood. It is possible that in most of these mutants the Tn551 insert is either in the promoter or in the distal part of the open reading frame, allowing partial read-through of the gene. This is consistent with the finding that normal (parental) muropeptide species is present (albeit in greatly reduced quantities) in the cell walls of several of the auxiliary mutants analyzed so far. It is possible indeed that insertion in the ORFs of these genes is lethal. The reduction in growth rate of the femB mutant RUSA10, in the absence of antibiotic is consistent with this suggestion. The auxiliary mutants may indeed represent "methicillin-conditional" mutants in essential genes of staphylococcal peptidoglycan metabolism.

EXAMPLE 2

Reduced Methicillin Resistance in a New *Staphylococcus aureus* Transposon Mutant That Incorporates Muramyldipeptides into the Cell Wall Peptidoglycan Screening of a new Tn551 library constructed in the background of a highly methicillin-resistant *Staphylococcus aureus* strain identified a new insertion site located on the SmaI B-fragment of the chromosome which reduced the minimal inhibitory concentration value of the parent (1600 µg/ml) to 25–50 µg/ml in the mutant, caused heterogeneous expression of resistance, and abnormality of peptidoglycan composition: the unsubstituted pentapeptide was absent and alanyl-glutamate and alanyl-isoglutamate-containing muropeptides were incorporated in the cell wall. There was an accumulation of large amounts of the UDP-linked muramyl-dipeptide in the cytoplasmic wall precursor pool of the mutant. Both reduced (heterogeneous) antibiotic resistance and all the biochemical abnormalities were reproduced in genetic backcrosses using transduction with phage 80 alpha. Mutant RUSA 235 appears to be impaired in the biosynthesis of the staphylococcal cell wall precursor muropeptide before the lysine addition step. We propose to provisionally call the gene inactivated in this mutant femF.

Materials and Methods

Bacterial strains and growth conditions.

The highly and homogeneously methicillin resistant parental strain COL and Tn551 mutants used in this study are listed in Table 1, supra. Growth medium and methods used for the cultivation of the strains were described earlier (18). Population analysis profiles were done as described (8).

Selection of RUSA235 by Tn551 transposition and genetic crosses.

Tn551 transposition (19) and transduction with phage 80 alpha (18) were carried out by previously described methods. The transduction crosses were performed using the newly isolated mutant RUSA235 as donor and the homogeneously resistant parental strain COL as recipient. Among the 46 transductants analyzed the cotransfer of the Tn551 marker (erythromycin) and reduced methicillin resistance was 100%.

Preparation of chromosomal DNA for conventional and pulsed-field gel electrophoresis (PFGE).

Preparation of chromosomal DNA from strain COL and the various Tn551 insertional mutants was carried out as previously described (10).

Preparation of DNA probes and hybridization.

The whole plasmid pRT1 (that contains a 4 Kb HpaI-XbaI internal fragment from transposon Tn551) was used as probe (15). Standard methodology was followed for $^{32}$P-labeling of the probes by nick translation, prehybridization and hybridization (20). A nonradioactive labeling system (ECL) from Amersham (Arlington Heights, Ill.) was used according to the manufacturer's instructions. For blotting of conventional gels to nitrocellulose membranes (Schleicher & Schuell BA85, USA) a vacuum blotting apparatus was used (Vaccu-blot, Pharmacia/LKB) according to the manufacturer's instructions. For the blotting of pulsed-field gel electrophoresis gels we followed a previously described method (10).

Restriction digestion.

Restriction digestions with SmaI, EcoRI, EcoRV, PstI, and HindIII nucleases were carried out according to the manufacturers' recommendations (New England Biolabs, Inc.).

Conventional and pulsed-field gel electrophoresis.

These were carried out as described in Example 1, supra (see reference 10).

Preparation of the muropeptides and separation with reversed-phase high performance liquid chromatography (HPLC).

Muropeptides were prepared from cell walls as previously described (5) except that the alkaline phosphatase step was omitted. The structure of the muropeptides was determined by amino acid and mass spectrometric analysis (17).

N-acetyl-D-glucosaminyl-(beta-4)N-acetylmuramyl-L-alanyl-D-isoglutamine-(GMD P) was obtained from Calbiochem (San Diego, Calif.). The GMDP analog with free glutamic acid residue was kindly provided by the C—C Biotech Corporation, Poway, Calif.

Preparation of the UDP-linked precursor and analysis with HPLC.

Cytoplasmic pools of UDP-linked peptidoglycan precursor were extracted by a modification of a previously described method (Handwerger et al., 1994, J. Bacteriol 176:260–264). Cells were grown to mid-logarithmic phase in TSB at 37° C. with aeration, chilled and harvested by centrifugation, washed in 0.9% saline and extracted with cold trichloroacetic acid (final concentration of 5 %) for 30 min, at 4° C. The extract containing the pool of precursors was separated by gel filtration on a Sephadex G-25 column (Pharmacia, Alameda, Calif.) eluted with water. Hexosamine-containing fractions identified by the assay of Ghuysen et al. (1966, Methods Enzymol. 8:684–699) were combined and lyophilized. Separation of the muropeptides by HPLC was performed essentially by the method of Flouret et al. (1991, Anal. Biochem. 114:59–63) with some modifications. Samples were applied to a 3.9×300 mm reverse-phase column (uBondapack C18, Waters Chromatography Division, Millipore Co., Milford, Mass.) guarded by a 15×3.2 mm Perisorb RP-18 precolumn (Pierce Chemical Co., Rockford, Ill.). The column was operated under isocratic elution at room temperature with 0.05 M ammonium phosphate, pH 5.1, at a flow rate of 0.5 ml/min, which was changed to 2.0 ml/min at 25 min. Eluted compounds were detected by absorption at 254 nm (Spectroflow 757, Kratos Analytical Instruments, Ramsey, N.J.), the areas of the peaks of interest were added together, and individual peaks were expressed as a percentage of this total. Peaks representing cell wall precursors prepared from *S. aureus* 209P grown in TSB in the presence of cycloserine (120 µg/ml) and vancomycin (4 µg/ml) were used as reference for determination of retention times of the tripeptide and pentapeptide precursor compounds. The major uridine-diphosphate (UDP) containing peak from the cytoplasmic precursor extract of RUSA235 was collected, desalted and analyzed for amino acid composition. UDP-N-acetylglucosamine from Sigma (St. Louis, Mo.) was used as a standard. Boiling samples for 3 min in 0.1 M HCl before loading onto the column was used to identify UDP-containing peaks.

Results

Reduced methicillin resistance in mutant RUSA235.

Figure 6:
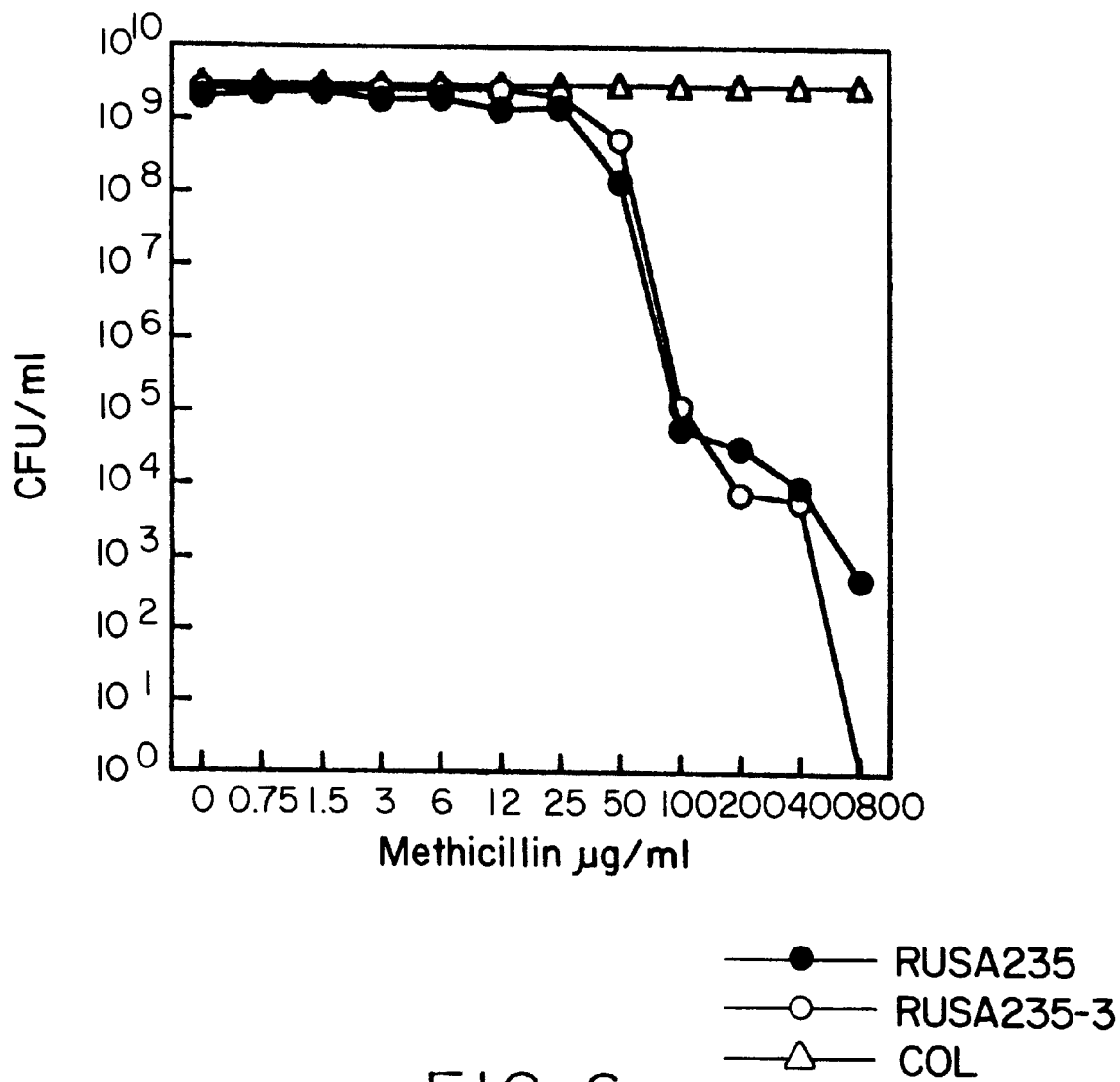
FIG. 6. Phenotypic expression of methicillin resistance of mutant RUSA235 and its backcross RUSA235-3. Bacterial cultures were grown in tryptic soy broth with aeration to stationary phase. The bacteria were plated on agar containing various concentrations of methicillin as described for the method of population analysis (8). CFU, colony-forming units; (●), RUSA235; (○), RUSA235-3; (Δ), COL.

FIG. 6 shows the population analysis profiles of the mutant RUSA235 (omega 711) and one of its backcrosses (transductant into COL) RUSA235-3. The Tn551 insertion caused a change in the resistance phenotype from homogeneous (parental) to a heterogeneous one and a reduction of the MIC from 1600 μg/ml to 25–50 μg/ml for the majority of the mutant cells.

Physical location of the Tn551 insert.

Chromosomal DNA prepared from mutant RUSA235 was restricted with the endonuclease SmaI. DNA fragments separated by PFGE were hybridized with a Tn551 DNA probe to locate the insert. The transposon in strain RUSA235 was located in the SmaI-B fragment.

Figure 7:
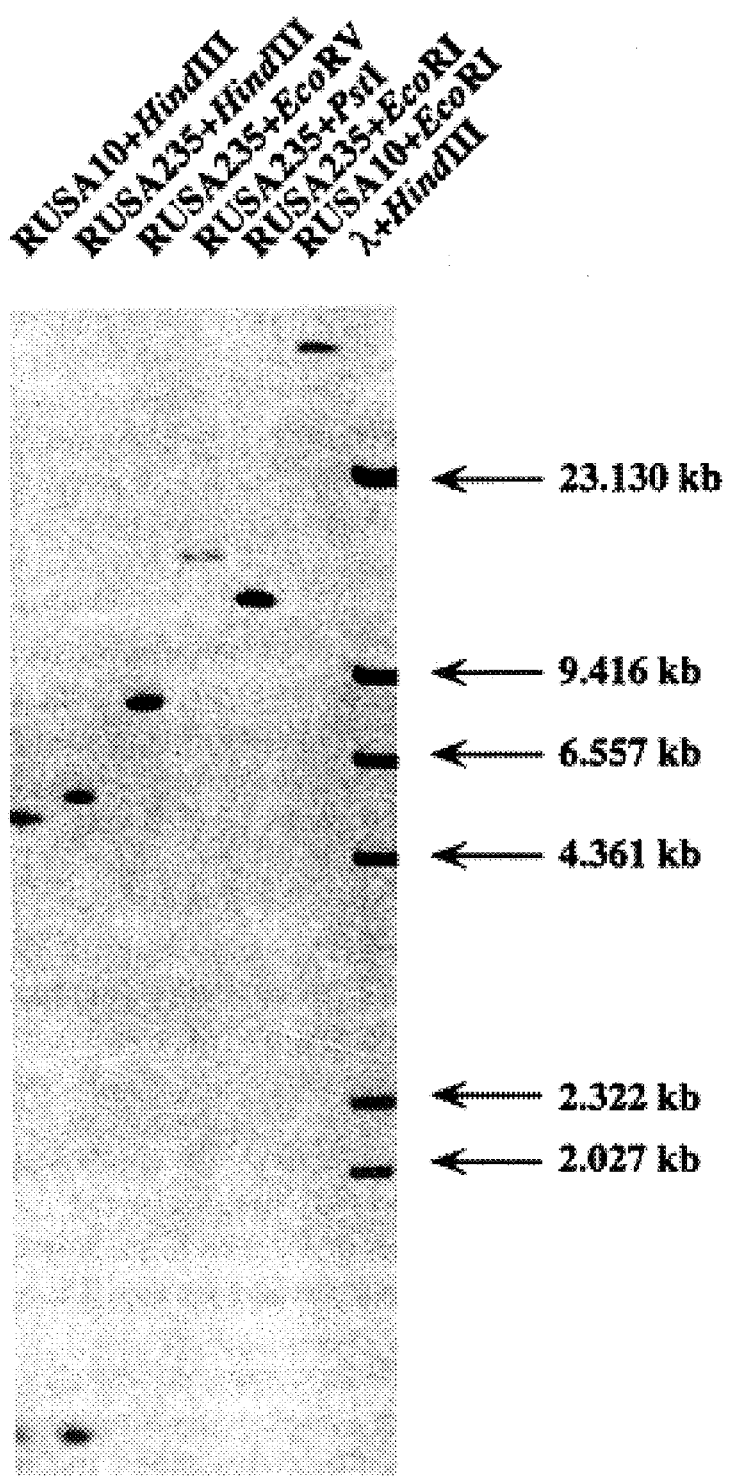
FIG. 7. Restriction, fragmentation pattern of mutant RUSA235. Chromosomal DNA isolated from RUSA235 was restricted with different restriction enzymes, and the fragments were separated by pulsed-field gel electrophoresis in a Chef-DRII apparatus (Bio-Rad) for 15 h at 14° C. The Tn551 inserts were located after Southern hybridization and probing with a nonradioactive Tn551 probe. The second through fifth lanes contain RUSA235 DNA restricted with HindIII, EcoRV, PstI, and EcoRI, respectively. The first and sixth lanes include as controls HindIII and EcoRI digests of a femB mutant (RUSA10). The seventh lane contains λ-DNA restricted with HindIII as a molecular size marker.

Additional restriction digests were prepared using four other endonucleases (HindIII, EcoRV, EcoRI, PstI) in order to more accurately characterize the insertion site in mutant RUSA235 (FIG. 7). This analysis showed that the insertion site in RUSA235 could be located in restriction fragments of the following sizes: HindIII (7.3 Kb), EcoRV (3 Kb), EcoRI (10.8 Kb); PstI (12 Kb).

The identity of the insertion site in mutant RUSA235 and several of its backcrosses into COL (transductants RUSA235-3, -9, -14) was established by HindIII restriction of their DNAs followed by hybridization with the Tn551 probe (data not shown).

Muropeptide composition of the peptidoglycan of RUSA235 as determined by HPLC and chemical analysis.

Figure 8A:
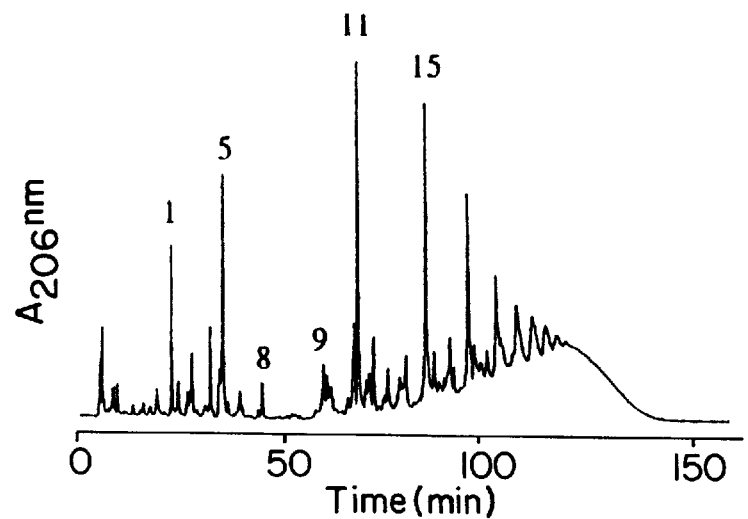
FIG. 8. HPLC elution profiles of muropeptides isolated from the parental strain, mutant RUSA235, and its backcross. Peptidoglycan was isolated and hydrolyzed with muramidase, and the resulting muropeptides were separated by HPLC as described under "Experimental Procedures." A: muropeptide pattern of COL; B: muropeptide profile of RUSA235; C: muropeptide profile of RUSA235-3. For the structures of muropeptides 1,5,8,9,11, and 15, refer to Reference 5.
Figure 8B:
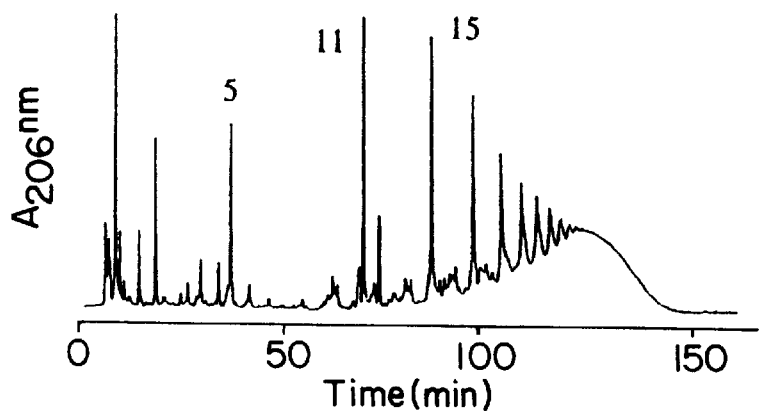
Figure 8C:
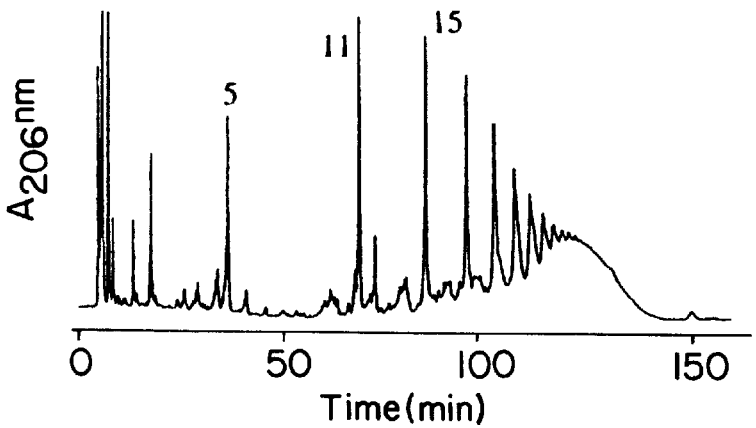

The HPLC elution profiles for the parental strain COL, RUSA235 and its backcross RUSA235-3, are shown in FIG. 8. Except for peak 1, each major parental muropeptide species was present in the HPLC profile of mutant 235, and peaks 8 and 9 were only present in reduced quantities. A novel feature of the HPLC profile of mutant RUSA235 was the appearance of new peaks at retention times of 13.6 (peak a) and 17.6 (peak b) min.

Figure 9A:
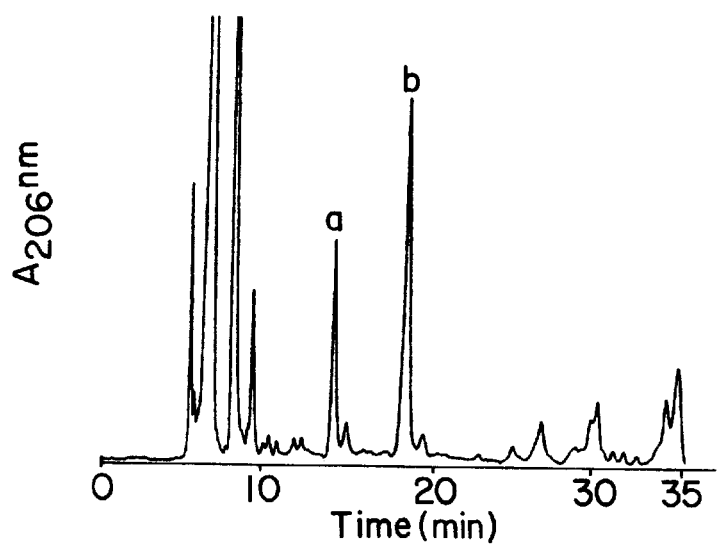
FIG. 9. Section of the HPLC profile of mutant RUSA235 showing the two newly identified peaks and comparison with the two disaccharide dipeptide standards. The elution profile and retention time of peak from RUSA235 (A) are identical to those of the GMDP standard with isoglutamine (iGln; B). Peak b from RUSA235 has an elution profile identical to that of the GMDP standard with glutamic acid (C).
Figure 9B:
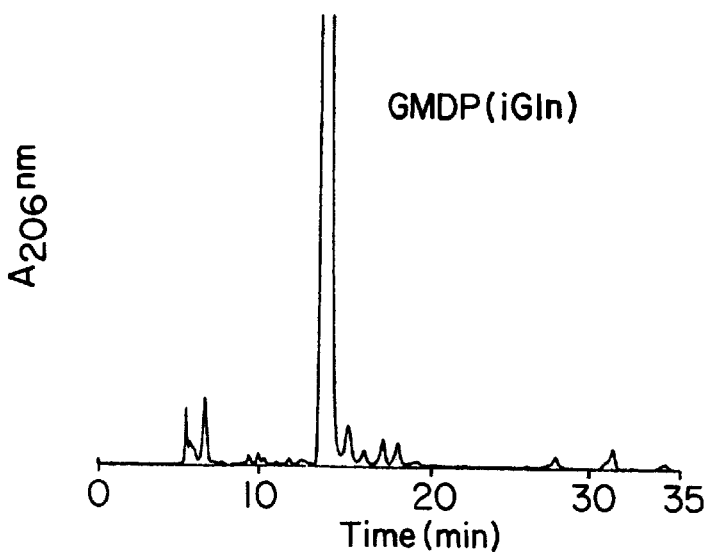
Figure 9C:
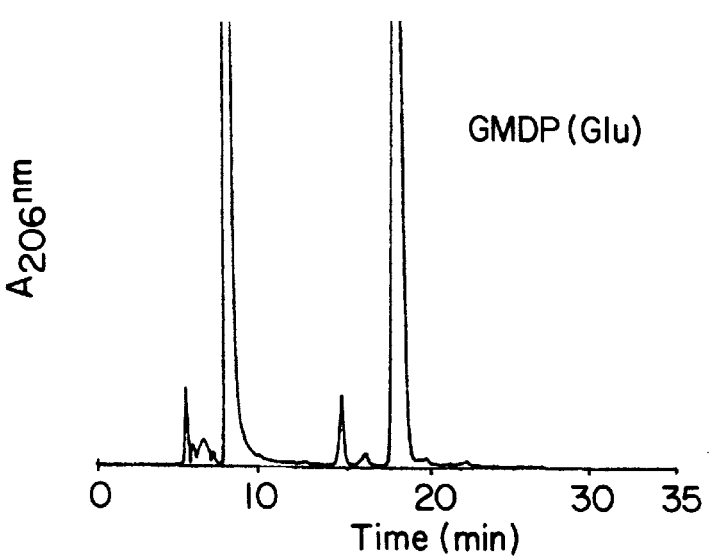

These new peaks were collected and analyzed for amino acid composition and molecular size (mass spectrometry). Table 6 shows the retention times, amino acid composition and molecular size for the two new muropeptide species. Both compounds were identified as disaccharide dipeptides with identical amino acid composition (1 mole each of alanine and glutamic acid), but the two muropeptides differed from one another by 1 mass unit. The peak with shorter retention time coelutes with a commercially available muropeptide standard containing isoglutamine. The peak with the longer retention time coeluted with the GMPD standard containing glutamic acid residue (FIG. 9). This is in accordance with previously published results (17), which showed that in the HPLC system employed here, muropeptides in which the isoglutamine (iGln) was replaced by a free glutamate eluted with longer retention times.

TABLE 6

Amino acid analysis and molecular masses of the anomalous muropeptides isolated from the muramidase digest of the peptidoglycan of mutant RUSA235

| Muropeptide[a] | HPLC retention time (min) | Amino acid analysis | | | | Mass spectrometry $(M + H)^{+c}$ |
|---|---|---|---|---|---|---|
| | | Glx | Ala | Lys | Gly | |
| a | 13.6 | 1 | 1.25 | ND[b] | ND | 698.3 |
| b | 17.6 | 1 | 1.08 | ND[b] | ND | 699.3 |

[a]See FIG.
[b]ND, not detected
[c]$(M + H)^+$ ion of the reduced muropeptide

UDP-lined cell wall precursor pool of parental strain COL and mutant RUSA235.

Figure 10A:
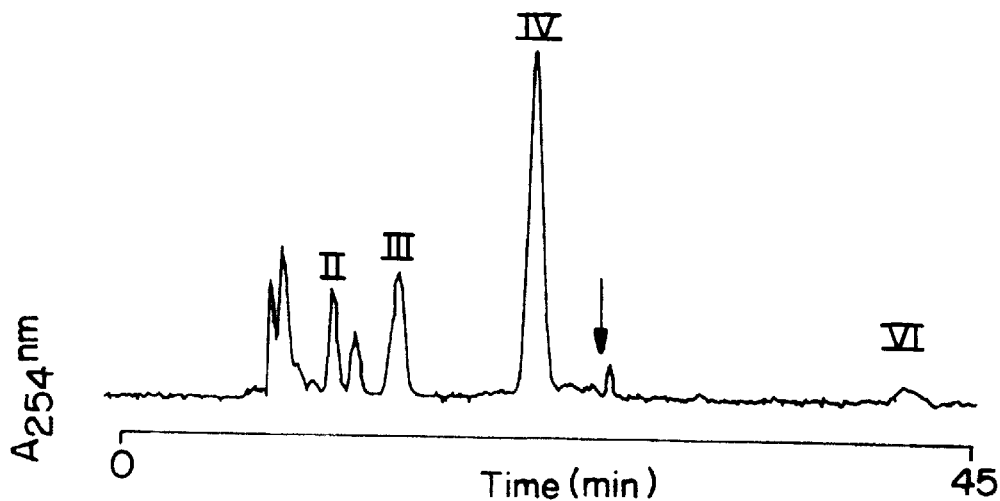
FIG. 10. Separation of cytoplasmic peptidoglycan precursors isolated from the parental strain and mutant RUSA235 by HPLC. Cytoplasmic precursors were isolated and separated by HPLC as described under "Experimental Procedures." The flow rate was changed from 0.5 to 2.0 ml/min at the times indicated (↓). A: elution profile of mutant RUSA235; B: elution pattern of the parental strain (COL). Peak numbers correspond to compounds in Table 7.
Figure 10B:
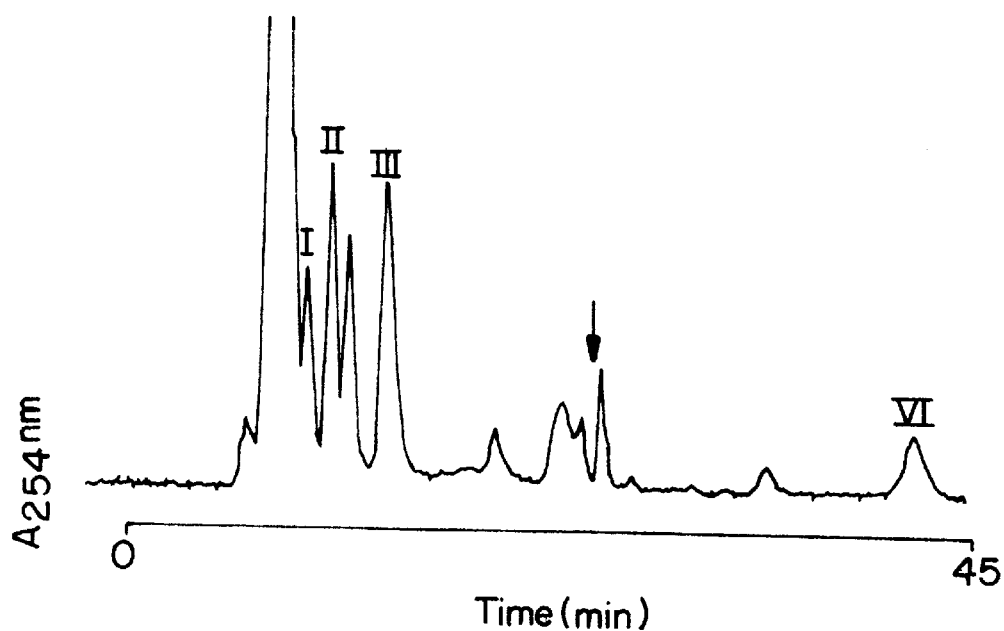

FIG. 10 shows the HPLC elution profiles of UDP-linked precursors extracted from the parental and mutant staphylococci. Table 7 shows that quantitative differences between the composition of parental and mutant cell wall precursor pool. Peak IV, a component absent from the precursor pool of parental cells, has accounted for over 60% of the UDP-linked muropeptides in the mutant extract. This material was isolated and identified as UDP-N-acetyl-muramyl-alanyl-glutamate on the basis of chemical analysis (UV spectra, Elson-Morgan reaction and quantitative amino acid analysis).

TABLE 7

UDP-linked peptidoglycan of mutant RUSA235 and its parental strain (COL)
The relative amounts of the compounds (peaks I–VI) are expressed as percentages (calculated from the UV absorbance of peaks in HPLC elution profiles). Data represent the means of three experiments.
UDP-GlcNAc, uridine diphospho-N-acetylglucosamine; UDP-MurNAc, uridine diphospho-N-acetylmuramic acid, Ala, L-alanine; Glu, D-glutamate; Lys, L-lysine; Penta, L-alanine:D-glutamate:L-lysine:D-alanine:D-alanine

| Strain | I UDP-GlcNAc % | II UDP-MurNAc % | III UDP-Mur—Ala % | IV UDP-Mur—Ala—Glu % | V UDP-Mur—Ala—Glu—Lys % | VI UDP-Mur—Penta % | Total hexosamines nmol |
|---|---|---|---|---|---|---|---|
| COL | 20 ± 2 | 28 ± 3 | 41 ± 3 | 0 | 0 | 11 ± 2 | 42 ± 8 |
| RUSA235 | 0 | 10 ± 3 | 22 ± 4 | 63 ± 5 | 0 | 3 ± 1 | 252 ± 30 |

Discussion

The screening of a library of Tn551 mutants of MRSA for reduced methicillin resistance has already identified several transposon mutants with altered peptidoglycan composition, either in the stem peptides or in the crossbridges. Previously described mutants located outside the mecA gene had transposon inserts in the SmaI A fragment (mutants omega 2003, RUSA10, RUSA208—with inserts in the auxiliary genes femA, femB, and femC) or in the SmaI I fragment (RUSA12F—femD) of the staphylococcal chromosome (4, 9, 11, 17). Mutant RUSA235 differs from these previous transposon mutants in that the insertion is located in the SmaI B fragment. We propose to refer to the inactivated auxiliary gene as femF, following the currently used, provisional nomenclature.

The peptidoglycan of RUSA235 is composed of the same muropeptide species as the parental strain in the same proportions and same degree of crosslinking (as judged by the comparable amounts o cross-linked peptides 9 and higher), except for the reduced amounts of the unsubstituted disaccharide pentapeptide monomer (and muropeptides 8 and 9) and the presence of the two novel disaccharide dipeptides. Each of these two new muropeptides contained one mole each of alanine and glutamate, but lacked lysine, glycine, and any other amino acids. The two muropeptides differed from one another by one mass unit. These data and the retention times of the components during reverse phase HPLC indicate that they are composed of disaccharide dipeptides in which the first amino acid is alanine and the amino acid at the second position is either isoglutamine or glutamic acid. Analysis of the cytoplasmic peptidoglycan precursor pool of RUSA235 revealed an accumulation of the UDP-linked muramyl-dipeptide containing equimolar amounts of alanine and glutamic acid and reduced level of the UDP-linked muramyl-pentapeptide. These data indicate that the RUSA235 mutation is in a gene (femF) responsible for the biosynthetic step in which the L-lysine residue is added to the UDP-linked muramyl dipeptide chain. A quantitative impairment of the muropeptide synthetic route at this step may explain the observed deficit in muropeptide species which contain unsubstituted pentapeptide units in the mutant peptidoglycan.

Some of the properties of RUSA235 are reminiscent of a *S. aureus* conditional mutant TOF-95 (Good and Tipper, 1972, J. Bacteriol 111:231–241) and RUS 1 (Chatterjee and Young, 1972, J. Bacteriol 111:220–230), both of which are defective in cell wall precursor synthesis which also showed accumulation of UDP-linked muramyl dipeptide cell wall precursors and a defective lysine adding enzyme. However, in contrast to TOF-95, RUSA235 was capable of growth at elevated temperature (43° C.) without osmotic supplementation of the medium.

The reasons for the drastic reduction in the methicillin MIC value in mutant RUSA235 are not clear. In a previous report (9), we suggested that the high methicillin MIC values of some MRSA strains may be related to the effective competition by the normal muropeptide precursors for a critical site on the PBP2A protein (i.e., the mecA product). In this model, wall precursors of abnormal chemical structure would be less effective competitors, thus allowing acylation of the active site of the cell wall synthetic enzyme (presumably PBP2A) to occur at a lower concentration of the antibiotic (9). Other alternative mechanisms cannot be excluded. The normal muropeptide precursors in which mutant RUSA235 shows a deficit may perform some as yet undefined signaling role in wall synthesis. The muramyl dipeptide residues lacking the diaminoacid component (and thus unable to participate in crosslinking) may incorporate into some structurally critical positions in the peptidoglycan and this may, indirectly, jeopardize the integrity of wall structure during perturbation of wall synthesis by antibiotics.

These data indicate that interference with the peptidoglycan biosynthesis at the cytoplasmic level affects methicillin resistance in *S. aureus*.

EXAMPLE 3

Molecular Cloning and DNA Sequencing of the *Staphylococcus aureus* UDP-N-Acetylmuramyl Tripeptide Synthetase (murE) Gene, Essential for the Optimal Expression of Methicillin Resistance Methicillin resistant strains of *Staphylococcus aureus* (MRSA) contain the mecA determinant which encodes for the low affinity penicillin-binding protein, PBP2a (30,49, 52). The mecA determinant is "added" to the complement of the four normal staphylococcal PBPs which are retained in their high P-lactam affinity forms in MRSA strains. Several lines of evidence indicate that the presence of mecA and its normal expression into PBP2a are not sufficient to explain the large strain-specific variation observed in antibiotic resistance levels and phenotypes of MRSA isolates (12,22). In addition, experiments with Tn551 insertional mutations have identified a number of chromosomal genes (referred to as auxiliary genes or fem genes), the functions of which are essential for optimal expression of methicillin resistance (2,26,22). Four of these genes (femA, femB, femC and femE) (3,9) were mapped within the largest SmaI-A fragment, and femD is located within the SmaI-I fragment of the *S. aureus* chromosome map (3,26). The femA, femB and femD factors are involved in peptidoglycan synthesis. The femA and femB genes are important in the formation of the pentaglycine bridge linking muropeptides (6,7). The femD gene (renamed glmM) encodes a phosphoglucosamine mutase (GlmM), involved in the formation of glucosamine-1-phosphate from glucosamine-6-phosphate (33,56). The femC factor is a regulatory gene (glnR) in the glutamine synthetase operon that is involved in amidation of glutamate residues (11,17); the femE gene seems to have only a marginal influence on resistance to methicillin and has not been characterised further (9,26).

A new peptidoglycan mutant RUSA235 (Ω711) was obtained through screening of a new Tn551 library constructed in the background of a highly methicillin-resistant *S. aureus* strain COL (26). This new insertion site is different from all previously described transposon mutants: the Tn551 insertion is located in the SmaI-B fragment of the chromosome; the insertion reduces the minimal inhibitory concentration (MIC) of the parental strain from 1600 to 25–50 $\mu$g ml$^{-1}$; the insertion causes a heterogeneous phenotype of methicillin resistance and a unique abnormality in peptidoglycan composition (26,44). This new mutant appears to be impaired in the biosynthesis of staphylococcal cell wall precursor muropeptide before the lysine addition step, as evidenced by the appearance of abnormal muramyl dipeptide residues in the peptidoglycan and by the accumulation of UDP-linked muramyl dipeptide and reduced levels of the UDP-linked muramyl pentapeptide in the cell wall precursor pool of the mutant (44).

Figure 11A:
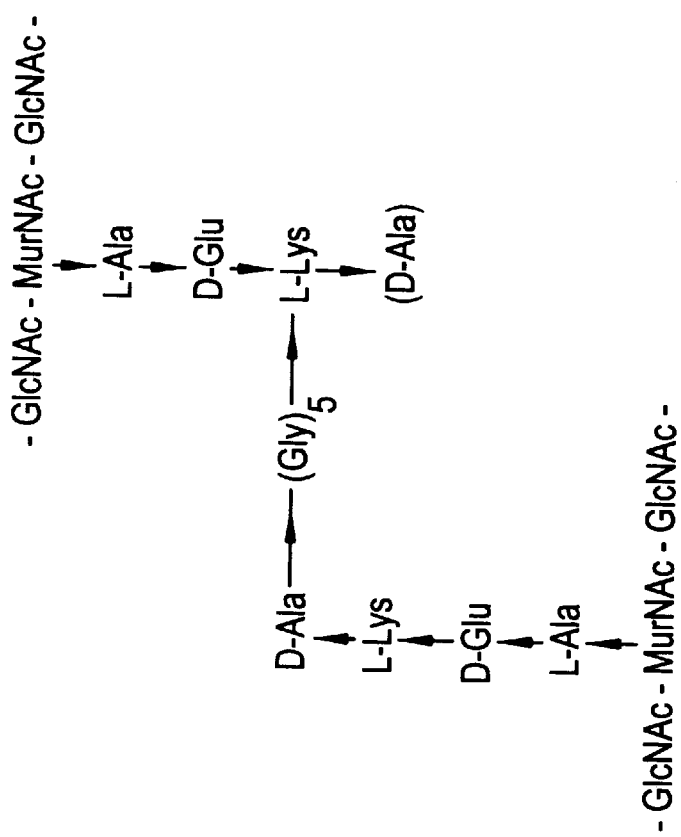
FIG. 11. Cross-linked peptidoglycan in B. subtilis and E. coli (a). Cross-linked peptidoglycan in S. aureus (b).
Figure 11B:
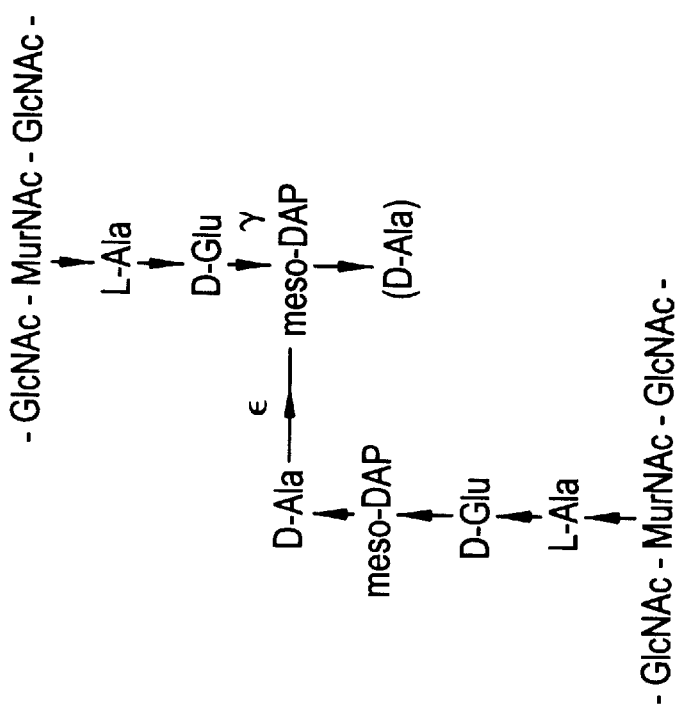

In the peptidoglycans of *Escherichia coli* and *Bacillus subtilis* the tetra- or pentapeptide side chains linked to N-acetylmuramic acid residues contain L-alanine, D-glutamate, meso-diaminopimelic acid, and terminate either in a D-alanine (if the peptide participates in a cross-link) or in the dipeptide D-alanyl-D-alanine (in the case of monomeric muropeptides) (FIG. 11a). In the muropeptides of the *S. aureus* peptidoglycan the meso-diaminopimelic acid is replaced by L-lysine (FIG. 11b). These cytoplasmic steps of the biosynthesis of bacterial peptidoglycan are catalysed by four ligases that promote the construction of the pentapetide side chain by stepwise addition of the amino acids. These ligases are encoded by the murC, murD, murE and murF genes (for a review see [54]) which, in *E. coli* (37) and *Haemophilus influenzae* (28), are organized in a large cluster of genes (DCW) that include other genes involved in peptidoglycan biosynthesis and cell division. In the three gram positive bacteria examined so far, the functionally analogous gene clusters are smaller: they lack the murC, murF and ddl genes in the case of *B. subtilis* (24,25,31), they lack murC, murF in the case of *Enterococcus faecalis* and in the case of *S. aureus* only murD is present, lacking the murC, murE, murF and murG genes (48).

In this example the cloning and sequencing of the Tn551 insertional region in the *S. aureus* mutant RUSA235 are described. Initially, the region of the chromosome of the mutant RUSA235 strain wherein the Tn551 inserted was referred to as femR235. Data disclosed herein, indicates femR235 contains the staphylococcal murE gene, which is inactivated in RUSA235. Additional characterization of other open reading frames in the vicinity of murE confirms the finding of Pucci et al. (48) that the murE gene is not part of a DCW cluster of *S. aureus* but rather it is located elsewhere on the staphylococcal chromosome.

Materials and Methods

Bacterial strains, phage and plasmids.

The strains and plasmids used in this study are listed in Table 8.

CHEF-DRII apparatus (BIO-RAD, Laboratories, Hercules, Calif.) for 20 hours at 14° C.; the voltage was set at 200V, ramped with initial forward time of 0.5 sec and final forward time of 1.5 sec. To purify DNA fragments from gels, β-Agarase (New England Bio Labs Inc., Hertfordshire, U.K.) was used according to the manufacturer's recommendations. The internal 4 Kb HpaI-XbaI fragment of the transposon Tn551, cloned in the plasmid pRT1 (15), was used as probe and labelled according to the ECL random prime labelling and detection systems purchased from Amersham Life Science (Buckinghamshire, UK) and according to the recommendation of the manufacturer.

DNA sequence analysis.

Double-strand sequencing was carried out with templates of DNA fragment cloned in pGEM-3Z. The oligonucleotide

TABLE 8

Strains, plasmids and vectors used in this study.

| Strains | Relevant characteristics | Source/reference |
|---|---|---|
| *S. aureus* COL | mecA - Homogeneous Mc$^r$ MIC 1,600 mg ml$^{-1}$ | RU collection |
| *S. aureus* RUSA 235 | COL::Tn551-Mc$^r$; Em$^r$ MIC 50 mg ml$^{-1}$ | (26) |
| *E.coli* TOP10 | F'{lacI$^q$Tet$^r$}mcrA D(mrr-hsdRMS-mcrBC) f80 lacZDM15 DlacX74 deoR recA 1 araD139 D(ara-leu)7697galK rpsL endA1 nupG | Invitrogen |
| *E. coli* XL1 Blue MRA | r$^-$ supE hsdR lac- F' proAB$^+$lacI lacZDM15 rec | Amersham |
| *E. coli* XL1 Blue MRA (P2) | *E. coli* XL1 Blue MRA, P2 lysogen | Amersham |
| Plasmids/lphage vectors | | |
| lDASH II srII5° red$^+$ gam$^+$ | l sbhl1° b189 KH54 chicC srI14°nin5 shndIII16° | Stratagene |
| lDII/R235E13 (femR235::Tn551) | lDASH II/13 kb EcoRI fragment from RUSA235 | in this study |
| pRT1 | pGEM-1/4.0kb XbaI/HpaI fragment of Tn551 | (15) |
| pGEM-3Z | subcloning vector Amp$^r$ | Promega Corp. |
| pAML1 (Tn551$_L$::femR235 flanking) | pGEM-3Z/5.5 kb SalI fragment from lDII/R235 | in this study |
| pAML3 (Tn551$_R$::femR235 flanking) | pGEM-3Z/7.5 kb SalI fragment from lDII/R235 | in this study |

Media and growth conditions.

The MRSA mutants were grown in Tryptic Soy Agar (TSA) or Tryptic Soy Broth (TSB) (Difco Laboratories, Detroit, Mich.) supplemented with erythromycin (10 g/ml$^{-1}$). Luria Bertani medium was used to propagate *Escherichia coli* TOP10

(Invitrogen Corporation, San Diego), and ampicillin (100 g ml$^{-1}$) was added for selection and maintenance of plasmids listed in Table 8. *E. coli* XL1-Blue MRA and *E. coli* XL1-Blue MRA (P2), the hosts of Lambda DASH II/EcoRI vector, were cultured as recommended by the manufacturer (Stratagene Cloning Systems, La Jolla, Calif.). Cultures were grown at 37° C. unless otherwise stated.

Susceptibility tests.

Overnight cultures grown in TSB at 37° C. with aeration were used for testing the expression of the methicillin resistance, using the method of population analysis in which various dilutions of bacterial cultures are plated on tryptic soy agar containing increasing concentrations of methicillin (26). Colonies were counted after incubation at 37° C. for 48 hours.

DNA manipulations.

All routine DNA manipulations were performed as in reference (20). The restriction enzymes and T4 ligase purchased from Stratagene Cloning Systems (La Jolla, Calif.) and the calf intestinal alkaline phosphatase from Boehringer Mannheim (GmbH Biochemicals, Mannheim, Germany), were used as recommended by manufacturers. The gels were prepared with 1% agarose (SeaKem, LE, FMC Bioproducts, Rockland, Me.) in 0.5× TBE buffer and were run in a primers were synthesized and purified by Gibco/BRL Life Technologies (Grand Island, N.Y.). The nucleotide and derived amino acid sequences were analysed with Wisconsin Genetic Computer Group (GCG) software. The alignments were determined by using the PileUp program of the GCG package, and the Prettybox program of the extension EGCG package of sequence analysis software.

Results

Figure 12A:
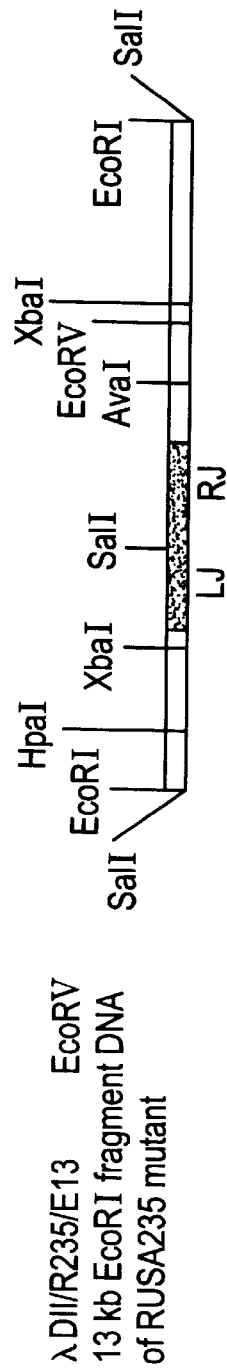
FIG. 12. Cloning and sequencing strategy of the RUSA235 EcoRI fragment. a) Restriction map of the EcoRI 13 kb insert in λDII/R235/E13; transposon Tn551 is shown in gray, and the left and right junctions are indicated. b) pAML3 is the sub-cloned left junction. c) pAML3 is the sub-cloned right junction. The small arrows indicate the sequencing strategy.
Figure 12B:
Figure 12C:
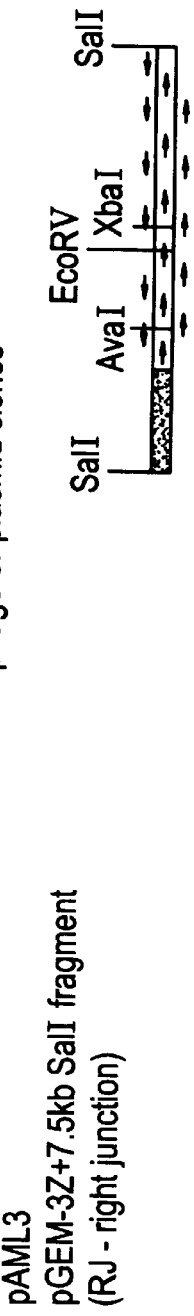

Cloning of the gene inactivated in the femR235 region (Ω711::Tn551). Insert Ω711 of the transposon Tn551 which generated the insertional mutant RUSA235 is located on a 7.7 kb EcoRI DNA fragment of the *S. aureus* strain COL. The approximately 13 kb EcoRI fragment (which includes the transposon Tn551) from strain RUSA235 was isolated and ligated with the lambda DASH II/EcoRI phage vector. The internal DNA fragment of Tn551 was purified from plasmid pRT1, labeled as described in the Methods, and was used as a probe to screen the EcoRI sublibrary of RUSA235 in the phage vector. The recombinant λ phage was named λDII/R235, and the physical mapping of the DNA insert was obtained by digestion with various restriction enzymes and Southern hybridization (FIG. 12a). The 5.5 kb and 7.5 kb SalI fragments, including the left and right junctions of the transposon, were subcloned into the SalI site of plasmid pGEM-3Z to obtain the recombinant plasmids pommel and pAML3, respectively (FIGS. 12b and 12c).

DNA sequence of the femR235 region.

The DNA sequence of the insertion Ω711 region of RUSA235 was determined by separately sequencing the DNA inserts of the pommel and pAML3 plasmids through both strands with the strategy of primer walking. Sequencing of the pommel insert was initiated with a Tn551 left junction based primer, the pAML3 insert was initiated with a Tn551 right junction based primer and six and nine more oligonucleotide primers, respectively, were subsequently synthesized as new sequences were identified in order to generate enough overlapping regions in the process of primer walking. The nucleotide sequence of the femR235 region—the 5757 bp HpaI/XbaI fragment—revealed three open reading frames (ORFs): ORF1 (391 amino acids) showing high degree of homology to the *B. subtilis* gene ypfP (47), ORF2 (492 amino acids), corresponding to murE, and ORF3 (511 amino acids), homologous to prfC, the peptide chain release factors (RF3) of *Dichelobacter* (*Bacteroides*) *nodosus* (23,35). The Tn551 insertion (Ω711) was located 3 bp upstream from the termination codon of the ORF2, which is 1472 nt from the initiation codon. ORF1 begins with the typical ATG initiation codon and ends with a TAA termination codon. The ribosome-binding site Using a FASTA search program (46) of GenBank, the deduced amino acid sequence of ORF2 (FIGS. 14A–B) was identified as a homologue of the MurE proteins from several microbial species (24,28,36,41,51) and it also showed homologies to MurF of *E. coli* (45) and *H. influenzae* (28) and MurC of *Bacillus subtilis* (55) (Table 9). Multiple amino acid sequence alignment of the amino acid sequence of ORF2 and the MurE proteins (FIG. 14) and their analysis revealed complete homology in highly conserved regions of the mur gene products (24,27). A motif GxxGK-2(T/S), near the amino acid residue 120, corresponding to a typical nucleotide fold, presumed to be involved in binding the ATP substrate (24,27,32,41,45,53) was observed in Region I. A hydrophobic patch near the amino acids 300, corresponding to Region IV, presents a specific consensus sequence: GxxNxxNxxAAxA-5x-G-18x-R. Two additional strongly conserved regions characteristic of most murein gene sequences were observed in the 175–219

TABLE 9

Percentages of amino acid identity between the predicted sequences of MurE of *Staphylococcus aureus* and similar proteins

| Proteins | Homolog species | Enzymes involved in the synthesis of the UDP-N-acetylmuramyl-pentapeptide | % Identity | Amino acid overlap |
| --- | --- | --- | --- | --- |
| MurE (*B.s*) | *Bacillus subtilis* (24) | UDP-N-acetylmuramyl-diaminopimelic acid ligase | 40.98% | 449 |
| MurE (*H.i*) | *Haemophylus influenzae* (11) | UDP-N-acetylmuramyl-diaminopimelic acid ligase | 33.66% | 496 |
| MurE (*E.c*) | *Escherichia coli* (40,41,51) | UDP-N-acetylmuramyl-diaminopimelic acid ligase | 30.20% | 490 |
| MurE (*P.a*) | *Pseudomonas aureginosa* (36) | UDP-N-acetylmuramyl-diaminopimelic acid ligase | 31.31% | 313 |
| MurF (*Hi*) | *Haemophylus influenzae* (28) | UDP-N-acetylmuramyl-D-alanyl-D-alanine ligase | 25.06% | 395 |
| MurF (*E.c*) | *Escherichia coli* (45) | UDP-N-acetylmuramyl-D-alanyl-D-alanine ligase | 25.47% | 365 |
| MurC (*B.s*) | *Bacillus subtilis* (55) | UDP-N-acetylmuramate-L-alanine ligase | 26.49% | 351 |

(GGAGGG, from 1729 to 1734 nt), −10 (TAAAAT, from 1767 to 1772 nt), and −35 (TTTATT, from 1788 to 1793 nt) for ORF1 were observed on the complementary strand of the DNA sequence in FIGS. 13A–F. ORF2 and ORF3 were also preceded by putative ribosome-binding-site sequences, beginning with the characteristic ATG initiation codon and ending with a TAA termination codon. In ORF2, the putative promotor sequences TTATTA for −35 region and TATAAT for −10 region were found 39 and 17 nucleotides, amino acids region. These murein gene sequences not only define regions of homology but also identify specific amino acids that seem to be important for either the folding or for the functioning in this family of murein genes. The specific sequences include generally hydrophobic amino acids containing a glutamate residue and—26 amino acids downstream—a Asp-Hist-aliphatic-His motif in Region II. Further downstream, in Region m composed of 230 amino acids, a short set of acidic residues (27) was identified (see FIGS. 14A–B).

TABLE 10

Percentages of amino acid identity between the predicted sequences of PrfC, a peptide chain release factor (RF3) of *Staphylococcus aureus*, and similar proteins

| Proteins | Homolog species | Enzymes involved in the formation of ribosomal termination complex | % Identity | Amino acid overlap |
| --- | --- | --- | --- | --- |
| PrfC (*B.n*) | *Dichelobacter nodosus* (23) | Peptide chain release factor (RF3) | 47.6% | 521 |
| PrfC (*H.i*) | *Haemophylus influenzae* (28) | Peptide chain release factor (RF3) | 46.4% | 528 |
| PrfC (*E.c*) | *Escherichia coli* (29,35,42) | Peptide chain release factor (RF3) | 45.07% | 528 | respectively, upstream of the Shine-Delgarno sequence. The analogous regions in ORF3, i.e., a putative TTGTTT −35 region and AATTGT −10 region, were found 89 and 72 nucleotides, respectively, upstream of the ribosome binding site (FIGS. 13A–F).

Comparison of amino acid sequences with known proteins.

Figure 15A:
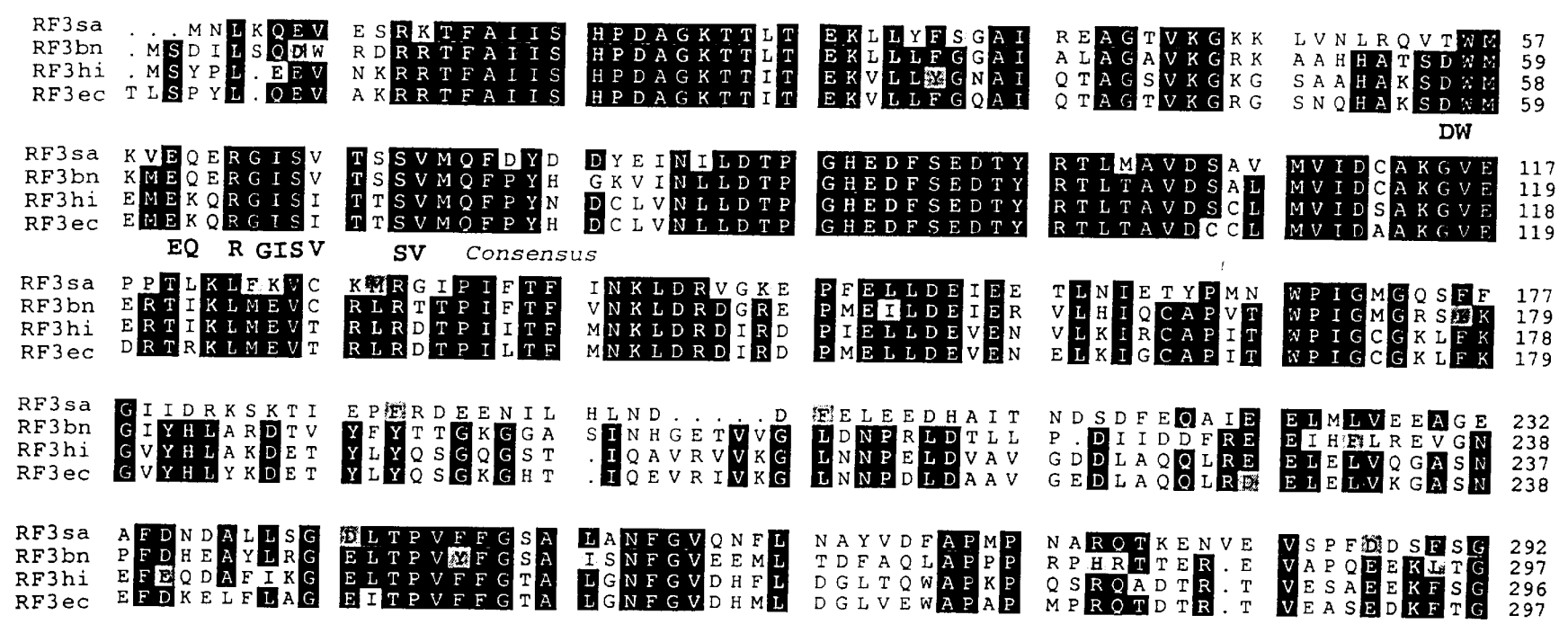
Figure 15B:
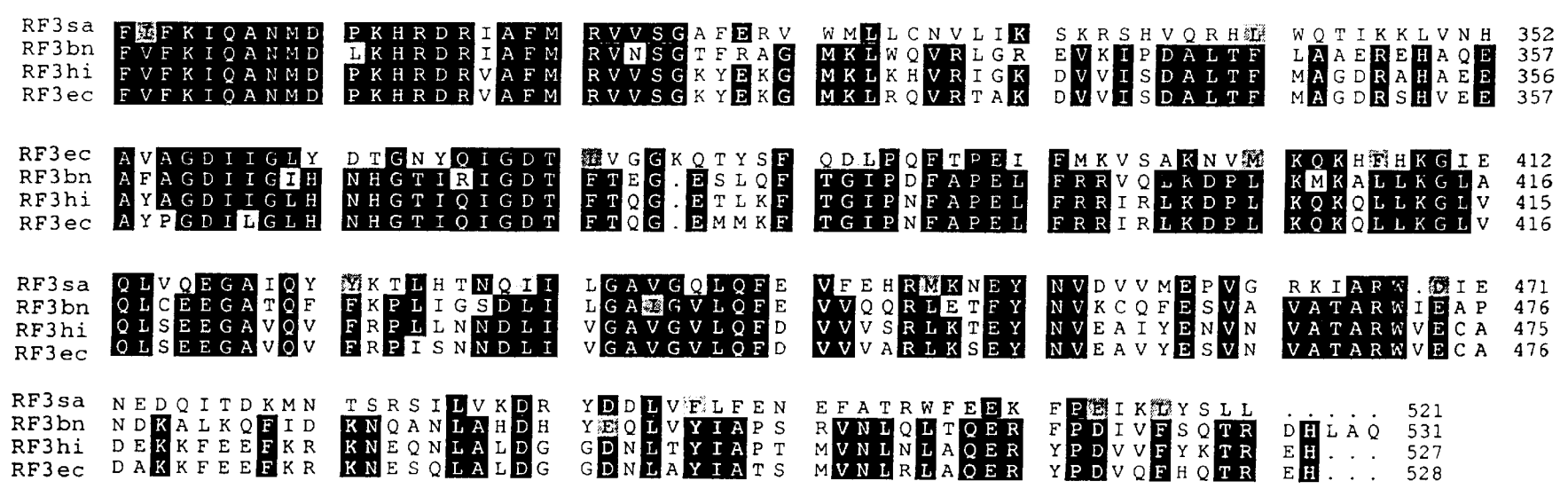
Figure 16A:
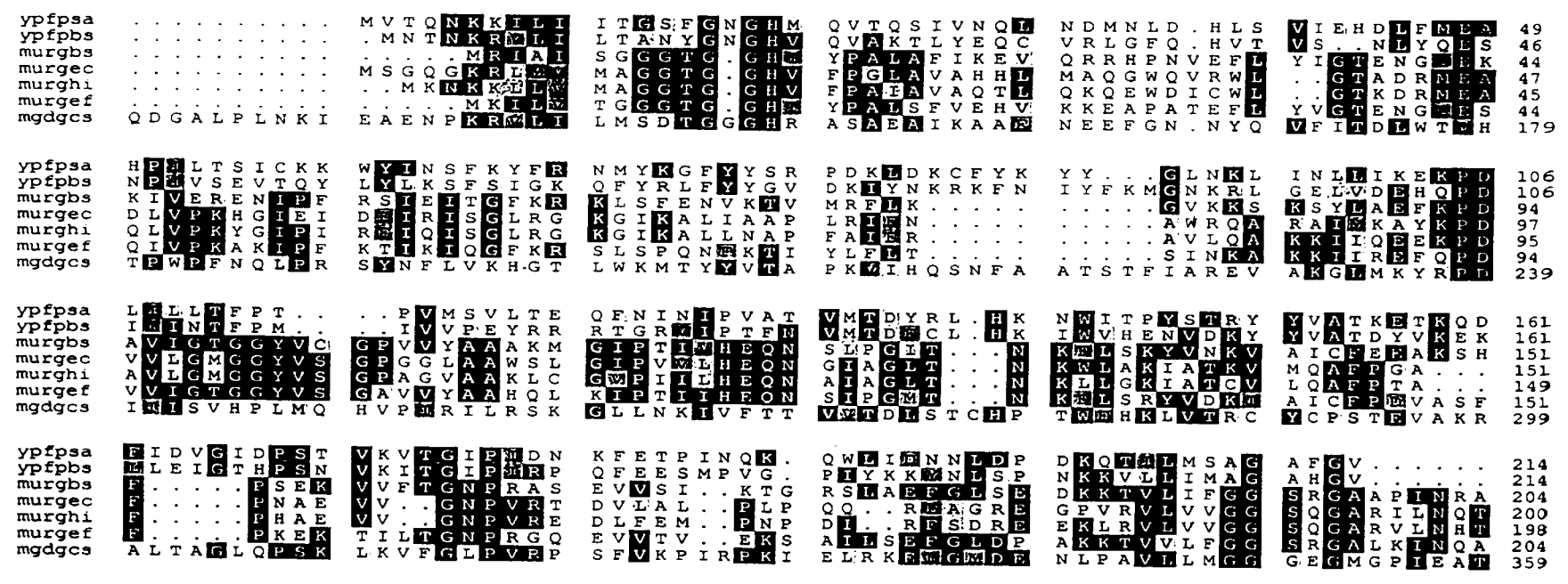
Figure 16B:
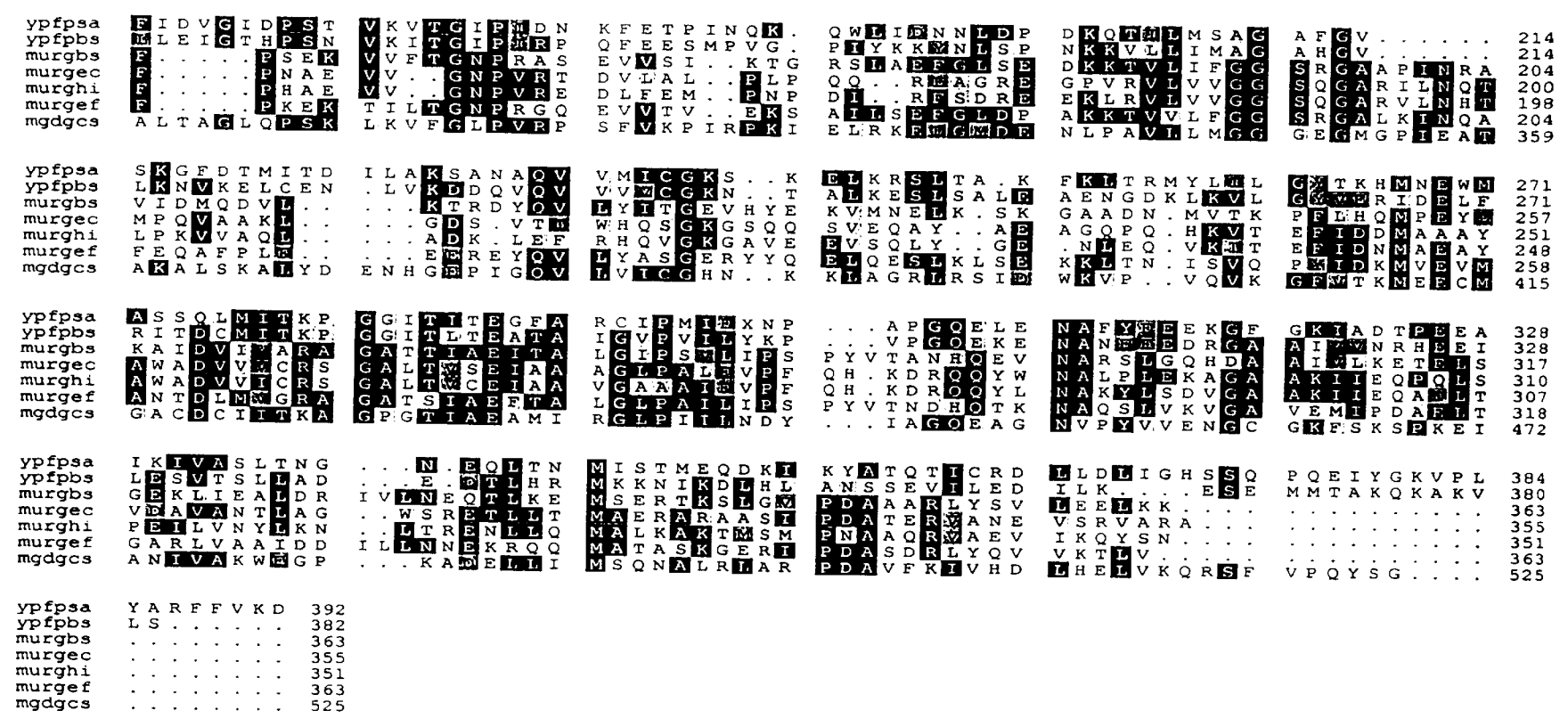

The ORF3 showed amino acid sequence identities with the peptide chain release factor 3 (RF3) of *D. nodosus*, *H. influenzae* and *E. coli* (Table 10). This protein, important for the termination of protein synthesis during translation (35, 42), has a GTP-binding motif, D(W)-3x-E(Q)x(R)(G)(I)(S)(V)-2x(S), that was observed in the 50–60 amino acid region of ORF3 product (FIGS. 15A–B). Upstream the ORF2 in the opposite direction, another open reading frame (ORF1) was identified (FIGS. 16A–B), the deduced amino acid sequence of which showed high homology to a 43.6 kd protein identified in *B. subtilis* as a nucleotide sugar transferase, the product of the ypfP gene (47), and to the murG genes of *B. subtilis* (43), *E. coli* (38), and *H. influenzae* (28) encoding N-acetylglucosaminyl transferases (Table 11). The sequence of all these genes has homology to the gene encoding MGDG synthase from *Cucumis sativus* (50). MGDG synthase is a UDP galactose-1,2-diacylglycerol 3β-D-galactosyl transferase, which transfers galactose from UDP galactose to 1,2-diacylglycerol (34).

which show homology only among the specific ligases in various bacterial strains. This observation suggests that the amino acid specificity of the ligases is probably encoded in the C-terminal regions of the Mur proteins (27). It is noteworthy that in the leaky mutant RUSA235 the insert is located in the C-terminal region of the murE gene. Our data suggest that this location of Tn551 in the murE of RUSA235 is directly or indirectly responsible for generating the drastic reduction of the minimal inhibitory concentration and heterogeneous methicillin resistance phenotype of the mutant. Whether or not the decreased methicillin resistance of mutant RUSA235 is related to the abnormal balance of

TABLE 11

Percentages of amino acid identity between the predicted sequences of YpfP of *Staphylococcus aureus* and similar proteins

| Proteins | Homolog species | Enzymes involved in the synthesis or modification of cell-wall | % Identity | Amino acid overlap |
|---|---|---|---|---|
| YpfP (*B.s*) | *Bacillus. subtilis* (47) | Nucleotide sugar transferase | 35.9% | 367 |
| MurG (*B.s*) | *Bacillus. subtilis* (43) | UDP-N-acetylglucosamine: N-acetylmuramyl-(pentaptide)pyrophosphoryl-Undecaprenol N-acetylglucosamine transferase | 23.63% | 220 |
| MurG (*E.c*) | *Escherichia coli* (32,38) | UDP-N-acetylglucosamine: N-acetylmuramyl-(pentaptide)pyrophosphoryl-Undecaprenol N-acetylglucosamine transferase | 20.66% | 271 |

Discussion

The biosynthesis of peptidoglycan begins in the cytoplasm with condensation of phosphoenolpyruvate and UDP-N-acetyl-glucosamine catalyzed by MurA and finishes across the plasma membrane in the periplasm with the transglycosylation and transpeptidation of the disaccharide pentapeptide monomers by the PBPs. The final product of the cytoplasmic steps is the assembly of the pentapeptide side chain by stepwise addition of amino acids to UDP-N-acetylmuramic acid (27). These ATP-dependent peptide-bond-forming reactions are catalyzed by MurC, MurD, MurE and MurF enzymes (for a review see 39 and 54).

In the staphylococcal auxiliary mutant RUSA235 described here, the Ω711 insertion site was located at the carboxy terminal of the murE gene. The insert appears to cause an abnormal transcription leading to the accumulation of UDP-linked muramyl dipeptide and reduced levels of UDP-muramyl pentapeptide in the cytoplasmic peptidoglycan precursors pool of RUSA235 (44).

Figure 14A:
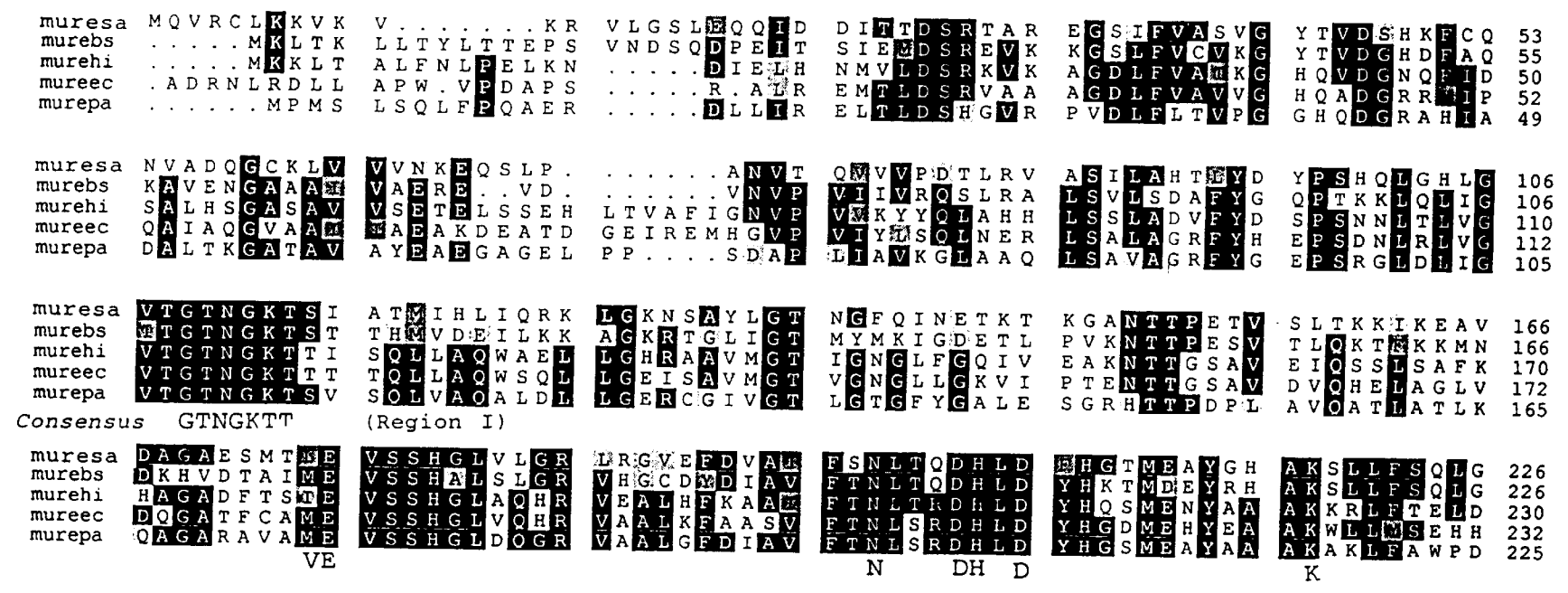
Figure 14B:
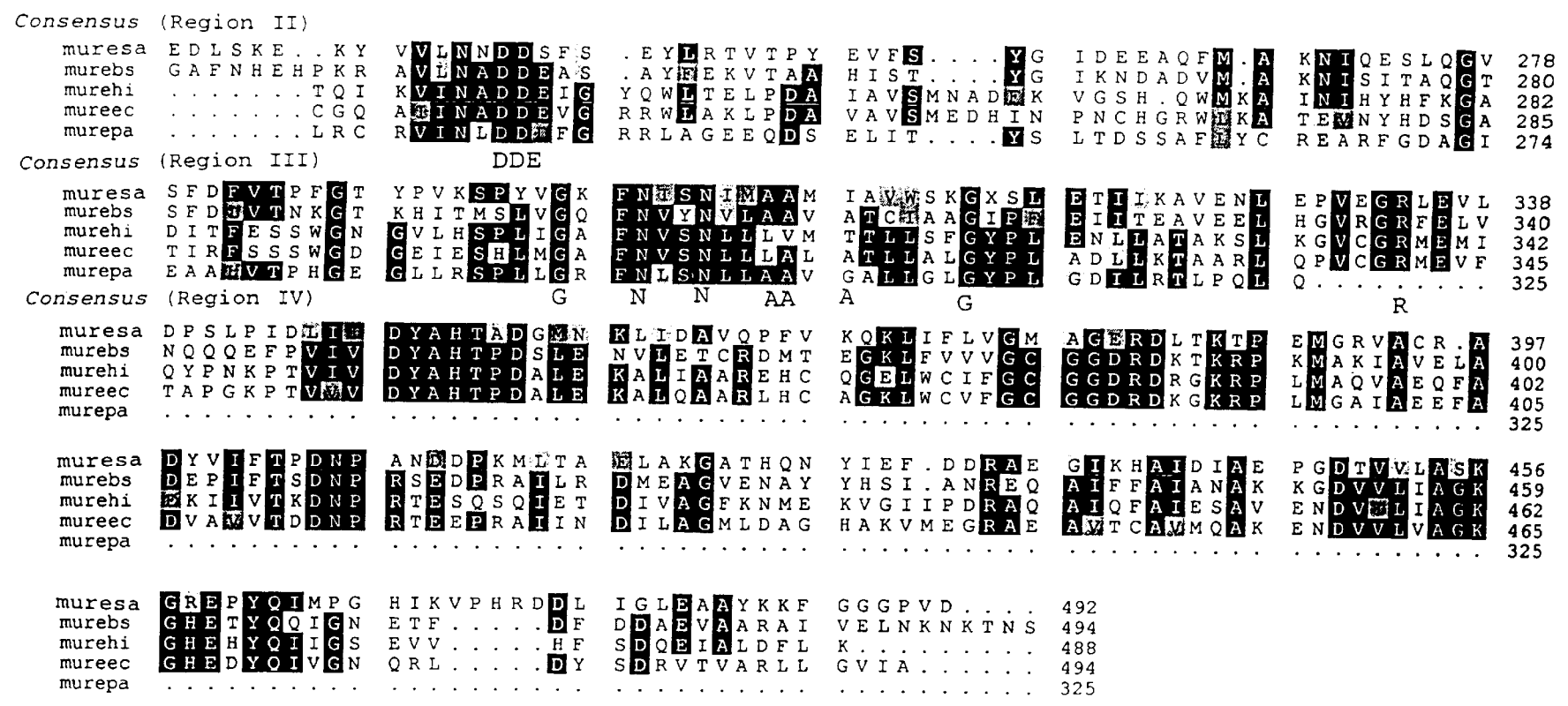

The results of the amino acids alignments indicate that the staphylococcal murE gene product has four highly conserved regions similar to those of homologous bacterial genes (FIGS. 14A–B). The specific amino acids strongly conserved in regions I–IV were observed in all members of the Mur protein family, in spite of the fact that each one of the proteins catalyses the ligation of chemically distinct amino acid to the growing stem peptide (27). One such region of homology includes the nucleotide binding motif that seems to be involved in ATP binding (FIGS. 14A–B—Region I). The synthetase activity of these proteins requires ATP hydrolysis, and a domain A characteristic of ATP binding proteins has been identified in all of the Mur proteins (24,27,32,41,45,53). Several other conserved residues, with less clear function, have also been identified in the staphylococcal MurE amino acid sequence, such as the entire Region II, except for the substitution of valine for leucine. The two asparagine residues of Region III are conserved, and in the Region IV there is a complete conservation of amino acid sequence.

In contrast to this apparent conservation of sequences in all the murE genes, the carboxy terminal portions of the Mur family of enzymes appears to contain unique sequences peptidoglycan precursors or to the incorporation of fraudulent, disaccharide dipeptide residues into the peptidoglycan of the mutant is not clear at the present time. It is expected that a complete inactivation of murE would be lethal and therefore the murE gene appears to be an attractive target for antibacterial chemotherapy (40). The structural and functional homologies of these Mur proteins open the possibility that a small-molecule inhibitor of more than one of these enzymes may be designed or discovered (27).

The murE of *S. aureus* identified in this communication is flanked by two open reading frames: ORF3 (downstream) with high degree of homology to the peptide chain release factor gene of *D. nodosus* (23,35,42) and ORF1 (upstream), a gene homologous to the ypfP of *B. subtilis* (47). Thus, murE is clearly not part of the DCW cluster of genes involved with other steps of peptidoglycan synthesis and cell division in *S. aureus* recently identified by Pucci et al. (48). The *B. subtilis* YpfP enzyme (similarly to the highly homologous MGDG synthetase of *Cucumis sativus* which transfers galactose from UDP-galactose to 1,2 diacylglycerol) (34) was proposed to function as a glucosamine transferase (47). It is conceivable that murE and its upstream neighbour represent part of another gene cluster involved with the staphylococcal envelope.

REFERENCES

1. Berger-Bäichi, B. 1983. Insertional inactivation of staphylococcal methicillin resistance by Tn551. J. Bacteriol. 154:479–487.
2. Berger-Bäichi, B., L. Barberis-Maino, A. Strassle, and F. H. Kayser. 1989. femA, a host-mediated factor essential for methicillin resistance in *Staphylococcus aureus*: molecular cloning and characterization. Mol. Gen. Genet. 219:263–269.
3. Berger-Bächi, B., A. Strassle, L. Barberis-Maino, W. Teach, C. Rafael, and F. H. Kayser. 1990. femA, a host-mediated trans-acting factor essential for methicillin resistance in *Staphylococcus aureus*. In Molecular Biology of the Staphylococci. (R. P. M. Novick, ed.). pp. 509–520, VCH Publishers, Inc., New York.
4. Berger-Bächi, B., A. Strassle, J E Gustafson, and F. H. Kayser. 1992. Mapping and characterization of multiple chromosomal factors involved in methicillin resistance in *Staphylococcus aureus*. Antimicrob. Agents Chemother. 36:1367–1373.
5. De Jonge, B. L. M., Y.-S. Chang, D. Gage, and A. Tomasz. 1992. Peptidoglycan composition of a highly methicillin-resistant *Staphylococcus aureus* strain: the role of penicillin binding protein 2A. J. Biol. Chem. 267:11248–11254.
6. De Jonge, B. L. M., Y.-S. Chang, D. Gage, and A. Tomasz. 1992. Peptidoglycan composition in heterogeneous Tn551 mutants of a methicillin resistant *Staphylococcus aureus* strain. J. Biol. Chem. 267:11255–11259.
7. De Jonge, B. L. M., T. Sidow, Y.-S. Chang, H. Labischinski, B. Berger-Bachi, D. A. Gage, and A. Tomasz. 1993. Altered muropeptide composition in *Staphylococcus aureus* strains with an inactivated femA locus. J. Bacteriol. 175:2779–2782.
8. De Lencastre, H., A. Figueiredo, K. Urban, J. Rahal, and A. Tomasz. 1991. Multiple mechanisms of methicillin resistance and improved methods for detection in clinical isolates of *Staphylococcus aureus*. Antimicrob. Agents Chemother. 35:632–639.
9. De Lencastre, H, B. L. M. de Jonge, P. R. Matthews, and A. Tomasz. 1994. Molecular aspects of methicillin resistance in *Staphylococcus aureus*. J. Antimicrob. Chemother. 33:7–24.
10. De Lencastre, H., I. Couto, I. Santos, J. Melo-Cristino, A. Torres-Pereira, and A. Tomasz. 1994. Methicillin-resistant *Staphylococcus aureus* disease in a Portuguese hospital: characterization of clonal types by a combination of DNA typing methods. Eur. J. Clin. Microbiol. Infect. Dis. 13:64–73.
11. Gustafson, J., A. Strassle, H. Hachler, F. H. Kayser, and B. Berger-Bachi. 1994. The femC locus of *Staphylococcus aureus* required for methicillin resistance includes the glutamine synthetase operon. J. Bacteriol. 176:1460–1467.
12. Hartman, B. J., and A. Tomasz. 1986. Expression of methicillin resistance in heterogeneous strains of *Staphylococcus aureus*. Antimicrob. Agents Chemother. 29:85–92.
13. Henze, U., T. Sidow, J. Wecke, H. Labischinski, and B. Berger-Bachi. 1993. Influence of femB on methicillin resistance and peptidoglycan metabolism in *Staphylococcus aureus*. J. Bacteriol. 175:1612–1620.
14. Kornblum, J., B. J. Hartman, R. P. M. Novick, and A. Tomasz. 1986. Conversion of a homogeneously methicillin resistant strain of *Staphylococcus aureus* to heterogeneous resistance, by Tn551-mediated insertional inactivation. Eur. J Clin. Microbiol. 5:714–718.
15. Matthews, P., and A. Tomasz. 1990. Insertional inactivation of the mec gene in a transposon mutant of a methicillin-resistant clinical isolate of *Staphylococcus aureus*. Antimicrob. Agents Chemother. 34:1777–1779.
16. Murakami, K., and A. Tomasz. 1989. Involvement of multiple genetic determinants in high-level methicillin-resistance in *Staphylococcus aureus*. J. Bacteriol. 171:874–879.
17. Ornelas-Soares, A., H. de Lencastre, B. de Jonge, D. Gage, Y.-S. Chang, and A. Tomasz. 1993. The peptidoglycan composition of a *Staphylococcus aureus* mutant selected for reduced methicillin resistance. J. Biol. Chem. 268:26268–26272.
18. Oshida, T., and A. Tomasz. 1992. Isolation and characterization of a Tn551-autolysis mutant of *Staphylococcus aureus*. J. Bacteriol. 174:4952–4959.
19. Pattee, P. A. 1981. Distribution of Tn551 insertion sites responsible for auxotrophy on the *Staphylococcus aureus* chromosome. J. Bacteriol. 145:479–488.
20. Sambrook, J., E. F. Fritsch, and T. Maniatis T (eds.). 1989. Molecular Cloning, A Laboratory Manual, 2nd edition. Cold Spring Harbor Laboratory Press, Cold Spring Harbor, N.Y.
21. Shaw, J. H., and D. B. Clewell. 1985. Complete nucleotide sequence of macrolide-lincosamine-streptogramin B-resistance transposon Tn917 in *Streptococcus faecalis*. J. Bacteriol. 164:782–796.
22. Tomasz, A. 1990. Auxiliary genes assisting in the expression of methicillin resistance in *Staphylococcus aureus*. In: Molecular Biology of the Staphylococci (R. P. M. Novick, ed.). pp. 565–583, VCH Publishers, Inc., New York.
23. Billington, S. J., B. H. Jost, and J. I. Rood. 1995. A gene region in *Dichelobacter nodosus* encoding a lipopolysaccharide epitope. Microbiology 141:945–957.
24. Daniel, R. A., and J. Errington. 1993. [DNA sequence of murE-murD region of *Bacillus subtilis* 168]. J. Gen. Microbiol. 139:361–370.
25. Daniel, R. A., A. M. Williams, and J. Errington. 1996. A complex four gene operon containing cell division gene pbpB in *Bacillus subtilis*. J. Bacteriol. 178:2343–2350.
26. De Lencastre, H., and A. Tomasz. 1994. Reassessment of the number of auxiliary genes essential for the expression of high level methicillin resistance in *Staphylococcus aureus*. Antimicrob. Agents Chemother. 38:2590–2598.
27. Eveland, S. S., D. L. Pompiliano, and M. S. Anderson. 1997. Conditionally lethal *Escherichia coli* murein mutants contain point defects that map to regions conserved among murein and folyl poly-γ-glutamate ligases: identification of a ligase super-family. Biochem. 36:6223–6229.
28. Fleischmann, R. D., M. D. Adams, O. White, R. A. Clayton, E. F. Kirkness, A. R. Kerlavage, C. J. Bult, J. F. Tomb, B. A. Dougherty, J. M. Merrick, K. McKenney, G. Sutton, W. Fitzhugh, C. A. Fields, J. D. Gocayne, J. D. Scott, R. Shirley, L.-I. Liu, A. Glodek, J. M. Kelley, J. F. Weidman, C. A. Phillips, T. Spriggs, E. Hedblom, M. D. Cotton, T. R. Utterback, M. C. Hanna, D. T. Nguyen, D. M. Saudek, R. C. Brandon, L. D. Fine, J. L. Fritchman, J. L. Fuhrmann, N. S. M. Geoghagen, C. L. Gnehm, L. A. McDonald, K. V. Small, C. M. Fraser, H. O. Smith, and J. C. Venter. 1995. Whole-genome random sequencing and assembly of *Haemophilus influenzae*. Science 269:496–512.
29. Grentzmann, G., D. Brechemier-Baey, V. Heurgue, L. Mora, and R. H. Buckingham. 1994. Localization and characterization of the gene encoding release factor RF3 in *Escherichia coli*. Proc. Natl. Acad. Sci. USA 91:5848–5852.
30. Hartman, B. J., and A. Tomasz. 1984. Low-affinity penicillin-binding protein associated with β-lactam resistance in *Staphylococcccus aureus*. J. Bacteriol. 158:513–516.
31. Henriques A. O., H. de Lencastre, and P. J. Piggot. 1992. A *Bacillus subtilis* morphogene cluster that includes spoVE is homologous to the mra region of *Escherichia coli*. Biochimie 74:735–748.
32. Ikeda, M., M. Wachi, H. K. Jung, F. Ishino, and M. Matsuhashi. 1990. Nucleotide sequence involving murG and murC in the mra gene cluster region of *Escherichia coli*. Nucleic Acids Research 18:4014.
33. Jolly L, S. Wu, J. van Heijenoort, H. de Lencastre, D. Mengin-Lecreulx, and A Tomasz 1997. The femR315 gene from *Staphylococcus aureus* the interruption of which results in reduced methicillin resistance encodes a phosphoglucosamine mutase. J. Bacteriol. 179:5321–5325.

34. Joyard, J., and R. Douce. 1987. Galactolipid synthesis, p. 215–274. In P. K. Stumpf (ed.), The biochemistry of plants. Academic Press, New York, N.Y.
35. Kawazu, Y., K. Ito, K. Matsumura, and Y. Nakamura. 1995. Comparative characterization of release factor RF3 genes of *Escherichia coli, Salmonella typhimurium* and *Dichelobacter nodosus*. J. Bacteriol. 177:5547–5553.
36. Liao, X., and R. E. W. Hancock. 1995. Cloning and characterization of the *Pseudomonas aeruginosa* pbpB gene encoding penicillin binding protein 3. Antimicrob. Agents Chemother. 39:1871–1874.
37. Mengin-Lecreulx, D., C. Parquet, L. R. Desviat, J. Plá, B. Flouret, J. A. Ayala, and J. van Heijenoort. 1989. Organization of the murE-murG region *Escherichia coli*: identification of the murD gene encoding the D-glutamic-acid-adding enzyme. J. Bacteriol. 171:6126–6134.
38. Mengin-Lecreulx, D., L. Texier, M. Rousseau, and J. van Heijenoort. 1991. The murG gene of *Escherichia coli* codes for UDP-N-acetylglucosamine:N-acetylmuramyl-(pentapeptide) pyrophosphoryl-undecaprenol N-acetylglucosamine transferase involved in the membrane steps of peptidoglycan synthesis. (1991). J. Bacteriol. 173:4625–4636
39. Mengin-Lecreulx, D. J. van Heijenoort, and J. T. Park. 1996. Identification of the mpl gene encoding UDP-N-acetylmuramate:L-alanyl-γ-D-glutamyl-meso-diaminopimelate ligase in *Escherichia coli* and its role in recycling of cell wall peptidoglycan. J. Bacteriol. 178:5347–5352.
40. Michaud, C., D. Mengin-Lecreulx, J. van Heijenoort, and D. Blanot. 1990. Overproduction, purification and properties of uridine-diphosphate-N-acetylmuramoyl-L-alanyl-D-glutamate:meso-2,6-diaminopimelate ligase from *Escherichia coli*. Eur. J. Biochem. 194:853–861.
41. Michaud, C., C. Parquet, B. Flouret, D. Blanot, and J. van Heijenoort. 1990. Revised interpretation of the sequence containing the murE gene encoding the UDP-N-acetylmuramyl-tripeptide synthetase of *Escherichia coli*. Biochem. J. Letters. 269:277–278.
42. Mikuni, O., K, Ito, J. Moffat, K. Matsumura, K. McCaughan, T. Nobukuni, W. Tate, and Y. Nakamura. 1994. Identification of the prfC gene, which encodes peptide-chain-release factor 3 of *Escherichia coli*. Proc. Natl. Acad. Sci. 91:5798–5802.
43. Miyao, A., A. Yoshimura, T. Sato, T. Yamamoto, G. Theeragool, and Y. Kobayashi. 1992. Sequence of *Bacillus subtilis* homolog of the *Escherichia coli* cell-division gene murG. Gene 118:147–148.
44. Omelas-Soares, A., H. de Lencastre, B. de Jonge, and A. Tomasz. 1994. Reduced methicillin resistance in a new *Staphylococcus aureus* transposon mutant that incorporates muramyl dipeptides into the cell wall peptidoglycan. J. Biol. Chem. 269:1–5.
45. Parquet, C., B. Flouret, D. Mengin-Lecreulx, and J. van Heijenoort. 1989. Nucleotide sequence of the murF gene encoding the UDP-MurNAc pentapeptide synthetase of *Escherichia coli*. Nucleic Acids Research 17: 5379.
46. Pearson, W. R., and J. Lipman. 1988. Improved tools for biological sequences comparisons. Proc. Natl. Acad. Sci. USA 85:2444–2448.
47. Price K. D, S. Roels, and R. Losick. 1997. A *Bacillus subtilis* gene encoding a protein similar to nucleotide sugar transferases influences cell shape and viability. J Bacteriol. 179:4959–4961.
48. Pucci, M. J., J. A. Thanassi, L. F. Discotto, R. E. Kessler, and T. J. Dougherty. 1997. Identification and characterization of cell wall-division gene clusters in pathogenic bacteria Gram positive cocci. J. Bacteriol. 179:5632–5635.
49. Reynolds, P. E., and C. Fuller. 1989. Methicillin-resistant strains of *Staphylococcus aureus*: Presence of identical additional penicillin-binding protein in all strains examined. FEMS Microbiol. Lett. 33:251–254.
50. Shimojima, M., H. Ohta, A. Iwamatsu, T. Masuda, Y. Shioi, and K. Takamiya. 1997. Cloning of the gene for monogalactosyldiacylglycerol synthase and its evolutionary origin. Proc. Natl. Acad. Sci. USA 94:333–337.
51. Tao, J. S., and E. E Ishiguro. 1989. Nucleotide sequence of the murE gene of *Escherichia coli* Can. J. Microbiol. 35:1051–1054.
52. Utsui, Y., and T. Yokota. 1985. Role of an altered penicillin-binding protein in methicillin- and cephem-resistant *Staphylococcus aureus*. Antimicrob. Agents Chemother. 28:397–403.
53. Vaganay, S., E. M. Tanner, J. van Heijenoort, and D. Blanot. 1996. Study of the reaction mechanism of the D-glutamic acid-adding enzyme from *Escherichia coli*. Microbial Drug Resistance 2:51–54.
54. Van Heijenoort, J. 1994. Biosynthesis of the peptidoglycan unit, pp.39–54. In J. M. Ghuysen and R. Hakenbeck (eds.), Bacterial cell wall. Elsevier Science B.V., Amsterdam.
55. Varon, D., M. S. Brody, and C. W. Price. 1996. *Bacillus subtilis* operon under the dual control of the general stress transcription factor sigma B and the sporulation transcription factor sigma H. Mol. Microbiol. 20:339–350.
56. Wu, S., H. De Lencastre, A. Sali, and A. Tomasz. 1996. A Phosphoglucomutase-like gene for optimal expression of methicillin resistance in *Staphylococcus aureus*: Molecular cloning and DNA sequencing. Microbiol. Drug Resistance 2:277–286.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

It is also to be understood that all base pair sizes given for nucleotides and all molecular weight information for proteins are approximate and are used for the purpose of description.

Various references are cited throughout this specification, each of which is incorporated herein by reference in its entirety.

What is claimed is:

1. An isolated polynucleotide fragment selected from the group consisting of
   (a) a polynucleotide fragment consisting of the polynucleotide of SEQ ID No:1;
   (b) a polynucleotide fragment consisting of residues 2210 to 3634 of SEQ ID No:1; and
   (c) a polynucleotide fragment consisting of a coding region encoding the polypeptide of SEQ ID No:2.

2. A recombinant vector comprising the isolated nucleic acid of claim 1 operatively associated with a promoter.

3. A bacterial cell comprising the recombinant vector of claim 2.

4. A mutant *Staphylococcus aureus* strain characterized by:
   a) increased sensitivity to an antibiotic to which a parent of the mutant strain is resistant; and
   b) location of the mutation in the murE gene which encodes the protein UDP-N-acetylmuramoyl-L-alanyl-D-glutamate:L-lysine ligase.

5. The mutant strain of claim 4 in which the antibiotic is a beta lactam antibiotic.

6. The mutant strain of claim 5 in which the antibiotic is methicillin.

7. The mutant strain of claim 4 in which the mutation is caused by insertion of transposon Tn551.

8. An isolated polynucleotide fragment consisting of the coding region from the *Staphylococcus aureus* murE gene which encodes a UDP-N-acetylmuramoyl-L-alanyl-D-glutamate:L-lysine ligase.

9. A recombinant vector comprising the isolated nucleic acid of claim 8 operatively associated with a promoter.

10. A bacterial cell comprising the recombinant vector of claim 9.

11. An isolated polynucleotide fragment consisting of a coding sequence encoding a polypeptide having UDP-N-acetylmuramoyl-L-alanyl-D-glutamate:L-lysine ligase activity wherein said fragment hybridizes to the polynucleotide of SEQ ID No:1 in 50% formamide at 42° C.

12. A recombinant vector comprising the isolated nucleic acid of claim 11 operatively associated with a promoter.

13. A bacterial cell comprising the recombinant vector of claim 12.

* * * * *

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
       (A) LENGTH: 5757 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (vi) ORIGINAL SOURCE:
       (A) ORGANISM: Staphylococcus aureus (xi) SEQUENCE DESCRIPTION: SEQ ID NO:1:

```
GTTAACTTTA CATCGACAAA ATAATATAAT ATCCATGCAA TTAAAACGAC TAAAGACATC      60

ATGAAGGCAA AGCGTGTTGG GTGCACTTTG ATAAGTAGAT TCATAAAAAC CATACCTACC     120

AATAGGCCTA ACAACCATGA AAAATAAACA TAGCCCATTT GTTTGCCACG TTTATCTTCT     180

TCAACACTGG ATAACATAAT GACCCAAATA GGACTAACTG CAATACCGAA CATCATAGCA     240

CTAAATATGA TTACAAAAGG TGATGCTGGG AAACCAAATA ACTAAAAATA AACTTGTTAA     300

TGCTAAAATA AATCCAGCGT TAAAACGATT TTTGTGCCGA ATTTTTTCAG TAAAAATCCT     360

ATAACAAAGT TTGTAGATGC ATCAGCAATA AAATGTATTG AAAATGCTAG AGACGTTATT     420

GCTACAGCAA TGGATGTAAC TGTTGGCAAG AAATTAATAT AGCTTAGGAT ATACATGCCT     480

CTCGCAAATT CCATTAAAAA TAAGATAATA AGCATTAAAA TGAAATTTTT ATGATTAGCG     540

TAATTATTTA ACGAAGAATC TTGCATATAA AGGAACCTTT CCATAAATCT CTTGTGGTTG     600

TGATGAATGA CCGATTAAAT CAAGTAAGTC TCGACATATT GTCTGTGTAG CATACTTAAT     660

TTTATCTTGT TCCATTGTAC TAATCATGTT AGTTAATTGC TCATTACCGT TAGTTAAACT     720

TGCTACAATT TTTATTGCTT CTTCTGGAGT ATCAGCGATT TTACCAAAAC CTTTTTCTTC     780

AAAGTAAAAG GCATTTTCAA GCTCTTGACC AGGTGCAGGA TTTAAGAAAA TCATTGGAAT     840

ACAACGGGCG AAACCTTCAG TTATTGTGAT ACCACCAGGT TCGTAATCA TAAGTTGACT     900

TGATGCCATC CATTCATTCA TGTGTTTGGT ATAACCTAGA ATCAAATACA TTCTCGTTAA     960

TTTAAACTTA GCTGTTAAAG AACGCTTTAG CTCTTTGCTC TTACCACAAA TCATAACTAC    1020

TTGTGCATTT GCACTTTTCG CTAATATATC AGTAATCATC GTGTCAAAAC CTTTAGATAC    1080

ACCAAATGCA CCAGCTGACA TTAAAATAGT TTGCTTATCT GGATCTAAGT TGTTGTCTAT    1140

TAACCACTGC TTTTGATTAA TAGGCGTTTC AAATTTGTTA TCAATAGGAA TACCTGTCAC    1200

TTTAACTGTT GAAGGATCAA TACCTACGTC TATGAAGTCT TGTTTCGTTT CTTTTGTTGC    1260

CACATAATAT CTTGTTGAAT ACGGCGTAAT CCAGTTTTTA TGTAAGCGAT AGTCTGTCAT    1320

CACTGTAGCA ACTGGAATAT TAATGTTAAA TTGCTCAGTT AGTACCGACA TAACTGGTGT    1380

AGGAAACGTT AATAATATTA AATCTGGCTT TTCTTTTATC AATAAATTAA TTAACTTATT    1440

AAGTCCATAG TATTTGTAAA AACATTTGTC TAGTTTATCT GGGCGGCTGT AATAAAACCC    1500

TTTGTACATA TTTCTAAAAT ATTTAAAGCT ATTGATATAC CATTTTTTAC AAATAGAAGT    1560

CAAAATTGGA TGAGCTTCCA TAAATAAATC GTGCTCAATG ACGCTTAAAT GGTCTAGATT    1620
```

```
CATATCATTA AGTTGATTAA CGATACTCTG TGTAACTTGC ATATGACCGT TACCGAATGA    1680

GCCAGTAATA ATCAATATCT TTTTATTTTG AGTAACCATT AATAGCCACC CTCCGTTAGT    1740

TTGAAAATTT TATTTAAGTG TAACTTATTT TACGGCATTA TAAAAGAAAT AAAGACGCAA    1800

AGTCGTTACA TTTATAGCAA TTTTAATCTA TAGATGAATT GATACAAAAT AAAACGTTAT    1860

TTTATAAAGC AATTTATTGT TCTATGTTTT ATTTGTATAT TTAAAATTAT CCAGTATACA    1920

ATTATAGCAT ATTTTTGGAA ACAATTATGA TATTATACCA TGTTACAAGA TGGTTTTAAT    1980

AATTTAAGAT GAGCCATAAT TGTAAAACTA ATTCATAATA CCGTATGTTT TATTTTTAAT    2040

AGTAGAAATT AGAAAATGCT GATTAGTAGG ATATAACAGT GAAATTATAA ATTTATTAAC    2100

ATCAACAAAA CGTGTATAAT AAACATATTG TAGAAAAAGG AGCGGTTCAG TTTGGATGCA    2160

AGTACGTTGT TTAAAGAAAG TAAAAGTAAA GCGTGTATTG GGTTCTTTAG AACAACAAAT    2220

AGATGATATC ACTACTGATT CACGTACAGC GAGAGAAGGT AGCATTTTTG TCGCTTCAGT    2280

TGGATATACT GTAGACAGTC ATAAGTTCTG TCAAAATGTA GCTGATCAAG GGTGTAAGTT    2340

GGTAGTGGTC AATAAAGAAC AATCATTACC AGCTAACGTA ACACAAGTGG TTGTGCCGGA    2400

CACATTAAGA GTAGCTAGTA TTCTAGCACA CACATTATAT GATTATCCGA GTCATCAGTT    2460

AGGACATTTG GGTGTAACGG GTACAAATGG TAAAACTTCT ATTGCGACGA TGATTCATTT    2520

AATTCAAAGA AAGTTAGGAA AAAATAGTGC ATATTTAGGA ACTAATGGTT TCCAAATTAA    2580

TGAAACAAAG ACAAAAGGTG CAAATACGAC ACCAGAAACA GTTTCTTTAA CTAAGAAAAT    2640

TAAAGAAGCA GTTGATGCAG GCGCTGAATC TATGACATTA GAAGTATCAA GCCATGGCTT    2700

AGTATTAGGA CGACTGCGAG GCGTTGAATT TGACGTTGCA ATATTTTCAA ATTTAACACA    2760

AGACCATTTA GATTTTCATG GCACAATGGA AGCATACGGA CACGCGAAGT CTTTATTGTT    2820

TAGTCAATTA GGTGAAGATT TGTCGAAAGA AAAGTATGTC GTGTTAAACA ATGACGATTC    2880

ATTTTCTGAG TATTTAAGAA CAGTGACGCC TTATGAAGTA TTTAGTTATG GAATTGATGA    2940

GGAAGCCCAA TTTATGGCTA AAAATATTCA AGAATCTTTA CAAGGTGTCA GCTTTGATTT    3000

TGTAACGCCT TTTGGAACTT ACCCAGTAAA ATCGCCTTAT GTTGGTAAGT TTAATATTTC    3060

TAATATTATG GCGGCAATGA TTGCGGTGTG GAGTAAAGGT AAATCTTTAG AAACGATTAT    3120

TAAAGCTGTT GAAAATTTAG AACCTGTTGA AGGGCGATTA GAAGTTTTAG ATCCTTCGTT    3180

ACCTATTGAT TTAATTATCG ATTATGCACA TACAGCTGAT GGTATGAACA AATTAATCGA    3240

TGCAGTACAG CCTTTTGTAA AGCAAAAGTT GATATTTTTA GTTGGTATGG CAGGCGAACG    3300

TGATTTAACT AAAACGCCTG AAATGGGGCG AGTTGCCTGT CGTGCAGATT ATGTCATTTT    3360

CACACCGGAT AATCCGGCAA ATGATGACCC GAAAATGTTA ACGGCAGAAT TAGCCAAAGG    3420

TGCAACACAT CAAAACTATA TTGAATTTGA TGATCGTGCA GAAGGGATAA ACATGCAAT    3480

TGACATAGCT GAGCCTGGGG ATACTGTCGT TTTAGCATCA AAAGGAAGAG AACCATATCA    3540

AATCATGCCA GGGCATATTA AGGTGCCACA TCGAGATGAT TTAATTGGCC TTGAAGCAGC    3600

TTACAAAAAG TTCGGTGGTG GCCCTGTTGA TTAATAAAAG ATTTATTGAT GAAGGTAAAA    3660

CTATTGATGT TTATTTATTC GAAGCATTAA ATAACCAGAT AATCATTGCT ATACCAGATT    3720

GGTTTTGGTC ATATCAGATG GCAATGACAT TAGATGAAGA AACTTGTTTT GAAGCAATAC    3780

TCATGCAATT GTTTGTTTTT AAAGAAGAGG AAGAGGCAGA ATCGATTGCA TCACAACTAA    3840

CAGATTGGAT AGAAACATAT AAAAAGGAGA AAGACTAATG AACTTAAAGC AAGAAGTTGA    3900

GTCTAGAAAG ACTTTTGCGA TTATTTCACA TCCCGATGCA GGGAAAACAA CGTTAACTGA    3960

AAAACTATTG TACTTCAGTG GTGCTATTCG TGAAGCGGGT ACAGTTAAAG GGAAGAAACT    4020
```

```
GGTAAATTTG CGACAAGTGA CTTGGATGAA AGTTGAACAA GAACGTGGTA TTTCTGTAAC    4080

TAGTTCAGTA ATGCAATTTG ATTACGATGA TTATGAAATC AATATCTTAG ATACCCCAGG    4140

ACATGAAGAC TTTTCAGAAG ATACATATAG AACATTAATG GCAGTTGACA GTGCTGTCAT    4200

GGTCATAGAC TGTGCAAAAG GTGTTGAACC ACCAACATTG AAATTATTTA AGTTTGTAA     4260

AATGCGTGGT ATTCCAATCT TTACATTCAT TAATAAATTA GACCGAGTAG GTAAAGAACC    4320

ATTTGAATTA TTAGATGAAA TCGAAGAGAC ATTAAATATT GAAACATACC CTATGAATTG    4380

GCCAATTGGT ATGGGACAAA GTTTCTTTGG CATCATTGAT AGAAAGTCTA AAACAATTGA    4440

ACCATTTAGA GATGAAGAAA ATATATTACA TTTGAATGAT GATTTTGAGT TGGAAGAAGA    4500

TCATGCAATT ACAAATGATA GTGATTTTGA ACAAGCGATT GAAGAATTAA TGTTGGTTGA    4560

AGAAGCGGGT GAAGCCTTTG ATAATGACGC GCTGTTGAGT GGAGACTTAA CACCTGTATT    4620

TTTCGGTTCA GCTTTAGCTA ACTTTGGTGT ACAAAATTTC TTAAATGCAT ATGTTGATTT    4680

TGCGCCCATG CCAAATGCGA GACAAACAAA AGAAACGTT GAAGTAAGCC CGTTTGATGA     4740

TTCATTTTCA GGATTTATCT TTAAAATTCA AGCCAACATG GACCCTAAAC ACCGTGATAG    4800

AATTGCCTTT ATGCGTGTCG TTAGTGGTGC ATTTGAACGT GTATGGATGT TACTTTGCAA    4860

CGTACTAATA AAAAGCAAAA GATCACACGT TCAACGTCAT TTATGGCAGA CGATAAAGAA    4920

ACTGGTGAAT CATGCTGTAG CAGGCGATAT CATTGGACTA TATGATACTG GTAATTATCA    4980

AATTGGAGAT ACTTTAGTTG GTGGAAAACA AACCTACAGT TTCCAAGATT TACCACAATT    5040

TACGCCAGAA ATTTTTATGA AAGTTTCTGC TAAAAACGTC ATGAAACAGA AGCATTTCCA    5100

TAAAGGTATT GAACAATTAG TACAAGAAGG TGCGATTCAA TACTATAAAA CATTACACAC    5160

AAACCAAATT ATTTTAGGTG CTGTTGGTCA GTTACAATTT GAAGTTTTCG AACATAGAAT    5220

GAAAAACGAA TATAATGTTG ATGTTGTTAT GGAGCCAGTA GGCCGTAAAA TTGCACGTTG    5280

GGACATTGAA AATGAAGACC AAATTACAGA TAAGATGAAC ACATCAAGAT CGATTTTAGT    5340

GAAAGATAGA TATGACGATT TAGTATTCTT ATTTGAAAAT GAATTTGCAA CAAGATGGTT    5400

TGAAGAGAAA TTCCCTGAAA TTAAATTGTA TAGTTTACTT TAACAGCTCA ATTGTATAAT    5460

CGAATTTGTT ACATTAAAAA TAATTGTTTC GTTGAAGAAA AATAAATTGT ATATTTTAAA    5520

AGAAAAAGGT ATACTATGAT GTATCAAATG AATAACCTAT GGCATTTTGT CAGAGGGGAG    5580

TAACTTAAGA ATCATGACCG TATAAATGAT TCGACACTTT ATCGTCATTA CGAAGATATC    5640

TTCCGGTAAA GTGGGCAATT AAATTGCTTA GTGAGACCTT TGCTATTTAT TTAGCATAGG    5700

TCTTTTTGTT TGTACTTAAC TTATTTATTT AAAGGAGTTG TACATGTTAA TGGATCC       5757
```

(2) INFORMATION FOR SEQ ID NO:2:

(i) SEQUENCE CHARACTERISTICS:
        (A) LENGTH: 492 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Staphylococcus aureus (xi) SEQUENCE DESCRIPTION: SEQ ID NO:2:

```
Met Gln Val Arg Cys Leu Lys Lys Val Lys Val Lys Arg Val Leu Gly
1               5                   10                  15
```

-continued

```
Ser Leu Glu Gln Gln Ile Asp Asp Ile Thr Thr Asp Ser Arg Thr Ala
             20                  25                  30

Arg Glu Gly Ser Ile Phe Val Ala Ser Val Gly Tyr Thr Val Asp Ser
         35                  40                  45

His Lys Phe Cys Gln Asn Val Ala Asp Gln Gly Cys Lys Leu Val Val
         50                  55                  60

Val Asn Lys Glu Gln Ser Leu Pro Ala Asn Val Thr Gln Val Val Val
 65                  70                  75                  80

Pro Asp Thr Leu Arg Val Ala Ser Ile Leu Ala His Thr Leu Tyr Asp
                 85                  90                  95

Tyr Pro Ser His Gln Leu Gly His Leu Gly Val Thr Gly Thr Asn Gly
             100                 105                 110

Lys Thr Ser Ile Ala Thr Met Ile His Leu Ile Gln Arg Lys Leu Gly
         115                 120                 125

Lys Asn Ser Ala Tyr Leu Gly Thr Asn Gly Phe Gln Ile Asn Glu Thr
         130                 135                 140

Lys Thr Lys Gly Ala Asn Thr Thr Pro Glu Thr Val Ser Leu Thr Lys
145                 150                 155                 160

Lys Ile Lys Glu Ala Val Asp Ala Gly Ala Glu Ser Met Thr Leu Glu
                 165                 170                 175

Val Ser Ser His Gly Leu Val Leu Gly Arg Leu Arg Gly Val Glu Phe
             180                 185                 190

Asp Val Ala Ile Phe Ser Asn Leu Thr Gln Asp His Leu Asp Phe His
         195                 200                 205

Gly Thr Met Glu Ala Tyr Gly His Ala Lys Ser Leu Leu Phe Ser Gln
     210                 215                 220

Leu Gly Glu Asp Leu Ser Lys Glu Lys Tyr Val Val Leu Asn Asn Asp
225                 230                 235                 240

Asp Ser Phe Ser Glu Tyr Leu Arg Thr Val Thr Pro Tyr Glu Val Phe
                 245                 250                 255

Ser Tyr Gly Ile Asp Glu Glu Ala Gln Phe Met Ala Lys Asn Ile Gln
             260                 265                 270

Glu Ser Leu Gln Gly Val Ser Phe Asp Phe Val Thr Pro Phe Gly Thr
         275                 280                 285

Tyr Pro Val Lys Ser Pro Tyr Val Gly Lys Phe Asn Ile Ser Asn Ile
     290                 295                 300

Met Ala Ala Met Ile Ala Val Trp Ser Lys Gly Xaa Ser Leu Glu Thr
305                 310                 315                 320

Ile Ile Lys Ala Val Glu Asn Leu Glu Pro Val Glu Gly Arg Leu Glu
                 325                 330                 335

Val Leu Asp Pro Ser Leu Pro Ile Asp Leu Ile Ile Asp Tyr Ala His
             340                 345                 350

Thr Ala Asp Gly Met Asn Lys Leu Ile Asp Ala Val Gln Pro Phe Val
         355                 360                 365

Lys Gln Lys Leu Ile Phe Leu Val Gly Met Ala Gly Glu Arg Asp Leu
     370                 375                 380

Thr Lys Thr Pro Glu Met Gly Arg Val Ala Cys Arg Ala Asp Tyr Val
385                 390                 395                 400

Ile Phe Thr Pro Asp Asn Pro Ala Asn Asp Asp Pro Lys Met Leu Thr
                 405                 410                 415

Ala Glu Leu Ala Lys Gly Ala Thr His Gln Asn Tyr Ile Glu Phe Asp
             420                 425                 430
```

-continued

```
Asp Arg Ala Glu Gly Ile Lys His Ala Ile Asp Ile Ala Glu Pro Gly
            435                 440                 445

Asp Thr Val Val Leu Ala Ser Lys Gly Arg Glu Pro Tyr Gln Ile Met
            450                 455                 460

Pro Gly His Ile Lys Val Pro His Arg Asp Asp Leu Ile Gly Leu Glu
465                 470                 475                 480

Ala Ala Tyr Lys Lys Phe Gly Gly Gly Pro Val Asp
            485                 490
```

(2) INFORMATION FOR SEQ ID NO:3:

(i) SEQUENCE CHARACTERISTICS:
        (A) LENGTH: 494 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Bacillus subtilis (xi) SEQUENCE DESCRIPTION: SEQ ID NO:3:

```
Met Lys Leu Thr Lys Leu Leu Thr Tyr Leu Thr Thr Glu Pro Ser Val
1               5                   10                  15

Asn Asp Ser Gln Asp Pro Glu Ile Thr Ser Ile Glu Met Asp Ser Arg
            20                  25                  30

Glu Val Lys Lys Gly Ser Leu Phe Val Cys Val Lys Gly Tyr Thr Val
            35                  40                  45

Asp Gly His Asp Phe Ala Gln Lys Ala Val Glu Asn Gly Ala Ala Ala
            50                  55                  60

Ile Val Ala Glu Arg Glu Val Asp Val Asn Val Pro Val Ile Ile Val
65                  70                  75                  80

Arg Gln Ser Leu Arg Ala Leu Ser Val Leu Ser Asp Ala Phe Tyr Gly
            85                  90                  95

Gln Pro Thr Lys Lys Leu Gln Leu Ile Gly Ile Thr Gly Thr Asn Gly
            100                 105                 110

Lys Thr Ser Thr Thr His Met Val Asp Glu Ile Leu Lys Lys Ala Gly
            115                 120                 125

Lys Arg Thr Gly Leu Ile Gly Thr Met Tyr Met Lys Ile Gly Asp Glu
            130                 135                 140

Thr Leu Pro Val Lys Asn Thr Thr Pro Glu Ser Val Thr Leu Gln Lys
145                 150                 155                 160

Thr Phe Lys Lys Met Asn Asp Lys His Val Asp Thr Ala Ile Met Glu
            165                 170                 175

Val Ser Ser His Ala Leu Ser Leu Gly Arg Val His Gly Cys Asp Tyr
            180                 185                 190

Asp Ile Ala Val Phe Thr Asn Leu Thr Gln Asp His Leu Asp Tyr His
            195                 200                 205

Lys Thr Met Asp Glu Tyr Arg His Ala Lys Ser Leu Leu Phe Ser Gln
            210                 215                 220

Leu Gly Gly Ala Phe Asn His Glu His Pro Lys Arg Ala Val Leu Asn
225                 230                 235                 240

Ala Asp Asp Glu Ala Ser Ala Tyr Phe Glu Lys Val Thr Ala Ala His
            245                 250                 255

Ile Ser Thr Tyr Gly Ile Lys Asn Asp Ala Asp Val Met Ala Lys Asn
```

```
                    260                 265                 270
Ile Ser Ile Thr Ala Gln Gly Thr Ser Phe Asp Leu Val Thr Asn Lys
            275                 280                 285

Gly Thr Lys His Ile Thr Met Ser Leu Val Gly Gln Phe Asn Val Tyr
    290                 295                 300

Asn Val Leu Ala Ala Val Ala Thr Cys Ile Ala Ala Gly Ile Pro Phe
305                 310                 315                 320

Glu Ile Ile Thr Glu Ala Val Glu Glu Leu His Gly Val Arg Gly Arg
                325                 330                 335

Phe Glu Leu Val Asn Gln Gln Glu Phe Pro Val Ile Val Asp Tyr
                340                 345                 350

Ala His Thr Pro Asp Ser Leu Glu Asn Val Leu Glu Thr Cys Arg Asp
            355                 360                 365

Met Thr Glu Gly Lys Leu Phe Val Val Gly Cys Gly Gly Asp Arg
    370                 375                 380

Asp Lys Thr Lys Arg Pro Lys Met Ala Lys Ile Ala Val Glu Leu Ala
385                 390                 395                 400

Asp Glu Pro Ile Phe Thr Ser Asp Asn Pro Arg Ser Glu Asp Pro Arg
                405                 410                 415

Ala Ile Leu Arg Asp Met Glu Ala Gly Val Glu Asn Ala Tyr Tyr His
                420                 425                 430

Ser Ile Ala Asn Arg Glu Gln Ala Ile Phe Phe Ala Ile Ala Asn Ala
            435                 440                 445

Lys Lys Gly Asp Val Val Leu Ile Ala Gly Lys Gly His Glu Thr Tyr
    450                 455                 460

Gln Gln Ile Gly Asn Glu Thr Phe Asp Phe Asp Asp Ala Glu Val Ala
465                 470                 475                 480

Ala Arg Ala Ile Val Glu Leu Asn Lys Asn Lys Thr Asn Ser
                485                 490

(2) INFORMATION FOR SEQ ID NO:4:

(i) SEQUENCE CHARACTERISTICS:
        (A) LENGTH: 488 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Haemophylus influenzae (xi) SEQUENCE DESCRIPTION: SEQ ID NO:4:

Met Lys Lys Leu Thr Ala Leu Phe Asn Leu Pro Glu Leu Lys Asn Asp
1               5                   10                  15

Ile Glu Leu His Asn Met Val Leu Asp Ser Arg Lys Val Lys Ala Gly
                20                  25                  30

Asp Leu Phe Val Ala Ile Lys Gly His Gln Val Asp Gly Asn Gln Phe
            35                  40                  45

Ile Asp Ser Ala Leu His Ser Gly Ala Ser Ala Val Val Ser Glu Thr
    50                  55                  60

Glu Leu Ser Ser Glu His Leu Thr Val Ala Phe Ile Gly Asn Val Pro
65                  70                  75                  80

Val Val Lys Tyr Tyr Gln Leu Ala His His Leu Ser Ser Leu Ala Asp
                85                  90                  95
```

```
Val Phe Tyr Asp Ser Pro Ser Asn Asn Leu Thr Leu Val Gly Val Thr
            100                 105                 110

Gly Thr Asn Gly Lys Thr Thr Ile Ser Gln Leu Leu Ala Gln Trp Ala
            115                 120                 125

Glu Leu Leu Gly His Arg Ala Ala Val Met Gly Thr Ile Gly Asn Gly
            130                 135                 140

Leu Phe Gly Gln Ile Val Glu Ala Lys Asn Thr Thr Gly Ser Ala Val
145                 150                 155                 160

Glu Ile Gln Ser Ser Leu Ser Ala Phe Lys His Ala Gly Ala Asp Phe
                165                 170                 175

Thr Ser Ile Glu Val Ser Ser His Gly Leu Ala Gln His Arg Val Glu
            180                 185                 190

Ala Leu His Phe Lys Ala Ala Ile Phe Thr Asn Leu Thr Arg Asp His
            195                 200                 205

Leu Asp Tyr His Gln Ser Met Glu Asn Tyr Ala Ala Lys Lys Arg
            210                 215                 220

Leu Phe Thr Glu Leu Asp Thr Gln Ile Lys Val Ile Asn Ala Asp Asp
225                 230                 235                 240

Glu Ile Gly Tyr Gln Trp Leu Thr Glu Leu Pro Asp Ala Ile Ala Val
                245                 250                 255

Ser Met Asn Ala Asp Phe Lys Val Gly Ser His Gln Trp Met Lys Ala
            260                 265                 270

Ile Asn Ile His Tyr His Phe Lys Gly Ala Asp Ile Thr Phe Glu Ser
            275                 280                 285

Ser Trp Gly Asn Gly Val Leu His Ser Pro Leu Ile Gly Ala Phe Asn
            290                 295                 300

Val Ser Asn Leu Leu Val Met Thr Thr Leu Leu Ser Phe Gly Tyr
305                 310                 315                 320

Pro Leu Glu Asn Leu Leu Ala Thr Ala Lys Ser Leu Lys Gly Val Cys
                325                 330                 335

Gly Arg Met Glu Met Ile Gln Tyr Pro Asn Lys Pro Thr Val Ile Val
            340                 345                 350

Asp Tyr Ala His Thr Pro Asp Ala Leu Glu Lys Ala Leu Ile Ala Ala
            355                 360                 365

Arg Glu His Cys Gln Gly Glu Leu Trp Cys Ile Phe Gly Cys Gly Gly
            370                 375                 380

Asp Arg Asp Arg Gly Lys Arg Pro Leu Met Ala Gln Val Ala Glu Gln
385                 390                 395                 400

Phe Ala Glu Lys Ile Ile Val Thr Lys Asp Asn Pro Arg Thr Glu Ser
                405                 410                 415

Gln Ser Gln Ile Glu Thr Asp Ile Val Ala Gly Phe Lys Asn Met Glu
            420                 425                 430

Lys Val Gly Ile Ile Pro Asp Arg Ala Gln Ala Ile Gln Phe Ala Ile
            435                 440                 445

Glu Ser Ala Val Glu Asn Asp Val Ile Leu Ile Ala Gly Lys Gly His
            450                 455                 460

Glu His Tyr Gln Ile Ile Gly Ser Glu Val Val His Phe Ser Asp Gln
465                 470                 475                 480

Glu Ile Ala Leu Asp Phe Leu Lys
                485
```

(2) INFORMATION FOR SEQ ID NO:5:

-continued

```
    (i) SEQUENCE CHARISTICS:
        (A) LENGTH: 495 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: E. coli (xi) SEQUENCE DESCRIPTION: SEQ ID NO:5:

Met Ala Asp Arg Asn Leu Arg Asp Leu Leu Ala Pro Trp Val Pro Asp
1               5                  10                  15

Ala Pro Ser Arg Ala Leu Arg Glu Met Thr Leu Asp Ser Arg Val Ala
                20                  25                  30

Ala Ala Gly Asp Leu Phe Val Ala Val Val Gly His Gln Ala Asp Gly
            35                  40                  45

Arg Arg Tyr Ile Pro Gln Ala Ile Ala Gln Gly Val Ala Ala Ile Ile
        50                  55                  60

Ala Glu Ala Lys Asp Glu Ala Thr Asp Gly Glu Ile Arg Glu Met His
65                  70                  75                  80

Gly Val Pro Val Ile Tyr Leu Ser Gln Leu Asn Glu Arg Leu Ser Ala
                85                  90                  95

Leu Ala Gly Arg Phe Tyr His Glu Pro Ser Asp Asn Leu Arg Leu Val
            100                 105                 110

Gly Val Thr Gly Thr Asn Gly Lys Thr Thr Thr Thr Gln Leu Leu Ala
        115                 120                 125

Gln Trp Ser Gln Leu Leu Gly Glu Ile Ser Ala Val Met Gly Thr Val
    130                 135                 140

Gly Asn Gly Leu Leu Gly Lys Val Ile Pro Thr Glu Asn Thr Thr Gly
145                 150                 155                 160

Ser Ala Val Asp Val Gln His Glu Leu Ala Gly Leu Val Asp Gln Gly
                165                 170                 175

Ala Thr Phe Cys Ala Met Glu Val Ser Ser His Gly Leu Val Gln His
            180                 185                 190

Arg Val Ala Ala Leu Lys Phe Ala Ala Ser Val Phe Thr Asn Leu Ser
        195                 200                 205

Arg Asp His Leu Asp Tyr His Gly Asp Met Glu His Tyr Glu Ala Ala
    210                 215                 220

Lys Trp Leu Leu Tyr Ser Glu His His Cys Gly Gln Ala Ile Ile Asn
225                 230                 235                 240

Ala Asp Asp Glu Val Gly Arg Arg Trp Leu Ala Lys Leu Pro Asp Ala
                245                 250                 255

Val Ala Val Ser Met Glu Asp His Ile Asn Pro Asn Cys His Gly Arg
            260                 265                 270

Trp Leu Lys Ala Thr Glu Val Asn Tyr His Asp Ser Gly Ala Thr Ile
        275                 280                 285

Arg Phe Ser Ser Ser Trp Gly Asp Gly Glu Ile Glu Ser His Leu Met
    290                 295                 300

Gly Ala Phe Asn Val Ser Asn Leu Leu Leu Ala Leu Ala Thr Leu Leu
305                 310                 315                 320

Ala Leu Gly Tyr Pro Leu Ala Asp Leu Leu Lys Thr Ala Ala Arg Leu
                325                 330                 335

Gln Pro Val Cys Gly Arg Met Glu Val Phe Thr Ala Pro Gly Lys Pro
```

```
                        340               345               350
Thr Val Val Asp Tyr Ala His Thr Pro Asp Ala Leu Glu Lys Ala
            355               360               365
Leu Gln Ala Ala Arg Leu His Cys Ala Gly Lys Leu Trp Cys Val Phe
    370               375               380
Gly Cys Gly Gly Asp Arg Asp Lys Gly Lys Arg Pro Leu Met Gly Ala
385               390               395               400
Ile Ala Glu Glu Phe Ala Asp Val Ala Val Thr Asp Asp Asn Pro
                405               410               415
Arg Thr Glu Glu Pro Arg Ala Ile Ile Asn Asp Ile Leu Ala Gly Met
            420               425               430
Leu Asp Ala Gly His Ala Lys Val Met Glu Gly Arg Ala Glu Ala Val
            435               440               445
Thr Cys Ala Val Met Gln Ala Lys Glu Asn Asp Val Val Leu Val Ala
    450               455               460
Gly Lys Gly His Glu Asp Tyr Gln Ile Val Gly Asn Gln Arg Leu Asp
465               470               475               480
Tyr Ser Asp Arg Val Thr Val Ala Arg Leu Leu Gly Val Ile Ala
            485               490               495

(2) INFORMATION FOR SEQ ID NO:6:

(i) SEQUENCE CHARACTERISTICS:
        (A) LENGTH: 325 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Pseudomonas aeruginosa (xi) SEQUENCE DESCRIPTION: SEQ ID NO:6:

Met Pro Met Ser Leu Ser Gln Leu Phe Pro Gln Ala Glu Arg Asp Leu
1               5                  10                  15
Leu Ile Arg Glu Leu Thr Leu Asp Ser His Gly Val Arg Pro Val Asp
            20                  25                  30
Leu Phe Leu Thr Val Pro Gly Gly His Gln Asp Gly Arg Ala His Ile
        35                  40                  45
Ala Asp Ala Leu Thr Lys Gly Ala Thr Ala Val Ala Tyr Glu Ala Glu
    50                  55                  60
Gly Ala Gly Glu Leu Pro Pro Ser Asp Ala Pro Leu Ile Ala Val Lys
65                  70                  75                  80
Gly Leu Ala Ala Gln Leu Ser Ala Val Ala Gly Arg Phe Tyr Gly Glu
            85                  90                  95
Pro Ser Arg Gly Leu Asp Leu Ile Gly Val Thr Gly Thr Asn Gly Lys
            100                 105                 110
Thr Ser Val Ser Gln Leu Val Ala Gln Ala Leu Asp Leu Leu Gly Glu
        115                 120                 125
Arg Cys Gly Ile Val Gly Thr Leu Gly Thr Gly Phe Tyr Gly Ala Leu
    130                 135                 140
Glu Ser Gly Arg His Thr Thr Pro Asp Pro Leu Ala Val Gln Ala Thr
145                 150                 155                 160
Leu Ala Thr Leu Lys Gln Ala Gly Ala Arg Ala Val Ala Met Glu Val
            165                 170                 175
```

```
Ser Ser His Gly Leu Asp Gln Gly Arg Val Ala Ala Leu Gly Phe Asp
            180                 185                 190

Ile Ala Val Phe Thr Asn Leu Ser Arg Asp His Leu Asp Tyr His Gly
            195                 200                 205

Ser Met Glu Ala Tyr Ala Ala Lys Ala Lys Leu Phe Ala Trp Pro
            210                 215                 220

Asp Leu Arg Cys Arg Val Ile Asn Leu Asp Asp Phe Gly Arg Arg
225                 230                 235                 240

Leu Ala Gly Glu Glu Gln Asp Ser Glu Leu Ile Thr Tyr Ser Leu Thr
                245                 250                 255

Asp Ser Ser Ala Phe Leu Tyr Cys Arg Glu Ala Arg Phe Gly Asp Ala
            260                 265                 270

Gly Ile Glu Ala Ala Leu Val Thr Pro His Gly Glu Gly Leu Leu Arg
            275                 280                 285

Ser Pro Leu Leu Gly Arg Phe Asn Leu Ser Asn Leu Leu Ala Ala Val
            290                 295                 300

Gly Ala Leu Leu Gly Leu Gly Tyr Pro Leu Gly Asp Ile Leu Arg Thr
305                 310                 315                 320

Leu Pro Gln Leu Gln
                325

(2) INFORMATION FOR SEQ ID NO:7:

(i) SEQUENCE CHARACTERISTICS:
        (A) LENGTH: 517 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Staphylococcus aureus (xi) SEQUENCE DESCRIPTION: SEQ ID NO:7:

Met Asn Leu Lys Gln Glu Val Glu Ser Arg Lys Thr Phe Ala Ile Ile
1               5                   10                  15

Ser His Pro Asp Ala Gly Lys Thr Thr Leu Thr Glu Lys Leu Leu Tyr
            20                  25                  30

Phe Ser Gly Ala Ile Arg Glu Ala Gly Thr Val Lys Gly Lys Lys Leu
            35                  40                  45

Val Asn Leu Arg Gln Val Thr Trp Met Lys Val Glu Gln Glu Arg Gly
50                  55                  60

Ile Ser Val Thr Ser Ser Val Met Gln Phe Asp Tyr Asp Asp Tyr Glu
65                  70                  75                  80

Ile Asn Ile Leu Asp Thr Pro Gly His Glu Asp Phe Glu Asp Tyr Arg
            85                  90                  95

Thr Leu Met Ala Val Asp Ser Ala Val Met Val Ile Asp Cys Ala Lys
            100                 105                 110

Gly Val Glu Pro Leu Lys Leu Phe Lys Val Cys Lys Met Arg Gly Ile
            115                 120                 125

Pro Ile Phe Thr Phe Ile Asn Lys Leu Asp Arg Val Gly Lys Glu Pro
            130                 135                 140

Phe Glu Leu Leu Asp Glu Ile Glu Glu Thr Leu Asn Ile Glu Thr Tyr
145                 150                 155                 160
```

```
Pro Met Asn Trp Pro Ile Gly Met Gly Gln Ser Phe Phe Gly Ile Ile
                165                 170                 175

Asp Arg Lys Ser Lys Thr Ile Glu Pro Phe Arg Asp Glu Glu Asn Ile
                180                 185                 190

Leu His Leu Asn Asp Asp Phe Glu Leu Glu Glu Asp His Ala Ile Thr
                195                 200                 205

Asn Asp Ser Asp Phe Glu Gln Ala Ile Glu Glu Leu Met Leu Val Glu
            210                 215                 220

Glu Ala Gly Glu Ala Phe Asp Asn Asp Ala Leu Leu Ser Gly Asp Leu
225                 230                 235                 240

Thr Pro Val Phe Phe Gly Ser Ala Leu Ala Asn Phe Gly Val Gln Asn
                245                 250                 255

Phe Leu Asn Ala Tyr Val Asp Phe Ala Pro Met Pro Asn Ala Arg Gln
                260                 265                 270

Thr Lys Glu Asn Val Glu Val Ser Pro Phe Asp Asp Ser Phe Ser Gly
                275                 280                 285

Phe Ile Phe Lys Ile Gln Ala Asn Met Asp Pro Lys His Arg Asp Arg
        290                 295                 300

Ile Ala Phe Met Arg Val Val Ser Gly Ala Phe Glu Arg Val Trp Met
305                 310                 315                 320

Leu Leu Cys Asn Val Leu Ile Lys Ser Lys Arg Ser His Val Gln Arg
                325                 330                 335

His Leu Trp Gln Thr Ile Lys Lys Leu Val Asn His Ala Val Ala Gly
                340                 345                 350

Asp Ile Ile Gly Leu Tyr Asp Thr Gly Asn Tyr Gln Ile Gly Asp Thr
                355                 360                 365

Leu Val Gly Gly Lys Gln Thr Tyr Ser Phe Gln Asp Leu Pro Gln Phe
                370                 375                 380

Thr Pro Glu Ile Phe Met Lys Val Ser Ala Lys Asn Val Met Lys Gln
385                 390                 395                 400

Lys His Phe His Lys Gly Ile Glu Gln Leu Val Gln Glu Gly Ala Ile
                405                 410                 415

Gln Tyr Tyr Lys Thr Leu His Thr Asn Gln Ile Ile Leu Gly Ala Val
                420                 425                 430

Gly Gln Leu Gln Phe Glu Val Phe Glu His Arg Met Lys Asn Glu Tyr
                435                 440                 445

Asn Val Asp Val Val Met Glu Pro Val Gly Arg Lys Ile Ala Arg Trp
                450                 455                 460

Asp Ile Glu Asn Glu Asp Gln Ile Thr Asp Lys Met Asn Thr Ser Arg
465                 470                 475                 480

Ser Ile Leu Val Lys Asp Arg Tyr Asp Asp Leu Val Phe Leu Phe Glu
                485                 490                 495

Asn Glu Phe Ala Thr Arg Trp Phe Glu Glu Lys Phe Pro Glu Ile Lys
                500                 505                 510

Leu Tyr Ser Leu Leu
        515

(2) INFORMATION FOR SEQ ID NO:8:

(i) SEQUENCE CHARACTERISTICS:
        (A) LENGTH: 531 amino acids
        (B) TYPE: amino acid
        (C) STRANDEDNESS: single
        (D) TOPOLOGY: linear (ii) MOLECULE TYPE: protein
```

(iii) HYPOTHETICAL: NO (vi) ORIGINAL SOURCE:
         (A) ORGANISM: Dichelobacter (Bacteroides) nodosuss (xi) SEQUENCE DESCRIPTION: SEQ ID NO:8:

Met Ser Asp Ile Leu Ser Gln Asp Trp Arg Asp Arg Thr Phe Ala
1               5                   10                  15

Ile Ile Ser His Pro Asp Ala Gly Lys Thr Thr Leu Thr Glu Lys Leu
                20                  25                  30

Leu Leu Phe Gly Gly Ala Ile Ala Leu Ala Gly Ala Val Lys Gly Arg
            35                  40                  45

Lys Ala Ala His His Ala Thr Ser Asp Trp Met Lys Met Glu Gln Glu
50                      55                  60

Arg Gly Ile Ser Val Thr Ser Ser Val Met Gln Phe Pro Tyr His Gly
65                      70                  75                  80

Lys Val Ile Asn Leu Leu Asp Thr Pro Gly His Glu Asp Phe Ser Glu
                85                  90                  95

Asp Thr Tyr Arg Thr Leu Thr Ala Val Asp Ser Ala Leu Met Val Ile
                100                 105                 110

Asp Cys Ala Lys Gly Val Glu Glu Arg Thr Ile Lys Leu Met Glu Val
            115                 120                 125

Cys Arg Leu Arg Thr Thr Pro Ile Phe Thr Phe Val Asn Lys Leu Asp
130                 135                 140

Arg Asp Gly Arg Glu Pro Met Glu Ile Leu Asp Glu Ile Glu Arg Val
145                 150                 155                 160

Leu His Ile Gln Cys Ala Pro Val Thr Trp Pro Ile Gly Met Gly Arg
                165                 170                 175

Ser Leu Lys Gly Ile Tyr His Leu Ala Arg Asp Thr Val Tyr Phe Tyr
            180                 185                 190

Thr Thr Gly Lys Gly Gly Ala Ser Ile Asn His Gly Glu Thr Val Val
        195                 200                 205

Gly Leu Asp Asn Pro Arg Leu Asp Thr Leu Leu Pro Asp Ile Ile Asp
210                 215                 220

Asp Phe Arg Glu Glu Ile His Phe Leu Arg Glu Val Gly Asn Pro Phe
225                 230                 235                 240

Asp His Glu Ala Tyr Leu Arg Gly Glu Leu Thr Pro Val Tyr Phe Gly
                245                 250                 255

Ser Ala Ile Ser Asn Phe Gly Val Glu Glu Met Leu Thr Asp Phe Ala
            260                 265                 270

Gln Leu Ala Pro Pro Pro Arg Pro His Arg Thr Thr Glu Arg Glu Val
        275                 280                 285

Ala Pro Gln Glu Glu Lys Leu Thr Gly Phe Val Phe Lys Ile Gln Ala
290                 295                 300

Asn Met Asp Leu Lys His Arg Asp Arg Ile Ala Phe Met Arg Val Asn
305                 310                 315                 320

Ser Gly Thr Phe Arg Ala Gly Met Lys Leu Trp Gln Val Arg Leu Gly
                325                 330                 335

Arg Glu Val Lys Ile Pro Asp Ala Leu Thr Phe Leu Ala Ala Glu Arg
            340                 345                 350

Glu His Ala Gln Glu Ala Phe Ala Gly Asp Ile Ile Gly Ile His Asn
        355                 360                 365

His Gly Thr Ile Arg Ile Gly Asp Thr Phe Thr Glu Gly Glu Ser Leu
370                 375                 380

```
Gln Phe Thr Gly Ile Pro Asp Phe Ala Pro Glu Leu Phe Arg Arg Val
385                 390                 395                 400

Gln Leu Lys Asp Pro Leu Lys Met Lys Ala Leu Leu Lys Gly Leu Ala
        405                 410                 415

Gln Leu Cys Glu Glu Gly Ala Thr Gln Phe Phe Lys Pro Leu Ile Gly
            420                 425                 430

Ser Asp Leu Ile Leu Gly Ala Ile Gly Val Leu Gln Phe Glu Val Val
        435                 440                 445

Gln Gln Arg Leu Glu Thr Glu Tyr Asn Val Lys Cys Gln Phe Glu Ser
    450                 455                 460

Val Ala Val Ala Thr Ala Arg Trp Ile Glu Ala Pro Asn Asp Lys Ala
465                 470                 475                 480

Leu Lys Gln Phe Ile Asp Lys Asn Gln Ala Asn Leu Ala His Asp His
                485                 490                 495

Tyr Glu Gln Leu Val Tyr Ile Ala Pro Ser Arg Val Asn Leu Gln Leu
            500                 505                 510

Thr Gln Glu Arg Phe Pro Asp Ile Val Phe Ser Gln Thr Arg Asp His
        515                 520                 525

Leu Ala Gln
    530

(2) INFORMATION FOR SEQ ID NO:9:

(i) SEQUENCE CHARACTERISTICS:
        (A) LENGTH: 527 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Haemophylus influenzae (xi) SEQUENCE DESCRIPTION: SEQ ID NO:9:

Met Ser Tyr Pro Leu Glu Glu Val Asn Lys Arg Arg Thr Phe Ala Ile
1               5                   10                  15

Ile Ser His Pro Asp Ala Gly Lys Thr Thr Ile Thr Glu Lys Val Leu
            20                  25                  30

Leu Tyr Gly Asn Ala Ile Gln Thr Ala Gly Ser Val Lys Gly Lys Gly
        35                  40                  45

Ser Ala Ala His Ala Lys Ser Asp Trp Met Glu Met Glu Lys Gln Arg
50                  55                  60

Gly Ile Ser Ile Thr Thr Ser Val Met Gln Phe Pro Tyr Asn Asp Cys
65              70                  75                  80

Leu Val Asn Leu Leu Asp Thr Pro Gly His Glu Asp Phe Ser Glu Asp
            85                  90                  95

Thr Tyr Arg Thr Leu Thr Ala Val Asp Ser Cys Leu Met Val Ile Asp
        100                 105                 110

Ser Ala Lys Gly Val Glu Glu Arg Thr Ile Lys Leu Met Glu Val Thr
        115                 120                 125

Arg Leu Arg Asp Thr Pro Ile Ile Thr Phe Met Asn Lys Leu Asp Arg
    130                 135                 140

Asp Ile Arg Asp Pro Ile Glu Leu Leu Asp Glu Val Glu Asn Val Leu
145                 150                 155                 160
```

```
Lys Ile Arg Cys Ala Pro Ile Thr Trp Pro Ile Gly Cys Gly Lys Leu
                165                 170                 175

Phe Lys Gly Val Tyr His Leu Ala Lys Asp Glu Thr Tyr Leu Tyr Gln
            180                 185                 190

Ser Gly Gln Gly Ser Thr Ile Gln Ala Val Arg Val Lys Gly Leu
        195                 200                 205

Asn Asn Pro Glu Leu Asp Val Ala Val Gly Asp Leu Ala Gln Gln
    210                 215                 220

Leu Arg Glu Glu Leu Glu Leu Val Gln Gly Ala Ser Asn Glu Phe Glu
225                 230                 235                 240

Gln Asp Ala Phe Ile Lys Gly Glu Leu Thr Pro Val Phe Gly Thr
                245                 250                 255

Ala Leu Gly Asn Phe Gly Val Asp His Phe Leu Asp Gly Leu Thr Gln
                260                 265                 270

Trp Ala Pro Lys Pro Gln Ser Arg Gln Ala Asp Thr Arg Thr Val Glu
            275                 280                 285

Ser Ala Glu Glu Lys Phe Ser Gly Phe Val Phe Lys Ile Gln Ala Asn
    290                 295                 300

Met Asp Pro Lys His Arg Asp Arg Val Ala Phe Met Arg Val Val Ser
305                 310                 315                 320

Gly Lys Tyr Glu Lys Gly Met Lys Leu Lys His Val Arg Ile Gly Lys
                325                 330                 335

Asp Val Val Ile Ser Asp Ala Leu Thr Phe Met Ala Gly Asp Arg Ala
                340                 345                 350

His Ala Glu Glu Ala Tyr Ala Gly Asp Ile Ile Gly Leu His Asn His
            355                 360                 365

Gly Thr Ile Gln Ile Gly Asp Thr Phe Thr Gln Gly Glu Thr Leu Lys
    370                 375                 380

Phe Thr Gly Ile Pro Asn Phe Ala Pro Glu Leu Phe Arg Arg Ile Arg
385                 390                 395                 400

Leu Lys Asp Pro Leu Lys Gln Lys Gln Leu Leu Lys Gly Leu Val Gln
                405                 410                 415

Leu Ser Glu Glu Gly Ala Val Gln Val Phe Arg Pro Leu Leu Asn Asn
            420                 425                 430

Asp Leu Ile Val Gly Ala Val Gly Val Leu Gln Phe Asp Val Val Val
    435                 440                 445

Ser Arg Leu Lys Thr Glu Tyr Asn Val Glu Ala Ile Tyr Glu Asn Val
450                 455                 460

Asn Val Ala Thr Ala Arg Trp Val Glu Cys Ala Asp Glu Lys Lys Phe
465                 470                 475                 480

Glu Glu Phe Lys Arg Lys Asn Glu Gln Asn Leu Ala Leu Asp Gly Gly
                485                 490                 495

Asp Asn Leu Thr Tyr Ile Ala Pro Thr Met Val Asn Leu Asn Leu Ala
            500                 505                 510

Gln Glu Arg Tyr Pro Asp Val Val Phe Tyr Lys Thr Arg Glu His
            515                 520                 525

(2) INFORMATION FOR SEQ ID NO:10:

(i) SEQUENCE CHARACTERISTICS:
        (A) LENGTH: 529 amino acids
        (B) TYPE: amino acid
        (C) STRANDEDNESS: single
        (D) TOPOLOGY: linear (ii) MOLECULE TYPE: protein
```

(iii) HYPOTHETICAL: NO (vi) ORIGINAL SOURCE:
    (A) ORGANISM: E. coli (xi) SEQUENCE DESCRIPTION: SEQ ID NO:10:

```
Met Thr Leu Ser Pro Tyr Leu Gln Glu Val Ala Lys Arg Arg Thr Phe
1               5                   10                  15

Ala Ile Ile Ser His Pro Asp Ala Gly Lys Thr Thr Ile Thr Glu Lys
            20                  25                  30

Val Leu Leu Phe Gly Gln Ala Ile Gln Thr Ala Gly Thr Val Lys Gly
                35                  40                  45

Arg Gly Ser Asn Gln His Ala Lys Ser Asp Trp Met Glu Met Glu Lys
        50                  55                  60

Gln Arg Gly Ile Ser Ile Thr Thr Ser Val Met Gln Phe Pro Tyr His
65                      70                  75                  80

Asp Cys Leu Val Asn Leu Leu Asp Thr Pro Gly His Glu Asp Phe Ser
                    85                  90                  95

Glu Asp Thr Tyr Arg Thr Leu Thr Ala Val Asp Cys Cys Leu Met Val
                100                 105                 110

Ile Asp Ala Ala Lys Gly Val Glu Asp Arg Thr Arg Lys Leu Met Glu
            115                 120                 125

Val Thr Arg Leu Arg Asp Thr Pro Ile Leu Thr Phe Met Asn Lys Leu
130                 135                 140

Asp Arg Asp Ile Arg Asp Pro Met Glu Leu Leu Asp Glu Val Glu Asn
145                 150                 155                 160

Glu Leu Lys Ile Gly Cys Ala Pro Ile Thr Trp Pro Ile Gly Cys Gly
                165                 170                 175

Lys Leu Phe Lys Gly Val Tyr His Leu Tyr Lys Asp Glu Thr Tyr Leu
            180                 185                 190

Tyr Gln Ser Gly Lys Gly His Thr Ile Gln Glu Val Arg Ile Val Lys
            195                 200                 205

Gly Leu Asn Asn Pro Asp Leu Asp Ala Ala Val Gly Glu Asp Leu Ala
            210                 215                 220

Gln Gln Leu Arg Asp Glu Leu Glu Leu Val Lys Gly Ala Ser Asn Glu
225                 230                 235                 240

Phe Asp Lys Glu Leu Phe Leu Ala Gly Glu Ile Thr Pro Val Phe Phe
                245                 250                 255

Gly Thr Ala Leu Gly Asn Phe Gly Val Asp His Met Leu Asp Gly Leu
                260                 265                 270

Val Glu Trp Ala Pro Ala Pro Met Pro Arg Gln Thr Asp Thr Arg Thr
            275                 280                 285

Val Glu Ala Ser Glu Asp Lys Phe Thr Gly Phe Val Phe Lys Ile Gln
290                 295                 300

Ala Asn Met Asp Pro Lys His Arg Asp Arg Leu Ala Phe Met Arg Val
305                 310                 315                 320

Val Ser Gly Lys Tyr Glu Lys Gly Met Lys Leu Arg Gln Val Arg Thr
                325                 330                 335

Ala Lys Asp Val Val Ile Ser Asp Ala Leu Thr Phe Met Ala Gly Asp
            340                 345                 350

Arg Ser His Val Glu Glu Ala Tyr Pro Gly Asp Ile Leu Gly Leu His
            355                 360                 365

Asn His Gly Thr Ile Gln Ile Gly Asp Thr Phe Thr Gln Gly Glu Met
            370                 375                 380
```

```
Met Lys Phe Thr Gly Ile Pro Asn Phe Ala Pro Glu Leu Phe Arg Arg
385                 390                 395                 400

Ile Arg Leu Lys Asp Pro Leu Lys Gln Lys Gln Leu Leu Lys Gly Leu
            405                 410                 415

Val Gln Leu Ser Glu Glu Gly Ala Val Gln Val Phe Arg Pro Ile Ser
            420                 425                 430

Asn Asn Asp Leu Ile Val Gly Ala Val Gly Val Leu Gln Phe Asp Val
            435                 440                 445

Val Val Ala Arg Leu Lys Ser Glu Tyr Asn Val Glu Ala Val Tyr Glu
    450                 455                 460

Ser Val Asn Val Ala Thr Ala Arg Trp Val Glu Cys Ala Asp Ala Lys
465                 470                 475                 480

Lys Phe Glu Glu Phe Lys Arg Lys Asn Glu Ser Gln Leu Ala Leu Asp
                485                 490                 495

Gly Gly Asp Asn Leu Ala Tyr Ile Ala Thr Ser Met Val Asn Leu Arg
            500                 505                 510

Leu Ala Gln Glu Arg Tyr Pro Asp Val Gln Phe His Gln Thr Arg Glu
        515                 520                 525

His
```

(2) INFORMATION FOR SEQ ID NO:11:

(i) SEQUENCE CHARACTERISTICS:
        (A) LENGTH: 391 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Staphylococcus aureus (xi) SEQUENCE DESCRIPTION: SEQ ID NO:11:

```
Met Val Thr Gln Asn Lys Lys Ile Leu Ile Ile Thr Gly Ser Phe Gly
1                   5                   10                  15

Asn Gly His Met Gln Val Thr Gln Ser Ile Val Asn Gln Leu Asn Asp
                20                  25                  30

Met Asn Leu Asp His Leu Ser Val Ile Glu His Asp Leu Phe Met Glu
            35                  40                  45

Ala His Pro Ile Leu Thr Ser Ile Cys Lys Lys Trp Tyr Ile Asn Ser
    50                  55                  60

Phe Lys Tyr Phe Arg Asn Met Tyr Lys Gly Phe Tyr Tyr Ser Arg Pro
65                  70                  75                  80

Asp Lys Leu Asp Lys Cys Phe Tyr Lys Tyr Tyr Gly Leu Asn Lys Leu
                85                  90                  95

Ile Asn Leu Leu Ile Lys Glu Lys Pro Asp Leu Ile Leu Leu Thr Phe
            100                 105                 110

Pro Thr Pro Val Met Ser Val Leu Thr Glu Gln Phe Asn Ile Asn Ile
        115                 120                 125

Pro Val Ala Thr Val Met Thr Asp Tyr Arg Leu His Lys Asn Trp Ile
    130                 135                 140

Thr Pro Tyr Ser Thr Arg Tyr Tyr Val Ala Thr Lys Glu Thr Lys Gln
145                 150                 155                 160

Asp Phe Ile Asp Val Gly Ile Asp Pro Ser Thr Val Lys Val Thr Gly
```

```
                    165                 170                 175
Ile Pro Ile Asp Asn Lys Phe Glu Thr Pro Ile Asn Gln Lys Gln Trp
                180                 185                 190

Leu Ile Asp Asn Asn Leu Asp Pro Asp Lys Gln Thr Ile Leu Met Ser
            195                 200                 205

Ala Gly Ala Phe Gly Val Ser Lys Gly Phe Asp Thr Met Ile Thr Asp
        210                 215                 220

Ile Leu Ala Lys Ser Ala Asn Ala Gln Val Val Met Ile Cys Gly Lys
225                 230                 235                 240

Ser Lys Glu Leu Lys Arg Ser Leu Thr Ala Lys Phe Lys Leu Thr Arg
                245                 250                 255

Met Tyr Leu Ile Leu Gly Tyr Thr Lys His Met Asn Glu Trp Met Ala
            260                 265                 270

Ser Ser Gln Leu Met Ile Thr Lys Pro Gly Gly Ile Thr Ile Thr Glu
        275                 280                 285

Gly Phe Ala Arg Cys Ile Pro Met Ile Phe Leu Asn Pro Ala Pro Gly
    290                 295                 300

Gln Glu Leu Glu Asn Ala Phe Tyr Phe Glu Glu Lys Gly Phe Gly Lys
305                 310                 315                 320

Ile Ala Asp Thr Pro Glu Glu Ala Ile Lys Ile Val Ala Ser Leu Thr
                325                 330                 335

Asn Gly Asn Glu Gln Leu Thr Asn Met Ile Ser Thr Met Glu Gln Asp
            340                 345                 350

Lys Ile Lys Tyr Ala Thr Gln Thr Ile Cys Arg Asp Leu Leu Asp Leu
        355                 360                 365

Ile Gly His Ser Ser Gln Pro Gln Glu Ile Tyr Gly Lys Val Pro Leu
    370                 375                 380

Tyr Ala Arg Phe Phe Val Lys
385                 390

(2) INFORMATION FOR SEQ ID NO:12:

(i) SEQUENCE CHARACTERISTICS:
        (A) LENGTH: 382 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Bacillus subtilis (xi) SEQUENCE DESCRIPTION: SEQ ID NO:12:

Met Asn Thr Asn Lys Arg Val Leu Ile Leu Thr Ala Asn Tyr Gly Asn
1               5                   10                  15

Gly His Val Gln Val Ala Lys Thr Leu Tyr Glu Gln Cys Val Arg Leu
            20                  25                  30

Gly Phe Gln His Val Thr Val Ser Asn Leu Tyr Gln Glu Ser Asn Pro
        35                  40                  45

Ile Val Ser Glu Val Thr Gln Tyr Leu Tyr Leu Lys Ser Phe Ser Ile
    50                  55                  60

Gly Lys Gln Phe Tyr Arg Leu Phe Tyr Tyr Gly Val Asp Lys Ile Tyr
65                  70                  75                  80

Asn Lys Arg Lys Phe Asn Ile Tyr Phe Lys Met Gly Asn Lys Arg Leu
                85                  90                  95
```

```
Gly Glu Leu Val Asp Glu His Gln Pro Asp Ile Ile Asn Thr Phe
            100                 105                 110

Pro Met Ile Val Val Pro Glu Tyr Arg Arg Thr Gly Arg Val Ile
            115                 120                 125

Pro Thr Phe Asn Val Met Thr Asp Phe Cys Leu His Lys Ile Trp Val
            130                 135                 140

His Glu Asn Val Asp Lys Tyr Tyr Val Ala Thr Asp Tyr Val Lys Glu
145                 150                 155                 160

Lys Leu Leu Glu Ile Gly Thr His Pro Ser Asn Val Lys Ile Thr Gly
                165                 170                 175

Ile Pro Ile Arg Pro Gln Phe Glu Gly Ser Met Pro Val Gly Pro Ile
            180                 185                 190

Tyr Lys Lys Tyr Asn Leu Ser Pro Asn Lys Val Leu Leu Ile Met
            195                 200                 205

Ala Gly Ala His Gly Val Leu Lys Asn Val Lys Glu Leu Cys Glu Asn
            210                 215                 220

Leu Val Lys Asp Asp Gln Val Gln Val Val Val Cys Gly Lys Asn
225                 230                 235                 240

Thr Ala Leu Lys Glu Ser Leu Ser Ala Leu Glu Ala Glu Asn Gly Asp
                245                 250                 255

Lys Leu Lys Val Leu Gly Tyr Val Glu Arg Ile Asp Glu Leu Phe Arg
                260                 265                 270

Ile Thr Asp Cys Met Ile Thr Lys Pro Gly Gly Ile Thr Leu Thr Glu
            275                 280                 285

Ala Thr Ala Ile Gly Val Pro Val Ile Leu Tyr Lys Pro Val Pro Gly
            290                 295                 300

Gln Glu Lys Glu Asn Ala Asn Phe Phe Glu Asp Arg Gly Ala Ala Ile
305                 310                 315                 320

Val Val Asn Arg His Glu Glu Ile Leu Glu Ser Val Thr Ser Leu Leu
                325                 330                 335

Ala Asp Glu Asp Thr Leu His Arg Met Lys Lys Asn Ile Lys Asp Leu
                340                 345                 350

His Leu Ala Asn Ser Ser Glu Val Ile Leu Glu Asp Ile Leu Lys Glu
            355                 360                 365

Ser Glu Met Met Thr Ala Lys Gln Lys Ala Lys Val Leu Ser
            370                 375                 380

(2) INFORMATION FOR SEQ ID NO:13:

(i) SEQUENCE CHARACTERISTICS:
        (A) LENGTH: 363 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Bacillus subtilis (xi) SEQUENCE DESCRIPTION: SEQ ID NO:13:

Met Arg Ile Ala Ile Ser Gly Gly Gly Thr Gly Gly His Ile Tyr Pro
1               5                   10                  15

Ala Leu Ala Phe Ile Lys Glu Val Gln Arg Arg His Pro Asn Val Glu
            20                  25                  30
```

-continued

```
Phe Leu Tyr Ile Gly Thr Glu Asn Gly Leu Glu Lys Lys Ile Val Glu
         35                  40                  45

Arg Glu Asn Ile Pro Phe Arg Ser Ile Glu Ile Thr Gly Phe Lys Arg
 50                  55                  60

Lys Leu Ser Phe Glu Asn Val Lys Thr Val Met Arg Phe Leu Lys Gly
 65                  70                  75                  80

Val Lys Lys Ser Lys Ser Tyr Leu Ala Glu Phe Lys Pro Asp Ala Val
                 85                  90                  95

Ile Gly Thr Gly Gly Tyr Val Cys Gly Pro Val Val Tyr Ala Ala Ala
                100                 105                 110

Lys Met Gly Ile Pro Thr Ile Val His Glu Gln Asn Ser Leu Pro Gly
                115                 120                 125

Ile Thr Asn Lys Phe Leu Ser Lys Tyr Val Asn Lys Val Ala Ile Cys
                130                 135                 140

Phe Glu Glu Ala Lys Ser His Phe Pro Ser Glu Lys Val Val Phe Thr
145                 150                 155                 160

Gly Asn Pro Arg Ala Ser Glu Val Val Ser Ile Lys Thr Gly Arg Ser
                165                 170                 175

Leu Ala Glu Phe Lys Leu Ser Glu Asp Lys Lys Thr Val Leu Ile Phe
                180                 185                 190

Gly Gly Ser Arg Gly Ala Ala Pro Ile Asn Arg Ala Val Ile Asp Met
                195                 200                 205

Gln Asp Val Leu Lys Thr Arg Asp Tyr Gln Val Leu Tyr Ile Thr Gly
210                 215                 220

Glu Val His Tyr Glu Lys Val Met Asn Glu Leu Lys Ser Lys Gly Ala
225                 230                 235                 240

Ala Asp Asn Met Val Thr Lys Pro Phe Leu His Gln Met Pro Glu Tyr
                245                 250                 255

Leu Lys Ala Ile Asp Val Ile Val Ala Arg Ala Gly Ala Ala Thr Ile
                260                 265                 270

Ala Glu Ile Thr Ala Leu Gly Ile Pro Ser Val Leu Ile Pro Ser Pro
                275                 280                 285

Tyr Val Thr Ala Asn His Gln Glu Val Asn Ala Arg Ser Leu Gly Gln
                290                 295                 300

His Asp Ala Ala Ile Val Leu Lys Glu Thr Glu Leu Ser Gly Glu Lys
305                 310                 315                 320

Leu Ile Glu Ala Leu Asp Arg Ile Val Leu Asn Glu Gln Thr Leu Lys
                325                 330                 335

Glu Met Ser Glu Arg Thr Lys Ser Leu Gly Val Pro Asp Ala Ala Ala
                340                 345                 350

Arg Leu Tyr Ser Val Leu Glu Glu Leu Lys Lys
                355                 360
```

(2) INFORMATION FOR SEQ ID NO:14:

(i) SEQUENCE CHARACTERISTICS:
        (A) LENGTH: 355 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
       (A) ORGANISM: E. coli -continued (xi) SEQUENCE DESCRIPTION: SEQ ID NO:14:

```
Met Ser Gly Gln Gly Lys Arg Leu Met Val Met Ala Gly Thr Gly
1               5                   10                  15

Gly His Val Phe Pro Gly Leu Ala Val Ala His His Leu Met Ala Gln
            20                  25                  30

Gly Trp Gln Val Arg Trp Leu Gly Thr Ala Asp Arg Met Glu Ala Asp
        35                  40                  45

Leu Val Pro Lys His Gly Ile Glu Ile Asp Phe Ile Arg Ile Ser Gly
    50                  55                  60

Leu Arg Gly Lys Gly Ile Lys Ala Leu Ile Ala Ala Pro Leu Arg Ile
65                  70                  75                  80

Phe Asn Ala Trp Arg Gln Ala Arg Ala Ile Met Lys Ala Tyr Lys Pro
                85                  90                  95

Asp Val Val Leu Gly Met Gly Gly Tyr Val Ser Gly Pro Gly Gly Leu
            100                 105                 110

Ala Ala Trp Ser Leu Gly Ile Pro Val Val Leu His Glu Gln Asn Gly
        115                 120                 125

Ile Ala Gly Leu Thr Asn Lys Trp Leu Ala Lys Ile Ala Thr Lys Val
    130                 135                 140

Met Gln Ala Phe Pro Gly Ala Phe Pro Asn Ala Glu Val Val Gly Asn
145                 150                 155                 160

Pro Val Arg Thr Asp Val Leu Ala Leu Pro Leu Pro Gln Gln Arg Leu
                165                 170                 175

Ala Gly Arg Glu Gly Pro Val Arg Val Leu Val Val Gly Gly Ser Gln
            180                 185                 190

Gly Ala Arg Ile Leu Asn Gln Thr Met Pro Gln Val Ala Ala Lys Leu
        195                 200                 205

Gly Asp Ser Val Thr Ile Trp His Gln Ser Gly Lys Gly Ser Gln Gln
    210                 215                 220

Ser Val Glu Gln Ala Tyr Ala Glu Ala Gly Gln Pro His Lys Val
225                 230                 235                 240

Thr Glu Phe Ile Asp Asp Met Ala Ala Ala Tyr Ala Trp Ala Asp Val
                245                 250                 255

Val Val Cys Arg Ser Gly Ala Leu Thr Val Ser Glu Ile Ala Ala Ala
            260                 265                 270

Gly Leu Pro Ala Leu Phe Val Pro Phe Gln His Lys Asp Arg Gln Gln
        275                 280                 285

Tyr Trp Asn Ala Leu Pro Leu Glu Lys Ala Gly Ala Ala Lys Ile Ile
    290                 295                 300

Glu Gln Pro Gln Leu Ser Val Asp Ala Val Ala Asn Thr Leu Ala Gly
305                 310                 315                 320

Trp Ser Arg Glu Thr Leu Leu Thr Met Ala Glu Arg Ala Arg Ala Ala
                325                 330                 335

Ser Ile Pro Asp Ala Thr Glu Arg Val Ala Asn Glu Val Ser Arg Val
            340                 345                 350

Ala Arg Ala
        355
```

(2) INFORMATION FOR SEQ ID NO:15:

(i) SEQUENCE CHARACTERISTICS:
        (A) LENGTH: 351 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
         (A) ORGANISM: Haemophylus influenzaes (xi) SEQUENCE DESCRIPTION: SEQ ID NO:15:

```
Met Lys Asn Lys Lys Leu Leu Val Met Ala Gly Gly Thr Gly Gly His
1               5                   10                  15

Val Phe Pro Ala Ile Ala Val Ala Gln Thr Leu Gln Lys Gln Glu Trp
            20                  25                  30

Asp Ile Cys Trp Leu Gly Thr Lys Asp Arg Met Glu Ala Gln Leu Val
        35                  40                  45

Pro Lys Tyr Gly Ile Pro Ile Arg Phe Ile Gln Ile Ser Gly Leu Arg
    50                  55                  60

Gly Lys Gly Ile Lys Ala Leu Leu Asn Ala Pro Phe Ala Ile Phe Arg
65                  70                  75                  80

Ala Val Leu Gln Ala Lys Lys Ile Ile Gln Glu Glu Lys Pro Asp Ala
                85                  90                  95

Val Leu Gly Met Gly Gly Tyr Val Ser Gly Pro Ala Gly Val Ala Ala
                100                 105                 110

Lys Leu Cys Gly Val Pro Ile Ile Leu His Glu Gln Asn Ala Ile Ala
            115                 120                 125

Gly Leu Thr Asn Lys Leu Leu Gly Lys Ile Ala Thr Cys Val Leu Gln
        130                 135                 140

Ala Phe Pro Thr Ala Phe Pro His Ala Glu Val Val Gly Asn Pro Val
145                 150                 155                 160

Arg Glu Asp Leu Phe Glu Met Pro Asn Pro Asp Ile Arg Phe Ser Asp
                165                 170                 175

Arg Glu Glu Lys Leu Arg Val Leu Val Gly Gly Ser Gln Gly Ala
                180                 185                 190

Arg Val Leu Asn His Thr Leu Pro Lys Val Val Ala Gln Leu Ala Asp
            195                 200                 205

Lys Leu Glu Phe Arg His Gln Val Gly Lys Gly Ala Val Glu Glu Val
        210                 215                 220

Ser Gln Leu Tyr Gly Glu Asn Leu Glu Gln Val Lys Ile Thr Glu Phe
225                 230                 235                 240

Ile Asp Asn Met Ala Glu Ala Tyr Ala Trp Ala Asp Val Val Ile Cys
                245                 250                 255

Arg Ser Gly Ala Leu Thr Val Cys Glu Ile Ala Ala Val Gly Ala Ala
                260                 265                 270

Ala Ile Phe Val Pro Phe Gln His Lys Asp Arg Gln Gln Tyr Leu Asn
            275                 280                 285

Ala Lys Tyr Leu Ser Asp Val Gly Ala Ala Lys Ile Ile Glu Gln Ala
        290                 295                 300

Asp Leu Thr Pro Glu Ile Leu Val Asn Tyr Leu Lys Asn Leu Thr Arg
305                 310                 315                 320

Glu Asn Leu Leu Gln Met Ala Leu Lys Ala Lys Thr Met Ser Met Pro
                325                 330                 335

Asn Ala Ala Gln Arg Val Ala Glu Val Ile Lys Gln Tyr Ser Asn
                340                 345                 350
```

(2) INFORMATION FOR SEQ ID NO:16:

(i) SEQUENCE CHARACTERISTICS:
    (A) LENGTH: 363 amino acids
    (B) TYPE: amino acid
    (C) STRANDEDNESS: single
    (D) TOPOLOGY: linear (ii) MOLECULE TYPE: protein (iii) HYPOTHETICAL: NO (vi) ORIGINAL SOURCE:
    (A) ORGANISM: Enterococcus faecalis (xi) SEQUENCE DESCRIPTION: SEQ ID NO:16:

```
Met Lys Ile Leu Val Thr Gly Gly Thr Gly His Ile Tyr Pro
1               5                   10                  15

Ala Leu Ser Phe Val Glu His Val Lys Lys Glu Ala Pro Ala Thr Glu
                20                  25                  30

Phe Leu Tyr Val Gly Thr Glu Asn Gly Leu Glu Ser Gln Ile Val Pro
                35                  40                  45

Lys Ala Lys Ile Pro Phe Lys Thr Ile Lys Ile Gln Gly Phe Lys Arg
50                  55                  60

Ser Leu Ser Pro Gln Asn Phe Lys Thr Ile Tyr Leu Phe Leu Thr Ser
65                  70                  75                  80

Ile Asn Lys Ala Lys Lys Ile Ile Arg Glu Phe Gln Pro Asp Val Val
                85                  90                  95

Ile Gly Thr Gly Gly Tyr Val Ser Gly Ala Val Val Tyr Ala Ala His
                100                 105                 110

Gln Leu Lys Ile Pro Thr Ile Ile His Glu Gln Asn Ser Ile Pro Gly
            115                 120                 125

Met Thr Asn Lys Phe Leu Ser Arg Tyr Val Asp Lys Ile Ala Ile Cys
    130                 135                 140

Phe Pro Asp Val Ala Ser Phe Phe Pro Lys Glu Lys Thr Ile Leu Thr
145                 150                 155                 160

Gly Asn Pro Arg Gly Gln Glu Val Val Thr Val Glu Lys Ser Ala Ile
                165                 170                 175

Leu Ser Glu Phe Gly Leu Asp Pro Ala Lys Lys Thr Val Val Leu Phe
                180                 185                 190

Gly Gly Ser Arg Gly Ala Leu Lys Ile Asn Gln Ala Phe Glu Gln Ala
            195                 200                 205

Phe Pro Leu Phe Glu Glu Arg Glu Tyr Gln Val Leu Tyr Ala Ser Gly
210                 215                 220

Glu Arg Tyr Tyr Gln Glu Leu Gln Glu Ser Leu Lys Leu Ser Glu Lys
225                 230                 235                 240

Lys Leu Thr Asn Ile Ser Val Gln Pro Tyr Ile Asp Lys Met Val Glu
                245                 250                 255

Val Met Ala Asn Thr Asp Leu Met Val Gly Arg Ala Gly Ala Thr Ser
            260                 265                 270

Ile Ala Glu Phe Thr Ala Leu Gly Leu Pro Ala Ile Leu Ile Pro Ser
            275                 280                 285

Pro Tyr Val Thr Asn Asp His Gln Thr Lys Asn Ala Gln Ser Leu Val
        290                 295                 300

Lys Val Gly Ala Val Glu Met Ile Pro Asp Ala Glu Leu Thr Gly Ala
305                 310                 315                 320

Arg Leu Val Ala Ala Ile Asp Asp Ile Leu Leu Asn Asn Glu Lys Arg
                325                 330                 335

Gln Gln Met Ala Thr Ala Ser Lys Gly Glu Arg Ile Pro Asp Ala Ser
```

```
                340           345           350
Asp Arg Leu Tyr Gln Val Val Lys Thr Leu Val
        355               360
```

(2) INFORMATION FOR SEQ ID NO:17:

(i) SEQUENCE CHARACTERISTICS:
        (A) LENGTH: 525 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Cucumis sativus (xi) SEQUENCE DESCRIPTION: SEQ ID NO:17:

```
Met Arg Asn Pro Ser Thr Val Val Gln Glu Asn Gly Ser Val Ser Asp
1               5                   10                  15

Phe Ile Ser Gln Leu Gly Tyr Phe Ala Phe Ser Ser Arg Phe Leu Asn
            20                  25                  30

Leu Asn Ser Glu Gly Cys Ser Gly Ser Ser Ser His Ser Leu Tyr Leu
        35                  40                  45

Asn Gly Phe Glu Asn Tyr Arg Cys Val Lys Arg Pro Pro Arg Ser Gly
    50                  55                  60

Ala Ser Leu Ser Leu Ser Ser Arg Gly Ser Ser Ser Leu Arg Arg Phe
65                  70                  75                  80

Val Asn Glu Phe Asn Asn Val Ile Lys Phe His Cys His Lys Pro Pro
                85                  90                  95

Leu Gly Phe Ala Ser Leu Gly Gly Val Ser Asp Glu Thr Asn Gly Ile
            100                 105                 110

Arg Asp Asp Gly Phe Gly Val Ser Gln Asp Gly Ala Leu Pro Leu Asn
        115                 120                 125

Lys Ile Glu Ala Glu Asn Pro Lys Arg Val Leu Ile Leu Met Ser Asp
    130                 135                 140

Thr Gly Gly Gly His Arg Ala Ser Ala Glu Ala Ile Lys Ala Ala Phe
145                 150                 155                 160

Asn Glu Glu Phe Gly Asn Asn Tyr Gln Val Phe Ile Thr Asp Leu Trp
                165                 170                 175

Thr Asp His Thr Pro Trp Pro Phe Asn Gln Leu Pro Arg Ser Tyr Asn
            180                 185                 190

Phe Leu Val Lys His Gly Thr Leu Trp Lys Met Thr Tyr Tyr Val Thr
        195                 200                 205

Ala Pro Lys Val Ile His Gln Ser Asn Phe Ala Ala Thr Ser Thr Phe
    210                 215                 220

Ile Ala Arg Glu Val Ala Lys Gly Leu Met Lys Tyr Arg Pro Asp Ile
225                 230                 235                 240

Ile Ile Ser Val His Pro Leu Met Gln His Val Pro Ile Arg Ile Leu
                245                 250                 255

Arg Ser Lys Gly Leu Leu Asn Lys Ile Val Phe Thr Thr Val Val Thr
            260                 265                 270

Asp Leu Ser Thr Cys His Pro Thr Trp Phe His Lys Leu Val Thr Arg
        275                 280                 285

Cys Tyr Cys Pro Ser Thr Glu Val Ala Lys Arg Ala Leu Thr Ala Gly
    290                 295                 300
```

-continued

```
Leu Gln Pro Ser Lys Leu Lys Val Phe Gly Leu Pro Val Arg Pro Ser
305                 310                 315                 320

Phe Val Lys Pro Ile Arg Pro Lys Ile Glu Leu Arg Lys Glu Leu Gly
                325                 330                 335

Met Asp Glu Asn Leu Pro Ala Val Leu Leu Met Gly Gly Gly Glu Gly
                340                 345                 350

Met Gly Pro Ile Glu Ala Thr Ala Lys Ala Leu Ser Lys Ala Leu Tyr
            355                 360                 365

Asp Glu Asn His Gly Glu Pro Ile Gly Gln Val Leu Val Ile Cys Gly
            370                 375                 380

His Asn Lys Lys Leu Ala Gly Arg Leu Arg Ser Ile Asp Trp Lys Val
385                 390                 395                 400

Pro Val Gln Val Lys Gly Phe Val Thr Lys Met Glu Glu Cys Met Gly
                405                 410                 415

Ala Cys Asp Cys Ile Ile Thr Lys Ala Gly Pro Gly Thr Ile Ala Glu
                420                 425                 430

Ala Met Ile Arg Gly Leu Pro Ile Ile Leu Asn Asp Tyr Ile Ala Gly
            435                 440                 445

Gln Glu Ala Gly Asn Val Pro Tyr Val Val Glu Asn Gly Cys Gly Lys
        450                 455                 460

Phe Ser Lys Ser Pro Lys Glu Ile Ala Asn Ile Val Ala Lys Trp Phe
465                 470                 475                 480

Gly Pro Lys Ala Asp Glu Leu Leu Ile Met Ser Gln Asn Ala Leu Arg
                485                 490                 495

Leu Ala Arg Pro Asp Ala Val Phe Lys Ile Val His Asp Leu His Glu
                500                 505                 510

Leu Val Lys Gln Arg Ser Phe Val Pro Gln Tyr Ser Gly
        515                 520                 525
```